(12) United States Patent
Millroy et al.

(10) Patent No.: US 9,422,563 B2
(45) Date of Patent: Aug. 23, 2016

(54) CD7 RECEPTOR APTAMERS

(71) Applicant: University of the Witwatersrand, Johannesburg, Johannesburg (ZA)

(72) Inventors: Laura Ann Millroy, Gauteng (ZA); Makobetsa Abel Khati, Gauteng (ZA); Mark Saul Weinberg, Gauteng (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 0 days.

(21) Appl. No.: 14/775,615

(22) PCT Filed: Mar. 18, 2014

(86) PCT No.: PCT/IB2014/059944
§ 371 (c)(1),
(2) Date: Sep. 11, 2015

(87) PCT Pub. No.: WO2014/147559
PCT Pub. Date: Sep. 25, 2014

(65) Prior Publication Data
US 2016/0032291 A1 Feb. 4, 2016

(30) Foreign Application Priority Data
Mar. 18, 2013 (ZA) .................... 2013/02010

(51) Int. Cl.
*C12N 15/11* (2006.01)
*C12N 15/115* (2010.01)
*A61K 31/7088* (2006.01)
*C12Q 1/68* (2006.01)

(52) U.S. Cl.
CPC .......... *C12N 15/115* (2013.01); *A61K 31/7088* (2013.01); *C12Q 1/6876* (2013.01); *C12N 2310/16* (2013.01); *C12N 2320/10* (2013.01); *C12N 2320/30* (2013.01)

(58) Field of Classification Search
CPC .......................... C12N 15/115; C12Q 1/6876
See application file for complete search history.

(56) References Cited

U.S. PATENT DOCUMENTS

2009/0117549 A1  5/2009  Tan et al.

FOREIGN PATENT DOCUMENTS

WO  WO2007142713 A2  12/2007
WO  WO2013042077 A1  3/2013

*Primary Examiner* — Brian Whiteman
(74) *Attorney, Agent, or Firm* — Bret E. Field; Bozicevic, Field & Francis LLP

(57) ABSTRACT

Nucleic acid aptamers which bind specifically to or are internalised into cells expressing a CD7 cell-surface receptor are disclosed. The aptamers comprise a nucleic acid molecule having a sequence which is at least 80% identical to 5'-GG-GAGACAAGAAUAAGCAUG-R1-UUCGACAG-GAGGCUCACAACAGnynz-3' (SEQ ID NO: 3). The aptamers can be linked to therapeutic or diagnostic molecules, and can be used to deliver the therapeutic or diagnostic molecules to cells expressing the CD7 receptor. The aptamers can also be used as detection tools.

19 Claims, 21 Drawing Sheets

SEQUENCE LISTING

```
<160> NUMBER OF SEQ ID NOS: 124

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 1
gggagacaag aauaagcaug                                                    20

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 2
uucgacagga ggcucacaac aggc                                               24

<210> SEQ ID NO 3
<211> LENGTH: 99
<212> TYPE: RNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (21)..(75)
<223> OTHER INFORMATION: a, c, g, u, or absent, and this region may
      encompass 20 to 55 nucleotides

<400> SEQUENCE: 3
gggagacaag aauaagcaug nnnnnnnnnn nnnnnnnnnn nnnnnnnnnn nnnnnnnnnn        60
nnnnnnnnnn nnnnnuucga caggaggcuc acaacaggc                               99

<210> SEQ ID NO 4
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 4
```
aaaccccaac ucuggcgcac auuuccccgc caccaccgua gaauacuuc            49

<210> SEQ ID NO 5
<211> LENGTH: 48
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 5
cccuucccua gaacgcaggc agcaguuacu cggagaaccc uacccuuc             48

<210> SEQ ID NO 6
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 6
ggaccccaac uagcguguca uuguucgaau cgacugagau uucggguuc            49

<210> SEQ ID NO 7
<211> LENGTH: 43
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 7
agacugaucc aaauacgaca caaauacccg gcacuagacg uuc                  43

<210> SEQ ID NO 8
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 8
agcaucaauc uagacuagac ucagauuacc agcgaacuag uguaucuuc            49

<210> SEQ ID NO 9
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 9
uaauuccagc auaaaaaaga uagguacuau uaauacacga ccagaauuc            49

<210> SEQ ID NO 10
<211> LENGTH: 39
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 10
aucuacgcga ccacaaaauu auccgcgauu ugaauauuc          39

<210> SEQ ID NO 11
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 11
ccccuugcgg uucccacauu aucucucugc uaucccgaug gcccgauuc          49

<210> SEQ ID NO 12
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 12
agacauucuc uccgcccuca acuccgcccg cuccauccag uucccuguc          49

<210> SEQ ID NO 13
<211> LENGTH: 47
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 13
gccgauccau ccuccccacg accaucauga aucccaacag gaacuuc            47

<210> SEQ ID NO 14
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 14
ggauaguucu gcguagcuua agagauguua aaucacaccc acgccauuc          49

<210> SEQ ID NO 15
<211> LENGTH: 44
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 15
gcuaucauac ccgagaccgc uauccccac cuuaauguuc cuuc                44

<210> SEQ ID NO 16
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 16
agaccguaca ccucgcucgc cauccgacuu ugaauaagca uagaccuuc          49

<210> SEQ ID NO 17
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 17
agcgccaaua ugaccgcgac aucguuugaa uaguuccugg ggaucuuuc          49

<210> SEQ ID NO 18
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 18
ccggauaagg ucguccguag uaccgguuaa cguaccagcc uuacucuuc          49

<210> SEQ ID NO 19
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 19
aucuaaagac agauuuaaua cuacccgucg uauccaacuc ggaacgguc          49

<210> SEQ ID NO 20
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 20
uacguagaca agagauuucc agacccuguu acuaauacau ucccguuc          49

<210> SEQ ID NO 21
<211> LENGTH: 9
<212> TYPE: RNA
<213> ORGANISM: Artificial Sequence
<220> FEATURE:
<223> OTHER INFORMATION: Synthetic Oligonucleotide

<400> SEQUENCE: 21 ccuacauuc          9

<210> SEQ ID NO 22
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 22
cucugacaau ccugcaacaa uuacauucau uaacgggcua auucauauc          49

```
<210> SEQ ID NO 23
<211> LENGTH: 47
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 23
auauguagua accccaauga uaaauaacua agaccgcaag ucaguuc                   47

<210> SEQ ID NO 24
<211> LENGTH: 47
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 24
ccacucccac acuccuuaa uccgcgcuaa cacaccauau guacuuc                    47

<210> SEQ ID NO 25
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 25
cguuagcaga uacaucgaga uugcaaaguc caauacaguu aauaaguuc                 49

<210> SEQ ID NO 26
<211> LENGTH: 48
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 26
gagugcgucg ccacuacucc ucucauuacc ucuugcauuu cacuauuc                  48

<210> SEQ ID NO 27
<211> LENGTH: 47
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 27 ccccaccccca cuauuagccg aacccgaacc ccaucuuacc cggaccc                  47

<210> SEQ ID NO 28
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 28
uucucugcgg ucuaggucac gauauacccg uuacauauca uuccuguuc                 49

<210> SEQ ID NO 29
```

```
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 29
uacaaauccg cauauacacc caaccacacc caauccucuc aguccauuc                49

<210> SEQ ID NO 30
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 30
cccuagcaac auucuaugcg caaaccauag uuaugacuau ugacucuuc                49

<210> SEQ ID NO 31
<211> LENGTH: 48
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 31
cacaccggcu gaguaucugc cuguguaauc gaaacaacug cgacauuc                 48

<210> SEQ ID NO 32
<211> LENGTH: 46
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 32
ccgcacccgu accuccuucc ucucagguau ucacucacau cauuuc                   46

<210> SEQ ID NO 33
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 33
cacggaugac agcagaauaa cuccuacagu ccauauauaa acgauuuc                 49

<210> SEQ ID NO 34
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 34
caauuuaucg agacccagau aaccgauuua uacgcagacg auaaguuuc                49

<210> SEQ ID NO 35
<211> LENGTH: 49
```

<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 35
agccccacau ccuacgccac ucacccacgc aucccgauug aucaaauuc         49

<210> SEQ ID NO 36
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 36
gggauagccg cacuucucac aggagucgag ucuuuugauc ggucucuuc         49

<210> SEQ ID NO 37
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 37
cgugcgccua ugaugagucu gguucacaua auuugcguua guuaguuuc         49

<210> SEQ ID NO 38
<211> LENGTH: 8
<212> TYPE: RNA
<213> ORGANISM: Artificial Sequence
<220> FEATURE:
<223> OTHER INFORMATION: Synthetic Oligonucleotide

<400> SEQUENCE: 38 gaucuuuc                                                       8

<210> SEQ ID NO 39
<211> LENGTH: 42
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 39
ggcagcgaua gacuguuaac uacagacggg aguccgcguu uc                42

<210> SEQ ID NO 40
<211> LENGTH: 48
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 40
agagauuuug ggaaggcuca ggacugccua cuaacccgau aagaauuc          48

<210> SEQ ID NO 41
<211> LENGTH: 49
<212> TYPE: RNA
<213> ORGANISM: Artificial Sequence

```
<220> FEATURE:
<223> OTHER INFORMATION: Description of Artificial Sequence: Synthetic
      Oligonucleotide

<400> SEQUENCE: 41 caucccagg cucuuccauc aagcaauuaa uacaaucaca accccuuc                    49

<210> SEQ ID NO 42
<211> LENGTH: 42
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 42
uuagcuccgu cagguaucca cagaucauug uucaauacau uc                         42

<210> SEQ ID NO 43
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 43
ccaugauaua ccgauauuaa cuuccgcguu gcacaagaau acacuguuc                  49

<210> SEQ ID NO 44
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 44
cgaaaucaua gcccacgguu gcaucacccg uucugaucau auacuuaaa                  49

<210> SEQ ID NO 45
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 45
cgucccacac ccuccgauuc cgaccaggac uggauacuua cacuuuuc                   49

<210> SEQ ID NO 46
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 46
cccccuucgc ccaaaacaua ucgcuucgac cuuccacacc cuaucauuc                  49

<210> SEQ ID NO 47
<211> LENGTH: 48
<212> TYPE: RNA
<213> ORGANISM: Artificial Sequence
<220> FEATURE:
```

<223> OTHER INFORMATION: Description of Artificial Sequence: Synthetic
Oligonucleotide

<400> SEQUENCE: 47
uuccuggaga cgccuauagu accuugcccc guaguaucug aucaauuc        48

<210> SEQ ID NO 48
<211> LENGTH: 55
<212> TYPE: RNA
<213> ORGANISM: Artificial Sequence
<220> FEATURE:
<223> OTHER INFORMATION: Description of Artificial Sequence: Synthetic
Oligonucleotide

<400> SEQUENCE: 48
uuaccuacaa aaagaaaaa gaauuaaacg gauuaagaag gggaaaaagu aguuc        55

<210> SEQ ID NO 49
<211> LENGTH: 49
<212> TYPE: RNA
<213> ORGANISM: Artificial Sequence
<220> FEATURE:
<223> OTHER INFORMATION: Description of Artificial Sequence: Synthetic
Oligonucleotide

<400> SEQUENCE: 49
auugagcccu ccgcccaaac ucacucucaa caaaccgcug gaacgcuuc        49

<210> SEQ ID NO 50
<211> LENGTH: 48
<212> TYPE: RNA
<213> ORGANISM: Artificial Sequence
<220> FEATURE:
<223> OTHER INFORMATION: Description of Artificial Sequence: Synthetic
Oligonucleotide

<400> SEQUENCE: 50
accgugcucu gugacaggac uuuacuuagg gauaaggguu gaaacuuc        48

<210> SEQ ID NO 51
<211> LENGTH: 29
<212> TYPE: RNA
<213> ORGANISM: Artificial Sequence
<220> FEATURE:
<223> OTHER INFORMATION: Description of Artificial Sequence: Synthetic
Oligonucleotide

<400> SEQUENCE: 51
cuggcaauaa acggcuauaa guaaaguuc        29

<210> SEQ ID NO 52
<211> LENGTH: 49
<212> TYPE: RNA
<213> ORGANISM: Artificial Sequence
<220> FEATURE:
<223> OTHER INFORMATION: Description of Artificial Sequence: Synthetic
Oligonucleotide

<400> SEQUENCE: 52
caaaauauac aaauaacaga cagaauacuu ugcaucaaua guuggauuc        49

<210> SEQ ID NO 53
<211> LENGTH: 48
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 53
cgcgcauaaa ccuaacgcgc uuuucucuag guugauuaaa cugguuc        48

<210> SEQ ID NO 54
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 54
agcagauguu gugauuaguu gaacaagguc cccaaacauu ggaggauuc        49

<210> SEQ ID NO 55
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 55
ccucauuaac cccgcugugc ccugcaucac uucucauagu ccgacacuc        49

<210> SEQ ID NO 56
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 56
caggucccac cgccccgcuc ccuuaucagc uuggaauacg uuuucauuc        49

<210> SEQ ID NO 57
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 57
ucaucucacc gccauaaucc ucaacauucu ccccacccga ucccguuc        49

<210> SEQ ID NO 58
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 58
gggagacaag aauaagcaug aaaccccaac ucuggcgcac auuccccgc caccaccgua    60 gaauacuucg acaggaggcu cacaacaggc        90

<210> SEQ ID NO 59
<211> LENGTH: 87
<212> TYPE: RNA
<213> ORGANISM: Artificial Sequence
<220> FEATURE:

```
<223> OTHER INFORMATION: Description of Artificial Sequence: Synthetic
      Oligonucleotide

<400> SEQUENCE: 59
gggagacaag aauaagcaug cccuucccua gaacgcaggc agcaguuacu cggagaaccc    60
uacccuucga caggaggcuc acaacag                                        87

<210> SEQ ID NO 60
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 60
gggagacaag aauaagcaug ggaccccaac uagcguguca uuguucgaau cgacugagau    60 uucgguucg acaggaggcu cacaacaggc                                      90

<210> SEQ ID NO 61
<211> LENGTH: 84
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 61
gggagacaag aauaagcaug agacugaucc aaauacgaca caaauacccg gcacuagacg    60
uucgacagga ggcucacaac aggc                                           84

<210> SEQ ID NO 62
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 62
gggagacaag aauaagcaug agcaucaauc uagacuagac ucagauuacc agcgaacuag    60
uguaucuucg acaggaggcu cacaacaggc                                     90

<210> SEQ ID NO 63
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 63
gggagacaag aauaagcaug uaauuccagc auaaaaaaga uagguacuau uaauacacga    60
ccagaauucg acaggaggcu cacaacaggc                                     90

<210> SEQ ID NO 64
<211> LENGTH: 80
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 64
```

```
gggagacaag aauaagcaug aucuacgcga ccacaaaauu auccgcgauu ugaauauucg      60
acaggaggcu cacaacaggc                                                 80
```

<210> SEQ ID NO 65
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 65

```
gggagacaag aauaagcaug ccccuugcgg uucccacauu aucucucugc uauccgaug       60 gcccgauucg acaggaggcu cacaacaggc                                      90
```

<210> SEQ ID NO 66
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 66

```
gggagacaag aauaagcaug agacauucuc uccgcccuca acuccgcccg cuccauccag      60
uucccugucg acaggaggcu cacaacaggc                                      90
```

<210> SEQ ID NO 67
<211> LENGTH: 88
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 67

```
gggagacaag aauaagcaug gccgauccau ccuccccacg accaucauga auccccaacag     60 gaacuucgac aggaggcuca caacaggc                                        88
```

<210> SEQ ID NO 68
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 68

```
gggagacaag aauaagcaug ggauaguucu gcguagcuua agagauguua aaucacaccc      60
acgccauucg acaggaggcu cacaacaggc                                      90
```

<210> SEQ ID NO 69
<211> LENGTH: 85
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 69

```
gggagacaag aauaagcaug gcuaucauac ccgagaccgc uauccccac cuuaauguuc       60 cuucgacagg aggcucacaa caggc                                           85
```

<210> SEQ ID NO 70
<211> LENGTH: 90
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 70
gggagacaag aauaagcaug agaccguaca ccucgcucgc cauccgacuu ugaauaagca    60
uagaccuucg acaggaggcu cacaacaggc                                     90

<210> SEQ ID NO 71
<211> LENGTH: 89
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 71
gggagacaag aauaagcaug agcgccaaua ugaccgcgac aucguuugaa uaguuccugg    60
ggaucuuucg acaggaggcu cacaacagg                                      89

<210> SEQ ID NO 72
<211> LENGTH: 90
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 72
gggagacaag aauaagcaug ccggauaagg ucguccguag uaccgguuaa cguaccagcc    60
uuacucuucg acaggaggcu cacaacaggc                                     90

<210> SEQ ID NO 73
<211> LENGTH: 90
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 73
gggagacaag aauaagcaug aucuaaagac agauuuaaua cuacccgucg uauccaacuc    60
ggaacggucg acaggaggcu cacaacaggc                                     90

<210> SEQ ID NO 74
<211> LENGTH: 90
<212> TYPE: RNA
<213> ORGANISM: Artificial Sequence
<220> FEATURE:
<223> OTHER INFORMATION: Description of Artificial Sequence: Synthetic Oligonucleotide

<400> SEQUENCE: 74
gggagacaag aauaagcaug uacguagaca agagauuucc agacccuguu acuaauacau    60
uucccguucg acaggaggcu cacaacaggc                                     90

<210> SEQ ID NO 75
<211> LENGTH: 50

```
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 75
gggagacaag aauaagcaug ccuacauucg acaggaggcu cacaacaggc           50

<210> SEQ ID NO 76
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 76
gggagacaag aauaagcaug cucugacaau ccugcaacaa uuacauucau uaacgggcua  60
auucauaucg acaggaggcu cacaacaggc                                  90

<210> SEQ ID NO 77
<211> LENGTH: 88
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 77
gggagacaag aauaagcaug auauguagua accccaauga uaaauaacua agaccgcaag  60
ucaguucgac aggaggcuca caacaggc                                    88

<210> SEQ ID NO 78
<211> LENGTH: 88
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 78
gggagacaag aauaagcaug ccacucccac acuuccuuaa uccgcgcuaa cacaccauau  60
guacuucgac aggaggcuca caacaggc                                    88

<210> SEQ ID NO 79
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 79
gggagacaag aauaagcaug cguuagcaga uacaucgaga uugcaaaguc caauacaguu  60
aauaaguucg acaggaggcu cacaacaggc                                  90

<210> SEQ ID NO 80
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide
```

```
<400> SEQUENCE: 80
gggagacaag aauaagcaug gagugcgucg ccacuacucc ucucauuacc ucuugcauuu    60
cacuauucga caggaggcuc acaacaggc                                     89

<210> SEQ ID NO 81
<211> LENGTH: 88
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 81
gggagacaag aauaagcaug ccccaccca cuauuagccg aacccgaacc ccaucuuacc    60
cggacccgac aggaggcuca caacaggc                                      88

<210> SEQ ID NO 82
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 82
gggagacaag aauaagcaug uucucugcgg ucuaggucac gauauacccg uuacauauca    60
uuccuguucg acaggaggcu cacaacaggc                                    90

<210> SEQ ID NO 83
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 83
gggagacaag aauaagcaug uacaaauccg cauauacacc caaccacacc caauccucuc    60
aguccauucg acaggaggcu cacaacaggc                                    90

<210> SEQ ID NO 84
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 84
gggagacaag aauaagcaug cccuagcaac auucuaugcg caaaccauag uuaugacuau    60
ugacucuucg acaggaggcu cacaacaggc                                    90

<210> SEQ ID NO 85
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 85
gggagacaag aauaagcaug cacaccggcu gaguaucugc cuguguaauc gaaacaacug    60
```

```
cgacauucga caggaggcuc acaacaggc                                     89

<210> SEQ ID NO 86
<211> LENGTH: 86
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 86
gggagacaag aauaagcaug ccgcacccgu accuccuucc ucucagguau ucacucacau    60
cauuucgaca ggaggcucac aacagg                                        86

<210> SEQ ID NO 87
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 87
gggagacaag aauaagcaug cacggaugac agcagaauaa cuccuacagu ccauauauaa    60
acgauuuucg acaggaggcu cacaacaggc                                    90

<210> SEQ ID NO 88
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 88
gggagacaag aauaagcaug caauuuaucg agacccagau aaccgauuua uacgcagacg    60
auaaguuucg acaggaggcu cacaacaggc                                    90

<210> SEQ ID NO 89
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 89
gggagacaag aauaagcaug agccccacau ccuacgccac ucacccacgc aucccgauug    60
aucaaauucg acaggaggcu cacaacaggc                                    90

<210> SEQ ID NO 90
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 90
gggagacaag aauaagcaug gggauagccg cacuucucac aggagucgag ucuuuugauc    60
ggucucuucg acaggaggcu cacaacaggc                                    90

<210> SEQ ID NO 91
```

```
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 91
gggagacaag aauaagcaug cgugcgccua ugaugagucu gguucacaua auuugcguua    60
guuaguuucg acaggaggcu cacaacaggc                                    90

<210> SEQ ID NO 92
<211> LENGTH: 49
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 92
gggagacaag aauaagcaug gaucuuucga caggaggcuc acaacaggc                49

<210> SEQ ID NO 93
<211> LENGTH: 83
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 93
gggagacaag aauaagcaug ggcagcgaua gacuguuaac uacagacggg aguccgcguu    60
ucgacaggag gcucacaaca ggc                                           83

<210> SEQ ID NO 94
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 94
gggagacaag aauaagcaug agagauuuug ggaaggcuca ggacugccua cuaacccgau    60
aagaauucga caggaggcuc acaacaggc                                     89

<210> SEQ ID NO 95
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 95
gggagacaag aauaagcaug cauccccagg cucuuccauc aagcaauuaa uacaaucaca    60 accccuucg acaggaggcu cacaacaggc                                     90

<210> SEQ ID NO 96
<211> LENGTH: 83
<212> TYPE: RNA
<213> ORGANISM: Artificial Sequence
<220> FEATURE:
<223> OTHER INFORMATION: Description of Artificial Sequence: Synthetic
      Oligonucleotide
```

<400> SEQUENCE: 96
gggagacaag aauaagcaug uuagcuccgu cagguaucca cagaucauug uucaauacau    60
ucgacaggag gcucacaaca ggc                                           83

<210> SEQ ID NO 97
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 97
gggagacaag aauaagcaug ccaugauaua ccgauauuaa cuuccgcguu gcacaagaau    60
acacuguucg acaggaggcu cacaacaggc                                    90

<210> SEQ ID NO 98
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 98
gggagacaag aauaagcaug cgaaaucaua gcccacgguu gcaucacccg uucugaucau    60
auacuuaaag uuaggaggcu cacaacaggc                                    90

<210> SEQ ID NO 99
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 99
gggagacaag aauaagcaug cgucccacac ccuccgauuc cgaccaggac uggauacuua    60 cacuuuucg acaggaggcu cacaacaggc                                     90

<210> SEQ ID NO 100
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 100
gggagacaag aauaagcaug cccccuucgc ccaaaacaua ucgcuucgac cuuccacacc    60
cuaucauucg acaggaggcu cacaacaggc                                    90

<210> SEQ ID NO 101
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 101
gggagacaag aauaagcaug uuccuggaga cgccuauagu accuugcccc guaguaucug    60

```
aucaauucga caggaggcuc acaacaggc                                            89
```

<210> SEQ ID NO 102
<211> LENGTH: 96
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 102

```
gggagacaag aauaagcaug uuaccuacaa aaaagaaaaa gaauuaaacg gauuaagaag         60
gggaaaaagu aguucgacag gaggcucaca acaggc                                    96
```

<210> SEQ ID NO 103
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 103

```
gggagacaag aauaagcaug auugagcccu ccgcccaaac ucacucucaa caaaccgcug         60
gaacgcuucg acaggaggcu cacaacaggc                                           90
```

<210> SEQ ID NO 104
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 104

```
gggagacaag aauaagcaug accgugcucu gugacaggac uuuacuuagg gauaaggguu         60
gaaacuucga caggaggcuc acaacaggc                                            89
```

<210> SEQ ID NO 105
<211> LENGTH: 70
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 105

```
gggagacaag aauaagcaug cuggcaauaa acggcuauaa guaaaguucg acaggaggcu         60
cacaacaggc                                                                 70
```

<210> SEQ ID NO 106
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 106

```
gggagacaag aauaagcaug caaaauauac aaauaacaga cagaauacuu ugcaucaaua         60
guuggauucg acaggaggcu cacaacaggc                                           90
```

```
<210> SEQ ID NO 107
<211> LENGTH: 89
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 107
gggagacaag aauaagcaug cgcgcauaaa ccuaacgcgc uuuucucuag guugauuaaa      60 cugguucga caggaggcuc acaacaggc                                        89

<210> SEQ ID NO 108
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 108
gggagacaag aauaagcaug agcagauguu gugauuaguu gaacaagguc cccaaacauu      60
ggaggauucg acaggaggcu cacaacaggc                                      90

<210> SEQ ID NO 109
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 109
gggagacaag aauaagcaug ccucauuaac cccgcugugc ccugcaucac uucucauagu      60
ccgacacucg acaggaggcu cacaacaggc                                      90

<210> SEQ ID NO 110
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 110
gggagacaag aauaagcaug caggucccac cgccccgcuc ccuuaucagc uuggaauacg      60
uuuucauucg acaggaggcu cacaacaggc                                      90

<210> SEQ ID NO 111
<211> LENGTH: 90
<212> TYPE: RNA
<213> ORGANISM: Artificial Sequence
<220> FEATURE:
<223> OTHER INFORMATION: Description of Artificial Sequence: Synthetic
      Oligonucleotide

<400> SEQUENCE: 111
gggagacaag aauaagcaug ucaucucacc gccauaaucc ucaacauucu ccccacccga      60
uucccguucg acaggaggcu cacaacaggc                                      90

<210> SEQ ID NO 112
<211> LENGTH: 90
<212> TYPE: DNA
<213> ORGANISM: Artificial Sequence
```

```
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (22)..(70)
<223> OTHER INFORMATION: n = a, c, t, or g

<400> SEQUENCE: 112
gcctgttgtg agcctcctaa cnnnnnnnnn nnnnnnnnnn nnnnnnnnnn nnnnnnnnnn       60
nnnnnnnnnn catgcttatt cttgtctccc                                       90

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 113
gcctgttgtg agcctcctgt cgaa                                             24

<210> SEQ ID NO 114
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 114
taatacgact cactataggg agacaagaat aagcatg                               37

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 115
aagctgtcct ccgagtgttg tccg                                             24

<210> SEQ ID NO 116
<211> LENGTH: 37
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 116
attatgctga gtgatatccc tctgttctta ttcgtac                               37

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 117
aagctgtcct ccgagtgttg tccg                                             24
```

<210> SEQ ID NO 118
<211> LENGTH: 37
<212> TYPE: DNA
<213> ORGANISM: Artificial Sequence
<220> FEATURE:
<223> OTHER INFORMATION: Description of Artificial Sequence: Synthetic
     Oligonucleotide

<400> SEQUENCE: 118
attatgctga gtgatatccc tctgttctta ttcgtac                              37

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
     Oligonucleotide

<400> SEQUENCE: 119
cccagtcacg acgttgtaaa acg                                             23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
     Oligonucleotide

<400> SEQUENCE: 120
agcggataac aatttcacac agg                                             23

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
     Oligonucleotide

<400> SEQUENCE: 121
aagctgtcct ccgagtgttg tccg                                            24

<210> SEQ ID NO 122
<211> LENGTH: 37
<212> TYPE: DNA
<213> ORGANISM: Artificial Sequence
<220> FEATURE:
<223> OTHER INFORMATION: Description of Artificial Sequence: Synthetic
     Oligonucleotide

<400> SEQUENCE: 122
attatgctga gtgatatccc tctgttctta ttcgtac                              37

<210> SEQ ID NO 123
<211> LENGTH: 98
<212> TYPE: RNA
<213> ORGANISM: Artificial Sequence
<220> FEATURE:
<223> OTHER INFORMATION: Description of Artificial Sequence: Synthetic
     Oligonucleotide
<220> FEATURE:
<221> NAME/KEY: misc_feature
<222> LOCATION: (21)..(75)
<223> OTHER INFORMATION: a, c, u, or g, and this region may encompass 20
     to 55 nucleotides

```
<400> SEQUENCE: 123
gggagacaag aauaagcaug nnnnnnnnnn nnnnnnnnnn nnnnnnnnnn nnnnnnnnnn       60
nnnnnnnnnn nnnnnuucga caggaggcuc acaacagg                               98

<210> SEQ ID NO 124
<211> LENGTH: 97
<212> TYPE: RNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (21)..(75)
<223> OTHER INFORMATION: a, c, u, or g, and this region may encompass 20
      to 55 nucleotides

<400> SEQUENCE: 124
gggagacaag aauaagcaug nnnnnnnnnn nnnnnnnnnn nnnnnnnnnn nnnnnnnnnn       60
nnnnnnnnnn nnnnnuucga caggaggcuc acaacag                                97
```

CD7 RECEPTOR APTAMERS

FIELD OF THE INVENTION

The present invention relates to nucleic acid aptamers which can specifically recognize, bind to and internalize into cells expressing the lymphocyte-specific CD7 receptor. Thus, this invention can be used, amongst others, to diagnose and treat diseases and infections associated with lymphocytes.

BACKGROUND OF THE INVENTION

The specific delivery of molecules to target cells has eluded medical science for decades while the need for such tools has grown. There are a number of mechanisms to deliver molecules into cells (eg. liposomes, viral vectors and polyplex reagents) but these are limited in a number of ways, most notably their inability to selectively deliver molecules in a heterogenous cell population, as would be found in human organs and tissues. In order to deliver molecules safely and effectively, an alternative medical tool needs to be developed that is not only non-immunogenic but capable of selectively identifying target cells in a mixed population. Aptamers have shown potential to fulfil this need.

Aptamers are artificial nucleic acid molecules that can be isolated to bind to an array of macromolecules (Reviewed in Khati (2010)). The selection and design of highly selective aptamers with high affinity to their target has lead to the development of a variety of aptamers capable of binding an array of molecules. The pioneering work by the Gold (Tuerk, 199) and Szostak (Ellington, 1990) groups, identified an in vitro method for the selection of aptamers specific to organic dyes and T4 DNA polymerases, respectively. This method, called Systematic Evolution of Ligands by Exponential enrichment (SELEX), has been adapted to streamline the selection process of aptamers. Aptamers have been developed that specifically target the HIV surface glycoprotein gp120 and inhibit viral entry (Khati, 2003; Zhou, 2009) Making use of their target specificity, these aptamers have been identified as delivery vehicles for targeted delivery of Dicer substrate siRNA to specific cells (Zhou, 2009; McNamara, 2006). Short interfering RNA (siRNA) are small RNA molecules that act with a number of accessory molecules to post transcriptionally silence target genes. These powerful silencing molecules are only active once in the cytoplasm and are not able to internalise efficiently alone. As such, they require active delivery into cells. Aptamers have been identified as efficient delivery agents for not only siRNA but nanoparticles as well (Dhar, 2008). Recently, an anti-gp120 aptamer and anti-tat/rev siRNA chimera was shown to reduce viral replication and helper CD4⁺ T cell depletion in humanized mice (Neff, 2011). The chimera did not elicit an interferon response, unlike what has been seen with liposome or polyplex regent mediated delivery of siRNA (Zhou, 2009).

Current HIV targeted siRNA-aptamer conjugates are directed against infected lymphocytes by targeting HIV glycoprotein (gp120) residues on the infected cell membrane (Zhou, 2009). The CD4 receptor in lymphocytes/monocytes has also been used to target aptamer-siRNA chimeras for internalization (Wheeler, 2011). However, the CD4 aptamer was not selected for internalization and is inefficient, working in the 1-4 µM range ex vivo.

CD7 is a pan-leucocytic receptor expressed on progenitors of T and B lymphocytes, natural killer cells and dendritic cells (Hao, 2001; Sempowki, 1999) that plays an accessory role in T cell activation (Lazarovits, 1994; Stillwell, 2011) and persists on the surface of mature CD4⁺ cells (Cotta, 2006; Lobac, 1985). CD7 has been widely studied as a target for delivery of cytotoxic molecules for leukaemia and lymphoma treatment (Peipp, 2002; Bremmer, 2006; Franker, 1997; Vallera, 1996; Waurzyniak, 1997). Previously it was shown using single-chained monoclonal antibodies conjugated to siRNAs that by targeting CD7 for delivery of HIV therapeutics (siRNAs), there is a protective inhibition of viral infection (Kumar, 2008). The study by Kumar (2008) used an antibody for targeting drug delivery, which required an elaborate and complicated conjugation method for attaching the effector molecule.

There is therefore still a need for a method of delivering a target molecule to cells which express a CD7 cell-surface receptor which overcomes at least some of the problems described above.

SUMMARY OF THE INVENTION

According to a first embodiment of the invention, there is provided an aptamer molecule not more than 100 nucleotides in length comprising a nucleotide sequence which is at least 80% identical to the sequence 5' GGGAGA-CAAGAAUAAGCAUG-$R_1$-UUCGACAGGAGGCUCA-CAACAGGC3' (SEQ ID NO: 3),
wherein $R_1$ is $n_x$ where each n represents any nucleotide and x is an integer from 20 to 55, and
wherein the aptamer molecule is capable of selectively binding to a cell expressing a CD7 receptor.

The aptamer molecule may have a nucleotide sequence which is at least 80% identical to the sequence 5' GGGA-GACAAGAAUAAGCAUG-$R_1$-UUCGACAGGAGGCU-CACAACAGG 3' (SEQ ID NO: 123) or 5' GGGAGA-CAAGAAUAAGCAUG-$R_1$-UUCGACAGGAGGCUCACAACAG 3' (SEQ ID NO: 124).

X may more preferably be an integer from 29 to 55.and even more preferably an integer from 39 to 55. Even more preferably, x may be an integer from 39 to 49

$R_1$ may have a nucleotide sequence of any one of SEQ ID NOS: 4-57.

The aptamer molecule may comprise at least 68 nucleotides, and more preferably at least 80 nucleotides, such as from 84 to 90 nucleotides.

The aptamer molecule may be at least 85%, at least 90%, at least 95% or 100% identical to SEQ ID NO: 3.

The aptamer molecule may comprise the nucleic acid sequence set out in any one of SEQ ID NOS: 58-111.

One or more of the nucleotide bases of the molecule may have been modified.

The aptamer molecule may be capable of being internalised into a CD7-expressing cell.

The aptamer molecule may be used to deliver a therapeutic or diagnostic molecule to a cell having a CD7 receptor.

According to a second embodiment of the invention, there is provided a conjugate comprising the aptamer molecule as described above linked to a therapeutic or diagnostic molecule.

According to a third embodiment of the invention, there is provided a pharmaceutical composition comprising an aptamer molecule or conjugate as described above and a pharmaceutically acceptable carrier.

According to a fourth embodiment of the invention, there is provided a method for delivering a therapeutic or diagnostic molecule to a cell having a CD7 receptor, the method comprising contacting the cell with an aptamer or conjugate as described above.

According to a fifth embodiment of the invention, there is provided a method for detecting a CD7-expressing cell, the method comprising contacting cells with an aptamer or conjugate as described above and detecting when the aptamer or conjugate binds to or is internalised by a cell.

DETAILED DESCRIPTION OF THE INVENTION

Figure 1:
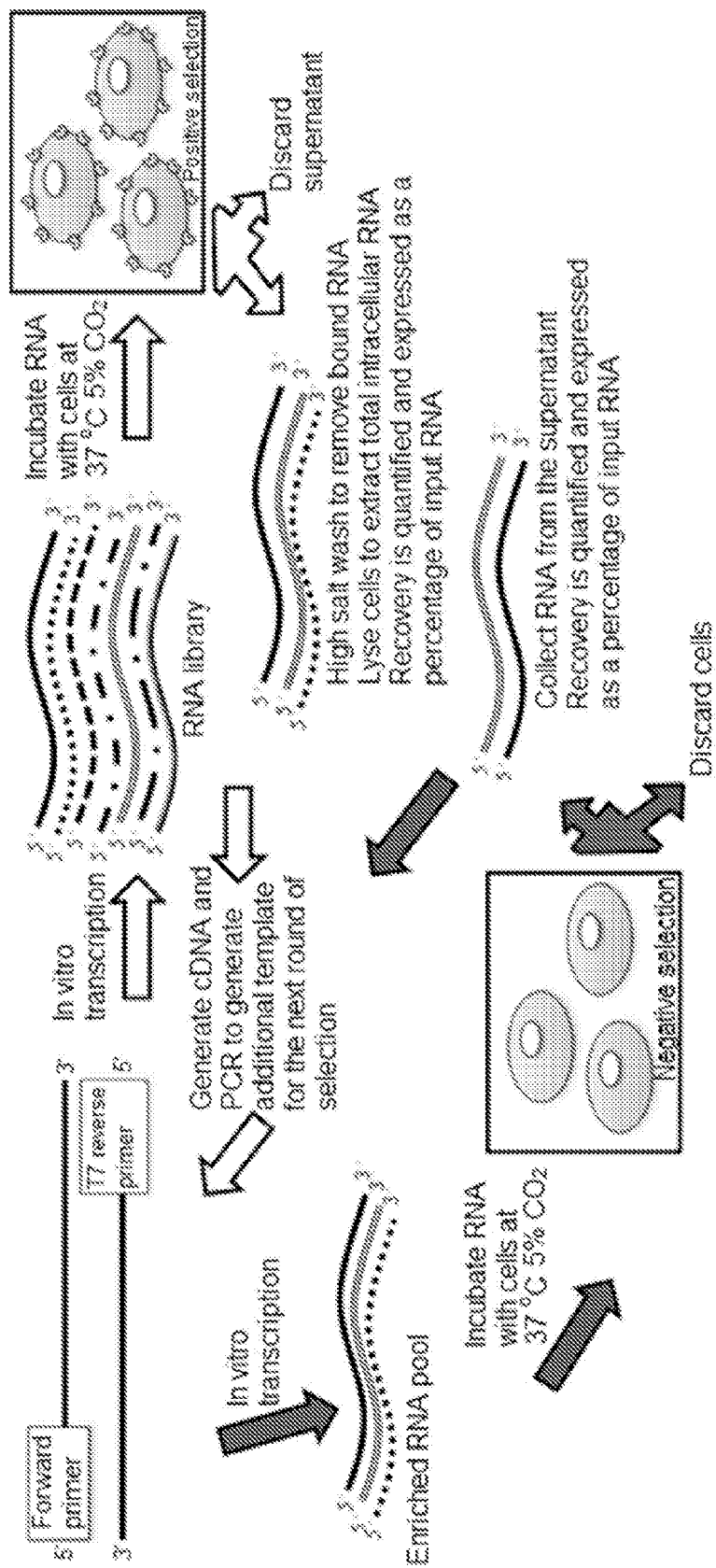
FIG. 1: Whole cell SELEX protocol to select internalising aptamers. Selection of internalising aptamers using whole cells. Positive selection using CD7-HeLa cells started with the transcription of the dsDNA library into 2' fluorinated pyrimidine RNA library. The RNA was incubated with CD7-HeLa cells at 37° C. after which the supernatant was discarded and bound RNA washed off the cells. The internalised RNA was recovered by lysing the cells and the recovered RNA was reverse transcribed into cDNA and amplified by PCR before transcribing into RNA for use in the next round of selection. The negative selection in HeLa cells was used to remove any non-specifically internalised RNA. For this, after incubation with the enriched pool of RNA, cells were discarded and the supernatant was retained to generate more template. The selection was continued until the recovery from each round reached a plateau.

The invention provides nucleic acid aptamers which bind specifically to cells or tissues expressing a CD7 cell-surface receptor. The aptamers comprise a molecule with a nucleic acid sequence which is at least 80% identical to the nucleic acid sequence 5'-GGGAGACAAGAAUAAGCAUG-R$_1$-UUCGACAGGAGGCUCACAACAGGC-3' (SEQ ID NO: 3), wherein R$_1$ is n$_x$, where each n represents any nucleotide and x is an integer from 29 to 55.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

As used herein, the term "nucleic acid aptamer" refers to a small single-stranded oligonucleotide that can recognize specifically to its target with high affinity.

As used herein, the phrase "nucleic acid sequence which is at least 80%/85%/90%/95% identical to . . . " refers to a nucleic acid sequence which comprises an addition, deletion or substitution of one to several nucleotides relative to the reference sequence.

The applicant has shown that aptamers which have the nucleic acid sequence 5'-GGGAGA-CAAGAAUAAGCAUG-R$_1$-UUCGACAGGAGGCUCA-CAACAGGC-3' (SEQ ID NO: 3), or modifications thereof, are capable of binding to and/or being internalised into cells expressing the CD7 receptor. The molecules having SEQ ID NOS: 58 to 111 are specific examples of such aptamers.

The aptamer can have a sequence which is at least 85%, 90% or 95% identical to SEQ ID NO: 3, provided, however, that the aptamer is capable of binding to or being internalised into a cell or tissue expressing the CD7 receptor. The aptamer can even be identical to SEQ ID NO: 3. The modifications which give rise to the at least 80%, 85%, 90% or 95% identity to SEQ ID NO: 3 are generally modifications of the nucleotides flanking R$_1$ on either it's 5' end or 3' end. Thus, the nucleotides flanking the 5' end of R$_1$ can have a sequence which is at least 80%, 85%, 90% or 95% identical to the sequence GGGAGA-CAAGAAUAAGCAUG (SEQ ID NO: 1), and the nucleotides flanking the 3' end of R$_1$ can have sequence which is at least 80%, 90% or 95% identical to the sequence UUC-GACAGGAGGCUCACAACAGGC (SEQ ID NO: 2).

The aptamers of the invention comprise less than 100 nucleotides, and typically comprise 90 or fewer nucleotides. The aptamers comprise at least 68 nucleotides, more typically comprising 80 or more nucleotides. The 5'-flanking region preferably comprises 20 nucleotides, and the 3'-flanking region preferably comprises from 19 to 24 nucleotides. Although the 5'-end of the 3'-flanking region of most of the aptamers begins with the nucleotides "AC", there are also aptamers where this section begins with the nucleotides "UU". Some of the aptamers identified by the applicant do not include the terminal C or GC at the 3' end of SEQ ID NO: 2. R$_1$ can have from 20 to 55 nucleotides, and more particularly at least 29 nucleotides or at least 39 nucleotides, with most of the aptamers having from 39 to 49 nucleotides in this intermediate region, and even more particularly from 47 to 49 nucleotides. The last 3 nucleotides of R$_1$ are most commonly UUC, although some aptamers also have the nucleotides GUC, AUC, CCC or AAA in these positions. SEQ ID NOS: 4 to 57 are specific examples of suitable intermediate regions.

One or more sugars or bases of the nucleotides of the aptamer may be modified. For example, modified nucleotides include nucleotides having sugars which are covalently attached to low molecular weight organic groups other than a hydroxyl group at the 3' position and other than a phosphate group at the 5' position. The modifications also include 2'0-methyl modification, 2'-fluoro modification or phosphorylation. Additional modifications to the nucleotides in the aptamer include large molecular weight conjugates like pegylation, lipid-based modifications (e.g. cholesterol) or nanoparticles (e.g. PEI or chitosan) to improve the pharmacokinetic/dynamic profile of the chimera. In the examples which follow, the aptamers include 2'F-C and 2'F-U modifications. All of the C and U bases can be 2'F modified.

The aptamers can be used to target a cell expressing a CD receptor in vivo, ex vivo or in vitro. The aptamers can also be used to target a tissue immobilised on a cell expressing a CD receptor.

In one embodiment of the invention, the aptamers can be ligated or conjugated to therapeutic molecules, such as nanoparticles, RNA drugs, siRNA, synthetically or biologically produced drugs and so forth, to form a conjugate or chimera. These conjugates or chimeras can be used for delivery of therapeutic treatments to cells or tissues expressing a CD7 receptor. Cells or tissues which express the CD7 receptor include lymphocytes, thymocytes, some T cells, monocytes, natural killer cells, and hematopoietic stem cells. HIV infection is just one condition which could be treated using the aptamers of the present invention, but any condition or disease which affects lymphocytes could be treated in the same manner, such as leukaemia, lymphoma (e.g. T-cell acute lymphoblastic lymphoma and acute non-lymphocytic lymphoma) and mycosis fungoides.

Chemistries that can be used to link molecules to the aptamer are known in the art, such as disulfide linkages, amino linkages, covalent linkages, etc. Additional linkages and modifications can be found on the world-wide-web at trilinkbiotech.com/products/oligo/oligo_modifications.asp. The molecules can be linked to the aptamers on either or both of the 5' and 3' ends of the aptamer, or can even be linked intermolecularly.

In another embodiment, the aptamers can be used to bind to ligands for diagnostic purposes in a similar manner to antibodies, e.g. as a probe, in immunofluorescence, or an ELISA-type assay.

In a further embodiment, the aptamers can be used as diagnostic or detection molecules. For example, the aptamer could be linked to a fluorescent dye and/or to a magnetic bead.

The invention will now be described in more detail by way of the following non-limiting examples.

EXAMPLES

Materials and Methods
Selection of Internalising Anti-CD7 Aptamers by Whole Cell SELEX Aptamer selection made use of a 90 nucleotide ssDNA library with a 49 nucleotide random region (5' GCCTGTT-GTGAGCCTCCTAAC(N49)CATGCTTATTCTT-GTCTCCC 3' (SEQ ID NO: 112)) custom synthesized by Integrated DNA Technologies (CA, USA). The single stranded DNA was made double stranded by PCR with the reverse primer containing the T7 polymerase promotor region (Forward primer: 5' GCCTGTTGTGAGCCTCCT-GTCGAA 3' (SEQ ID NO: 113) and T7 Reverse primer 5' TAATACGACTCACTATAGGGAGACAAGAATAAG-CATG 3' (SEQ ID NO: 114), T7 promotor region underlined). The double stranded DNA was transcribed to RNA to generate the RNA library used in the selection. The RNA library was transcribed to include 2'fluorinated pyrimidines (2'F) to increase RNA stability and prevent nuclease degradation.

A modified whole cell SELEX (Thiel, 2012) was used to generate RNA aptamers capable of internalising cells using the human surface CD7 receptor. The selection included six rounds of positive selection in CD7-HeLa cells and a negative selection using un-transfected HeLa cells. Each round of selection was put into un-transfected HeLa cells to detect any background non-specific internalising aptamer selection (FIG. 1). Positive selection in CD7-HeLa was achieved by growing cells in a six well dish to 90% confluency for 48 hours. The growth media was removed from each well and cells were washed with 2 ml PBS. Non-specific RNA binding sites on the cells' surface were blocked by the addition of 100 µg/ml yeast tRNA in 1× HMCKN at 37° C. for 20 minutes. The block was discarded before incubating the cells with 100 nM re-folded 2' fluorinated RNA library in 1× HMCKN at 37° C. for one hour. RNA was refolded by heating to 95° C. for three minutes followed by incubation at room temperature for ten minutes in 1× HMCKN. The unbound RNA was discarded and the cells washed with 2 ml ice cold 0.5 M NaCl in PBS to remove any bound RNA on the cell surfaces. After washing, cells were solubilised using 1 ml Trizol (Sigma-Aldrich, MO, USA) per well and transferred into clean tubes. The samples were vortexed for 40 seconds to shear DNA before adding 200 µl of chloroform to each sample and vortexing again for 30 seconds. The samples were centrifuged at maximum speed for 15 minutes after which the aqueous phase was transferred to a clean tube. To degrade and remove the cellular RNA and the blocking yeast tRNA, RNAse A (Fermentas, Thermo Fisher Scientific Inc., MA, USA) was added to each sample at a final concentration of 100 µg/ml and incubated at 37° C. for 30 minutes. The samples were then phenol: chloroform: isoamyl alcohol extracted and centrifuged at maximum speed at room temperature for ten minutes. The aqueous phase was retained to which chloroform was added, the samples were centrifuged and the aqueous phase retained. Following this, 1 vol isopropanol and 0.1 vol sodium acetate was added to each sample which was incubated overnight at −80° C. to precipitate the RNA. The RNA was then pelleted by centrifugation at 4° C. after which the supernatant was discarded. The pellets were washed with ice-cold 70% ethanol and left to air dry. Pellets were re-suspended in nuclease free water and passed through a NucAway™ Spin Columns (Ambion, NY, USA) to remove the free nucleotides before being quantified by NanoDrop-spectrophotometer at $A_{260}$. Columns were hydrated using 650 µl nuclease free water for five minutes at room temperature. The columns were placed in collection tubes and spun for two minutes at 750×g to remove excess interstitial fluid. The flow through was discarded and the RNA recovery was added directly to the centre of the gel bed. The columns were placed into clean collection tubes and spun for two minutes at 750×g. The spin columns were then discarded as the flow through contained the clean RNA ready for use. The recovered RNA was expressed as a percentage of the added RNA and was used to track the enrichment per round of selection. The recovered RNA was reverse transcribed into cDNA using a Verso cDNA Synthesis kit (Thermo Fisher Scientific Inc., MA, USA) to generate a template for PCR amplification of the DNA for sufficient material to produce RNA for the next round of selection. The RNA (1 ng) was combined with 2.5 µM forward primer and incubated at 65° C. for ten minutes before chilling on ice. While on ice, the remaining reaction reagents were added in order: 1× cDNA synthesis buffer, 500 µM dNTP, 1.1 µl Verso Enzyme mix made up in water (reagents supplied with the kit). As an extra precaution, 40 units RNAse inhibitor (Fermentas, Thermo Fisher Scientific Inc., MA, USA) was added to the reaction mix and was incubated at 45° C. for 30 minutes. The reverse transcription enzyme was deactivated before PCR by incubating the reaction at 85° C. for five minutes. The resulting cDNA was used as the template for a mutagenic PCR (high salt concentration) to generate DNA for transcription to RNA for the next round of selection. The increased magnesium concentration helps to stabilise non-complimentary base pairs Cadwell, 1994). The mutagenic PCR contained: 1× Taq buffer (Promega, WI, USA), 7.5 mM $MgCl_2$ (Promega, WI, USA), 0.2 mM dNTPs (Fermentas, Thermo Fisher Scientific Inc., MA, USA), 1 µM forward primer (3' GCCTGTTGT-GAGCCTCCTGTCGAA 5' (SEQ ID NO: 115)) and 1 µM reverse primer (3' CATGCTTATTCTTGTCTCCCTATAGT-GAGTCGTATTA 5' (SEQ ID NO: 116)) (Integrated DNA Technologies, CA, USA), 1 U Go Taq Polymerase (Promega, WI, USA) and 100 ng DNA. The reaction was performed with the following parameters: an initial denaturation step at 93° C. for one minutes followed by cycles of 93° C. for 30 seconds for denaturation, 54° C. for 30 seconds for annealing and 72° C. for one minute for extension. A final extension of ten minutes at 72° C. was included after the last cycle. The PCR was optimised for optimal cycle number to generate a single band of PCR product at each round of selection. The PCR product was cleaned by centrifugation using a PCR purification kit (Promega, WI, USA) according to manufacturer's specifications. Briefly, the PCR product was prepared for clean up by adding equal volume Membrane Binding Solution (provided in the kit) and added to an SV mini-column inside a Collection Tube and incubated for one minute. The SV mini-column assembly was centrifuged at 16 000×g for one minute and the flow through was discarded. The SV mini-column was washed with 700 µl Membrane Wash Solution (previously diluted with 95 ethanol) and again centrifuged at 16 000×g for one minute. Flow through was again discarded and the column washed with 500 µl of Membrane Wash Solution and centrifuged at 16 000×g for five minutes. The flow through was discarded and the assembly centrifuged at 16 000×g for one minute to evaporate remaining ethanol. The SV mini-column was transferred to a 1.5 ml microfuge tube the cleaned product was eluted in 50 µl nuclease-free water by centrifugation at 16 000×g for one minute.

DNA was quantified using a Nano drop-spectrophotometer at $A_{260}$. The 260:280 ratio was used as an indication of DNA purity. Fractions of the clean DNA were resolved on a 2.5% (w/v) agarose gel stained with ethidium bromide (Merck, Darmstadt, Germany) in 1× TBE running buffer. A Mass Ruler Low Range DNA Ladder (Fermentas, Thermo Fisher Scientific Inc., MA, USA) was used for DNA sizing and quantification by Molecular Imager Chemidoc XRS+ Imaging System (BIORAD, CA, USA). Purified DNA was used for RNA aptamer production by in vitro transcription. In vitro transcription followed the protocol previously described by Khati et al. (2003). Briefly, 100 µl reaction mixture contained: 1.5 ng DNA, 1× transcription buffer (New England Biolabs® Inc., MA, USA) 2 mM spermidine, 1 mM rATP, 1 mM rGTP, 1.5 mM 2'F CTP, 1.5 mM 2'F UTP (Fermentas, Thermo Fisher Scientific Inc., MA, USA), 2 U T7 RNA Polymerase (New England Biolabs® Inc., MA, USA). Transcription reaction was incubated overnight at 37° C. The reaction was stopped with the addition of 1 U RNAse free DNAse I in 1× Reaction Buffer (Fermentas, Thermo Fisher Scientific Inc., MA, USA) and incubated at 37° C. for 25 minutes. RNA aptamers were purified from low molecular weight contaminants using NucAway™ Spin Columns (Ambion, NY, USA) as previously described. RNA was quantified by spectrophotometry at $A_{260}$ and was then used for subsequent rounds of selection.

Figure 2:
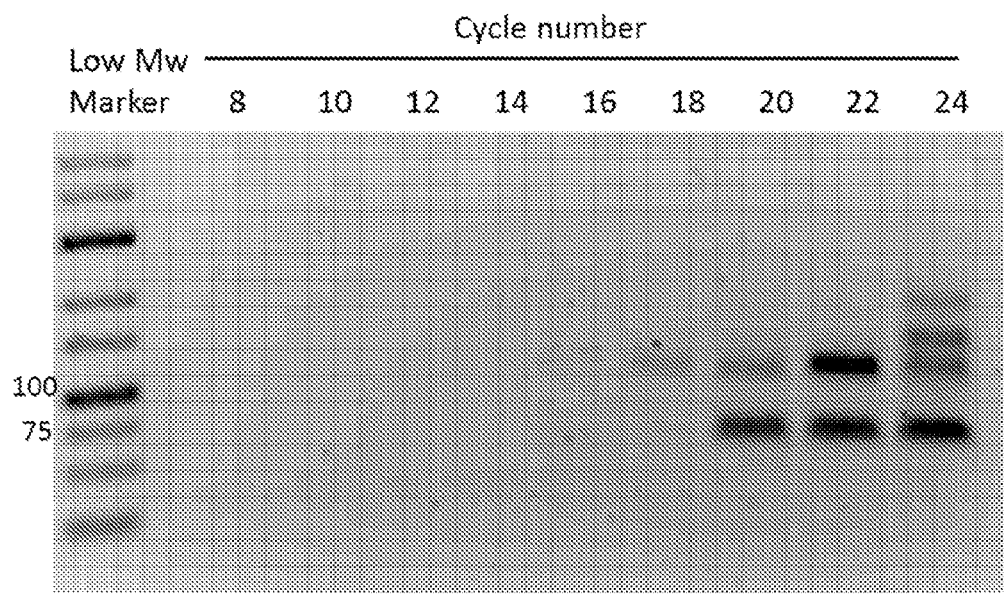
FIG. 2: Pilot PCR to optimise cycle number for SELEX DNA amplification. PCR amplification of DNA at each round of selection was optimised for cycle number. Over amplification of the template was seen after 24 cycles while no product was generated before 16 cycles. At 20 cycles primer dimer amplification can be seen as a lower band aligning with 75 nucleotides. The band of interest at 100 nucleotides was evident from 16 cycles. The optimal cycle number produced the band of interest without any aberrant bands.

Negative selection used un-transfected HeLa cells as these were the backbone for the production of CD7-HeLa cells used for the positive selection and as such will include all surface receptors excluding the target CD7. Cells were grown to 90% confluency for 48 hours. The growth media was removed from each well and cells were washed with 2 ml PBS. Non-specific RNA binding sites on the cells' surface were blocked by the addition of 100 µg/ml yeast tRNA in 1× HMCKN at 37° C. for 20 minutes. The block was discarded before incubating the cells with 100 nM re-folded 2' F enriched RNA in 1× HMCKN at 37° C. for one hour. After incubation the cells were discarded and the RNA from the supernatant was collected and quantified (FIG. 2-1). As a negative background control, the recovery from each round was incubated with HeLa cells and the RNA from within the cells was quantified. This controlled served to confirm that the enrichment seen in CD7-HeLa cells was specific to the receptor positive cells.

Cloning and Sequencing of RNA Anti-CD7 Aptamers

The recovery from the final round of selection (round 6) was reverse transcribed to cDNA and amplified by PCR to generate the template for cloning. A non-mutagenic PCR with reduced magnesium conditions was used for the final amplification. Each 100 µl reaction mixture contained 1× Taq buffer (Promega, WI, USA), 1 mM $MgCl_2$ (Promega, WI, USA), 0.2 mM dNTPs (Fermentas, Thermo Fisher Scientific Inc., MA, USA), 1 µM forward primer (3' GCCT-GTTGTGAGCCTCCTGTCGAA 5' (SEQ ID NO: 117)) and 1 µM reverse primer (3'CATGCTTATTCTTGTCTC-CCTATAGTGAGTCGTATTA 5' (SEQ ID NO: 118)) (Integrated DNA Technologies, CA, USA), 1 U Go Taq Polymerase (Promega, WI, USA) and 100 ng DNA. An eighteen cycle PCR was performed with the following parameters: an initial denaturation step at 93° C. for one minute followed by cycles of 93° C. for 30 seconds for denaturation, 54° C. for 30 seconds for annealing and 72° C. for one minute for extension. A final extension of ten minutes at 72° C. was included after the last cycle.

The PCR product was ligated into a pGEM-T Easy® vector (Promega, WI, USA) according to manufacturer's instructions. Ligation was done by adding 100 ng of double stranded PCR product to 50 ng of pGEM-T Easy® vector and 3 units of T4 enzyme. The reaction was incubated at 37° C. for one hour. For the transformation, frozen TOP10 highly efficient chemically competent cells (Novagen, Merck, Darmstadt, Germany) were thawed on ice. Two microliters of the ligation reaction was added to 50 µl competent cells and incubated on ice for 20 minutes. A no vector cell control was included and treated the same as the transformed cells. After incubation, the cells were heat shocked at 42° C. for 45 seconds and immediately placed on ice for two minutes. To each vial of cells, 950 µl of SOC (Super Optimal broth with Catabolite repression, Invitrogen, CA, USA) was added and the samples were incubated at 37° C. for 90 minutes shaking at 200 rpm. After incubation, 25 µl from each transformant was spread over pre-warmed selective nutrient agar plates (Sigma-Aldrich, MO, USA) supplemented with 100 µg/ml ampicillin antibiotic (Sigma-Aldrich, MO, USA) and incubated over night at 37° C. Ninety six colonies were picked and spread onto two plates. One plate was used for colony PCR screening using M13 primers; pUC/M13 primer forward: 5' CCCAGTCAC-GACGTTGTAAAACG 3' (SEQ ID NO: 119) and pUC/M13 reverse primer: 5' AGCGGATAACAATTTCACACAGG 3' (SEQ ID NO: 120) (Integrated DNA Technologies, CA, USA) and to prepare overnight cultures for glycerol stocks. The other plate was sent to Inqaba Biotech (South Africa) for sequencing with the pUC/M13 forward and reverse primers. Sequence analysis and alignments were performed using BioEdit (Hall, 1999). The full aptamer sequences were analysed using CLUSTAL W multiple alignment application in BioEdit V7.1.3.0 software (Hall, 1999). A full multiple alignment was generated by bootstrapped neighbour joining tree with the bootstrap value set to 1000. Default gap penalties for gap opening and gap extension were used. The aligned sequences were assessed for conserved motifs and were used to generate a Neighbour tree and was analysed for sequence similarity between aptamers.

Anti-CD7 Aptamer Production by PCR and in Vitro Transcription

Each selected aptamer was generated by in vitro transcription of double stranded DNA. For this, plasmid DNA of each aptamer was amplified using polymerase chain reaction (PCR). Each 100 µl reaction mixture contained 1× Taq buffer (Promega, WI, USA), 1 mM $MgCl_2$ (Promega, WI, USA), 0.2 mM dNTPs (Fermentas, Thermo Fisher Scientific Inc., MA, USA), forward primer (3'GCCTGTTGTGAGCCTC-CTGTCGAA 5' (SEQ ID NO: 121)) and reverse primer (3' CATGCTTATTCTTGTCTCCCTATAGTGAGTCGTATTA 5' (SEQ ID NO: 122)) (Integrated DNA Technologies, CA, USA), 1 U Go Taq Polymerase (Promega, WI, USA) and 100 ng DNA. An eighteen cycle PCR was performed with the following parameters: 93° C. for 30 seconds for denaturation, 54° C. for 30 seconds for annealing and 72° C. for one minute for extension. A final extension of 10 minutes at 72° C. was included in the last cycle.

The PCR product was cleaned by centrifugation using a PCR purification kit (Promega, WI, USA) according to manufacturer's specifications. Briefly, the PCR product was prepared for clean up by adding equal volume membrane binding solution (provided in the kit) and added to an SV mini-column inside a collection tube and incubated for one minute. The SV mini-column assembly was centrifuged at 16 000×g for one minute and the flow through was discarded. The SV mini-column was then washed with 700 µl membrane wash solution (previously diluted with 95% ethanol) and again centrifuged at 16 000×g for one minute. Flow through was again discarded and the column washed with 500 µl of membrane wash solution and centrifuged at 16 000×g for five minutes. The flow through was discarded and the assembly centrifuged at 16 000×g for one minute to evaporate remaining ethanol. The SV mini-column was transferred to a 1.5 ml microfuge tube the cleaned PCR product was eluted in nuclease-free water by centrifugation at 16 000×g for one minute.

DNA was quantified using a NanoDrop 1000 spectrophotometer (Thermo Fisher Scientific Inc., MA, USA) at $A_{260}$. The 260:280 ratio was used as an indication of DNA purity with an expected ratio of 1.8 for pure DNA. Fractions of the clean DNA were resolved on a 2.5% agarose gel stained with ethidium bromide and run in 1× TBE running buffer. A MassRuler Low Range DNA Ladder (Fermentas, Thermo Fisher Scientific Inc., MA, USA) was used for DNA sizing and quantification by Molecular Imager Chemidoc XRS+ Imaging System (BIORAD, CA, USA). Purified DNA was used for RNA aptamer production by in vitro transcription. In vitro transcription followed the protocol previously described by Khati et al. (2003). Briefly, 100 µl reaction mixture contained: 1.5 ng template DNA, 1× transcription buffer (New England Biolabs® Inc., MA, USA) 2 mM spermidine, 1 mM rATP, 1 mM rGTP, 1.5 mM 2'F CTP, 1.5 mM 2'F UTP (Fermentas, Thermo Fisher Scientific Inc., USA), 2 U T7 RNA Polymerase (New England Biolabs® Inc., MA, USA). Transcription reaction was incubated overnight at 37° C. The reaction was stopped with the addition of 1 U RNAse free DNAse I in 1× reaction buffer (Fermentas, Thermo Fisher Scientific Inc., MA, USA) and incubated at 37° C. for 25 minutes. RNA aptamers were purified from low molecular weight contaminants using NucAway™ Spin Columns (Ambion, NY, USA). Columns were hydrated using 650 µl 1× HMCKN buffer (10 mM Hepes pH 7.4, 1 mM $MgCl_2$, 1 mM $CaCl_2$, 2.7 mM KCl, and 150 mM NaCl) for five minutes at room temperature. The columns were placed in collection tubes and spun for two minutes at 750×g to remove excess interstitial fluid. The flow through was discarded and the in vitro transcription product was added directly to the centre of the gel bed. The columns were placed into clean collection tubes and spun for two minutes at 750×g. The flow through contained the clean RNA ready for use and the spin columns were discarded. RNA was quantified using a NanoDrop 1000 spectrophotometer (Thermo Fisher Scientific Inc., MA, USA) at $A_{260}$. The 260:280 ratio was used as an indication of RNA purity with an expected ratio of 2.0 for pure RNA. RNA fractions from each step were resolved on a 12 polyacrylamide 8 M urea gel in 1× TBE running buffer at 200 V, to validate the RNA production quality. RNA was prepared for electrophoresis by incubation with 1× RNA loading dye (Fermentas, Thermo Fisher Scientific Inc., USA) and heated to 95° C. for three minutes. Visualisation was achieved by ethidium bromide staining under UV light with a Molecular Imager Chemidoc XRS+ Imaging System (BIORAD, CA, USA). For the correct folding, aptamers were denatured at 95° C. for three minutes and refolded in the presence of 1× HMCKN buffer and incubated at room temperature for ten minutes prior to use.

Fluorescent Labelling of Anti-CD7 Aptamers

Aptamers were end labelled with 6-carboxy-fluorescein (FAM, excitation 494 nm and emission 518 nm) so that they could be tracked using microscopy and flow cytometry for internalisation and binding. A Silencer® siRNA Labelling Kit (Ambion, NY, USA) was used according to manufacturer's protocols. The labelling reaction was prepared with 5 µg single stranded RNA, 1× labelling buffer and 15% FAM Labelling Reagent and was incubated at a constant temperature of 37° C. for one hour in the dark. The labelled RNA was then ethanol precipitated to remove excess labelling reagent as it may cause short term toxicity of transfected cells. To precipitate the RNA, 0.1 volume 5 M NaCl and 2.5 volumes 100% ethanol were added to the end labelling reaction and after mixing well, the reaction was incubated at −20° C. for one hour. The RNA was pelleted by centrifugation at 80 000×g for 15 minutes after which the supernatant was removed and by this stage the RNA was visible as a green pellet. The RNA pellet was washed in 70% ethanol before being air dried at room temperature in the dark. The pellet was then re-suspended in 1× HMCKN buffer and quantified using the microarray assay to detect fluorescence concentration on a NanoDrop 1000 spectrophotometer (Thermo Fisher Scientific Inc., MA, USA).

Flow Cytometry Analysis of Cell Surface Binding of Anti-CD7 Aptamers

Aptamer binding to the cell surface expressed CD7 receptor was assessed using flow cytometry. CD7-HeLa and un-transfected HeLa cells were suspended at a concentration of $1\times10^5$ cells/ml in serum free media. A portion of the CD7-HeLa cells was incubated with an 0.5 µg anti-CD7 monoclonal antibody (CD7 (H-7): sc-28332; Santa Cruz Biotechnology, Inc., CA, USA) antibody at 4° C. for 20 minutes after which all cells were incubated with 400 nM FAM labelled aptamer for 20 minutes. The cells were then washed three times in 500 µl PBS at 4° C. before being re-suspended in 100 µl serum free media at 4° C. for analysis by flow cytometry using a Guava Easy Cyte Flow cytometer (Guava Technologies Inc., CA, USA). The results were analysed and processed using FlowJo version 7.6.5 (Tree Star, Inc., OR, USA). For each run, 10 000 events were counted and cells gated according to forward and side scatter profiles. Aptamer bound cells were compared to cells alone and the percentage cells stained was determined. Aptamer binding to CD7-HeLa cells was compared to binding of un-transfected HeLa cells and to the CD7-HeLa cells blocked with an anti-CD7 monoclonal antibody.

Confocal Microscopy Analysis of Anti-CD7 Aptamer Internalisation

Initial screening of aptamer CSIR 3.3, CSIR 3.53 and CSIR 3.23 internalisation was conducted by incubating the fluorescently labelled aptamer with CD7-HeLa cells and un-transfected HeLa cells at 37° C. for 20 minutes. CD7-HeLa cells and un-transfected HeLa cells were seeded at a density of $2\times10^5$ cells/ml onto 14 mm glass coverslips and incubated overnight at 37° C. with 5% $CO_2$. Following incubation, aptamers CSIR 3.3, CSIR 3.53 and CSIR 3.23 were added to the cells at a final concentration of 20 nM and incubated for two hours at 37° C. Coverslips were washed with pre-warmed PBS (Gibco, BRL, UK) and fixed using 4% (w/v) paraformaldehyde at room temperature for 30 minutes. The fixed cells were washed three times with PBS at room temperature and stained using HCS CellMask™ Blue Whole Cell Stain, excitation 346 nm and emission 442 nm (Invitrogen, CA, USA) at room temperature for 30 minutes. Staining was followed by another three washes with PBS (Gibco, BRL, UK) after which the coverslip was mounted using 50% Glycerol in PBS mounting media. Slides were imaged using a Nikon $T_1$ eclipse (Nikon Corporation, Japan) with an Andor enccd 16 bit camera (Andor Technology plc., UK). A Z-stack of images was taken from within the cell, excluding the cell surface. This was to ensure that only aptamer within the cell and not those attached to the cell surface was imaged. ImageJ 1.45 software was used to analyse the images and to flatten the stack images into a single image selecting for "maximum Intensity". Cellular staining stack was flattened using the "average Intensity" command. Both images were processed by subtracting the background and normalised using "enhance contrast" with 0.01% saturated pixels before generating a montage of the images. Green pseudo colour was assigned to the aptamer stain while gray scale was used for the cellular staining.

Anti-CD7 Aptamer Association to Endogenously Expressed Surface CD7 Receptor on T Lymphocytes Jurkat cells were selected to be used as the T lymphocyte cell line for aptamer association characterisation. Jurkat cells were grown to a density of $4\times10^6$ cells/ml in complete media and seeded into a 96 well dish (Nunc™, Thermo Fisher Scientific, Inc., MA, USA) at a density of $2\times10^5$ cells per well. CD7 specific aptamers (CSIR 3.14, CSIR 3.28, CSIR 3.31, CSIR 3.35, CSIR 3.37, CSIR 3.39, CSIR 3.42 and CSIR 3.48) selected from binding studies with CD7-HeLa cells were tested for binding to Jurkat T lymphocytes. Cy3 labelled aptamer was incubated over night with Jurkat cells in complete media at 37° C. and 5% $CO_2$ at a final concentration of 400 nM. As a positive control for aptamer internalisation, aptamers were transfected into cells using Lipofectamine RNAiMAX reagent (Invitrogen, CA, USA). Following incubation, cells were pelleted and washed three times with PBS. After washing, cells were re-suspended in 400 µl PBS and analysed using a CyAn flow cytometer (Beckman Coulter Inc., CA, USA); the results analysed using FlowJo version 7.6.5 (Tree Star, Inc., OR, USA). For each run, 10 000 events were collected with cells gated according to forward and side scatter profiles. Aptamer bound cells were compared to cells alone and the percentage cells stained was determined. Each aptamer alone association was normalised to its transfection control set to 100%. A student's t test was conducted to determine a significant difference between the transfection control and the aptamer alone. The average of two experiments was used to validate the association of anti-CD7 aptamers.

Anti-CD7 Aptamer Association Rates and Binding Characterisation

Aptamers CSIR 3.14 and CSIR 3.37 and CSIR3.42 shown to bind Jurkat cells were further analysed to determine their kinetic rate constants. Jurkat cells were grown to a density of $4 \times 10^6$ cells/ml in complete media and seeded into a 96 well dish (Nunc™, Thermo Fisher Scientific, Inc., MA, USA) at a density of $2 \times 10^5$ cells per well. Cy3 labelled aptamers were incubated for different time periods (1 hour, 3 hours, 6 hours, 12 hours and 24 hours) with Jurkat cells in complete media at 37° C. and 5% $CO_2$ at a final concentration of 400 nM. Following incubation, cells were pelleted and washed three times with PBS. After washing, cells were re-suspended in 400 µl PBS and analysed using a CyAn flow cytometer (Beckman Coulter Inc., CA, USA). The results were analysed using FlowJo version 7.6.5 (Tree Star, Inc., OR, USA). For each run, 10 000 events were collected with cells gated according to forward and side scatter profiles. Aptamer bound cells were compared to cells alone and the percentage cells stained was determined. The mean and median fluorescence was calculated for cells alone as well as those stained with the Cy3 labelled aptamer. The average of two experiments was used to validate the association of anti-CD7 aptamers with surface expressed CD7 receptor. The percentage stained cells was analysed across time periods and a non-linear regression line was fit (GraphPad Prism Software Inc., CA, USA) to determine the association and dissociation rate constants.

Limit of Detection for Aptamer Association with Jurkat Cells

Aptamers CSIR 3.14 and CSIR 3.37 were analysed to determine the limit of detection for aptamer-cell association. Jurkat cells were grown to a density of $4 \times 10^6$ cells/ml in complete media and seeded into a 96 well dish (Nunc™, Thermo Fisher Scientific, Inc., MA, USA) at a density of $2 \times 10^5$ cells per well. Cy3 labelled aptamers were incubated for 12 hours with Jurkat cells in complete media at 37° C. and 5% $CO_2$ at varied final concentrations (10.9 nM, 21.9 nM, 43.8 nM, 87.5 nM, 175 nM, 350 nM and 700 nM). Following incubation, cells were pelleted and washed three times with PBS. After washing, cells were re-suspended in 400 µl PBS and analysed for fluorescence using a CyAn flow cytometer (Beckman Coulter Inc., CA, USA). The results analysed using FlowJo version 7.6.5 (Tree Star, Inc., OR, USA). For each run, 10 000 events were collected with cells gated according to forward and side scatter profiles. Aptamer bound cells were compared to cells alone and the percentage cells stained was determined. The average of two experiments was used to validate the concentration gradient association of anti-CD7 aptamers. Aptamer binding was normalised to negative control aptamer CSIR 3.31 binding at 12 hours.

Aptamer CSIR 3.14 Binding Site Mutation Characterisation

Aptamer CSIR 3.14 secondary structure prediction highlighted a region of conservation that may attribute to CD7 binding. This prediction was tested by removing ten nucleotide sections of the binding region and assessing association to Jurkat cells. The DNA of aptamer CSIR 3.14 was also assessed for Jurkat cell association. Jurkat cells were grown to a density of $4 \times 10^6$ cells/ml in complete media and seeded into a 96 well dish (Nunc™, Thermo Fisher Scientific, Inc., MA, USA) at a density of $2 \times 10^5$ cells per well. FAM labelled aptamer (Generated according to Chapter 3.2.2) was incubated over night with Jurkat cells in complete media at 37° C. and 5% CO2 at a final concentration of 400 nM. As a positive control for aptamer association, full length aptamer CSIR 3.14 was included. Following incubation, cells were pelleted and washed three times with PBS. After washing, cells were re-suspended in 400 µl PBS and analysed on a Guava Easy Cyte Flow cytometer (Guava Technologies Inc., CA, USA) and the results analysed using FlowJo version 7.6.5 (Tree Star, Inc., OR, USA). For each run, 10 000 events were counted with cells gated according to forward and side scatter profiles. Green fluorescence was gated to remove red auto-fluorescence of the cells. Each aptamer mutation and the DNA was normalised to the association of full length CSIR 3.14 set to 100%. A student's t test was conducted to determine a significant difference between the transfection control and the aptamer alone. Two independent experiments were used to calculate the association of each aptamer. A computation analysis of aptamer CSIR 3.14 mutants and DNA was conducted to predict the secondary structure.

Anti-CD7 Aptamer Internalisation Characterisation and Localisation

Aptamer CSIR 3.14 was selected for further characterisation of internalisation in Jurkat T lymphocytes. A glass bottom cell chamber (Mateck, MA, USA) was coated with Poly-L-lysine solution 0.1% (w/v) in water (Sigma-Aldrich, MO, USA) to allow for the suspension cells to attach to the chamber's surface. Jurkat cells ($2 \times 10^5$ cells) were added to the centre of the dish and allowed to settle and attach for 20 minutes at 37° C. with 5% $CO_2$. Live cells were placed in an incubation chamber attached to a Zeiss LSM 510 confocal microscope (Carl ZeissAG, Oberkochen, Germany) for live cell imaging using a 40× objective. A Z-stack of images through the cell section was performed with 1 µm sections. These images were analysed using Zeiss LSM Image Browser version 3.5 (Carl ZeissAG, Oberkochen, Germany) to generate a three dimensional projection of the stack (Supplementary Data). These tools were used to localise the aptamer fluorescence to inside the cells.

Anti-CD7 Aptamer Kinetics of Internalisation

Aptamer CSIR 3.14 was selected for further kinetic internalisation characterisation in Jurkat T lymphocytes by confocal microscopy. A glass bottom cell chamber (Mateck, MA, USA) was coated with Poly-L-lysine solution 0.1% (w/v) in water (Sigma-Aldrich, MO, USA) to allow for the suspension cells to settle and attach to the chamber's surface. Jurkat cells ($2 \times 10^5$ cells) were added to the centre of the dish and allowed to settle and attach for 20 minutes at 37° C. with 5% $CO_2$. Live cells were placed in an incubation chamber attached to a Zeiss LSM 510 confocal microscope (Carl ZeissAG, Oberkochen, Germany) set for the detection of Cy3 fluorescence with an excitation of 550 nm and an emission of 570 nm. The time course imaging was conducted over a six hour period with images captured using a 40× objective at 15 minutes intervals. Zeiss LSM Image Browser version 3.5 (Carl ZeissAG, Oberkochen, Germany) was used to analyse images. Two regions of interest (ROI 1 and ROI 2) were selected including the whole field of view and a single cell respectively. These regions were analysed for an accumulation of fluorescence signal over time. This data was analysed using GraphPad Prism version 5 (GraphPad Prism Software Inc., CA, USA) and a non-linear regression line was fit to the data to determine the association and dissociation rate constants. The equation used to define the kinetics of association used to generate the fit line and rate constants is shown below:

$$Y=Ymax\times(1-e^{-kob\cdot X})$$

kob=observed rate constant (min$^{-1}$)
Ymax=maximum Y value (specific binding)
X=time (min)

Mammalian Cell Culture

HeLa mammalian cells were maintained at a density of $5\times10^5$ cells/ml. The cells were maintained in Dulbecco's Modified Eagle's Medium (DMEM) with L-glutamine (Gibco, BRL, UK) supplemented with 10% FBS (Gibco, BRL, UK) in a humidified incubator with 5% $CO_2$ at 37° C. Cell viability was determined by trypan exclusion under a light microscope after each passage. CD7-HeLa mammalian cells were maintained at a density of $5\times10^5$ cells/ml. The cells were maintained in Dulbecco's Modified Eagle's Medium (DMEM) with L-glutamine (Gibco, BRL, UK) supplemented with 10% FBS (Gibco, BRL, UK) and 50 μg/ml neomycin in a humidified incubator with 5% $CO_2$ at 37° C. Cell viability was determined by trypan exclusion under a light microscope after each passage. Jurkat cells are a T lymphoblast derived from peripheral blood buffy coat of a 14 year old male with acute lymphoblastic leukaemia (ATCC #TIB-152). Jurkat T lymphocytes were maintained at a density of $1\times10^5$ cells/ml. The cells were maintained in RPMI with 2 mM L-glutamine (Gibco, BRL, UK), 1 mM sodium pyruvate (Gibco, BRL, UK), 4500 mg/ml glucose (Gibco, BRL, UK), 1500 mg/ml sodium-bicarbonate (Gibco, BRL, UK) and supplemented with 10% FBS (Gibco, BRL, UK) in a humidified incubator with 5% $CO_2$ at 37° C. Cell viability was determined by trypan exclusion under a light microscope after each passage.

Aptamer Conjugation to siRNA

Figure 28:
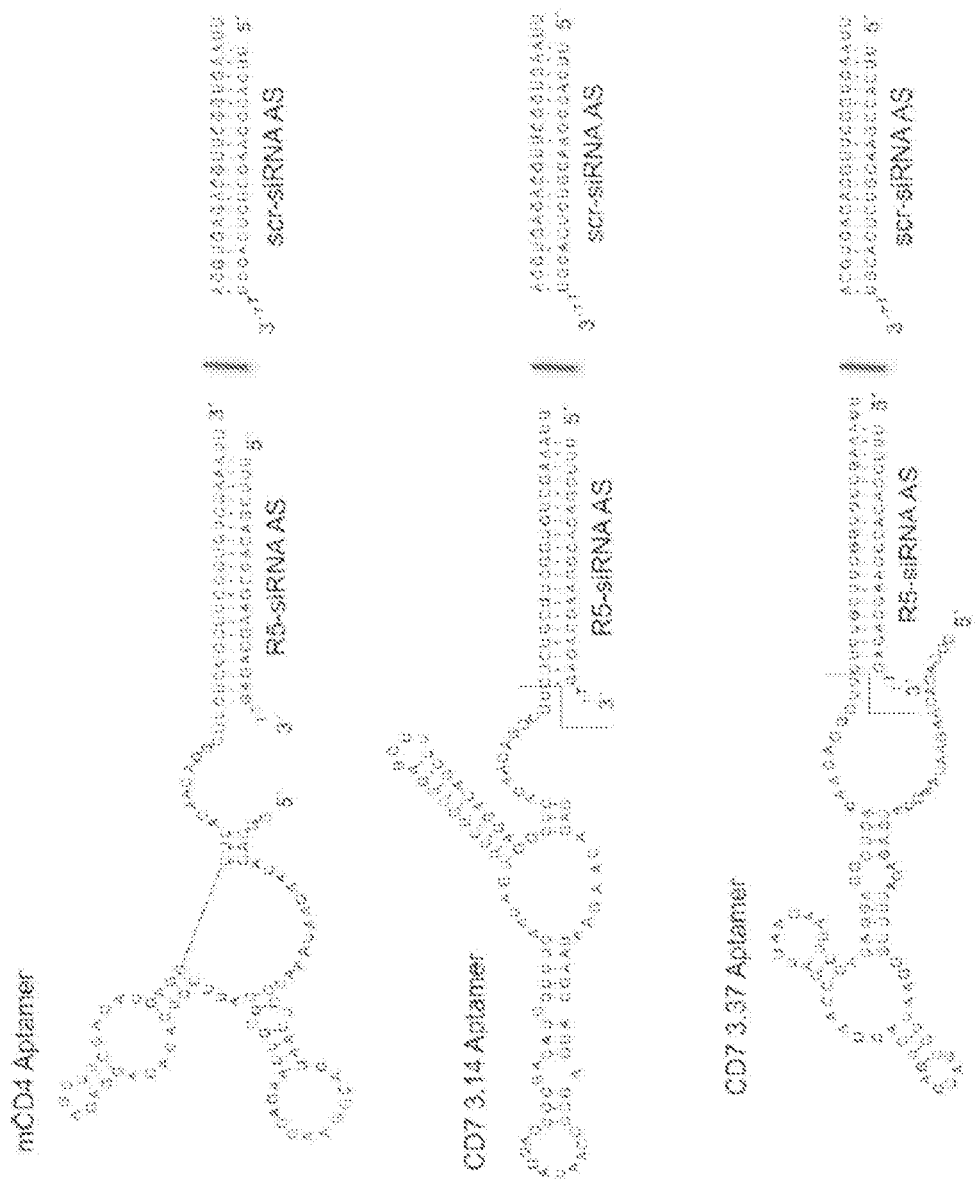
FIG. 28: The designs of three CD7 aptamer-siRNA chimeras.

Three aptamer-siRNA chimeras were designed. The siRNAs are targeted to inhibit the CCR5 receptor (R5-siRNA) and an irrelevant scrambled control siRNA (scr-siRNA). Two separate CD7 aptamers were used to form chimeras: CD7 3.14 and CD7 3.37 (FIG. 28). Control siRNAs were transfected using the non-specific dendrimer G5. RNA was collected 48 hours post transfection and extracted RNA was used to measure CCR5 expression.

Results

Selection of Internalising Anti-CD7 Aptamers by Whole Cell SELEX

Whole cell (in vivo) SELEX was used to generate RNA aptamers capable of internalising cells using the human surface CD7 receptor. The stably transfected CD7-HeLa cell line generated was used for positive selection of internalising aptamers. The un-transfected HeLa cells, confirmed for no CD7 receptor expression, were used for negative selection to remove non-specific internalising RNA species. At each round of selection, the PCR was optimised for cycle number (FIG. 2). The maximum PCR cycle number chosen such that the PCR fragment would over amplify (higher bands after 24 cycles, FIG. 2). At higher number of cycles, the primer dimers start to amplify and can be seen as a band at roughly 75 nucleotides (FIG. 2). The band of interest can be seen in line with the 100 nucleotide band of the molecular weight marker (FIG. 2). The cycle number that generated a single band was chosen as the optimal cycle number for PCR amplification of the DNA for that round of selection.

Figure 3:
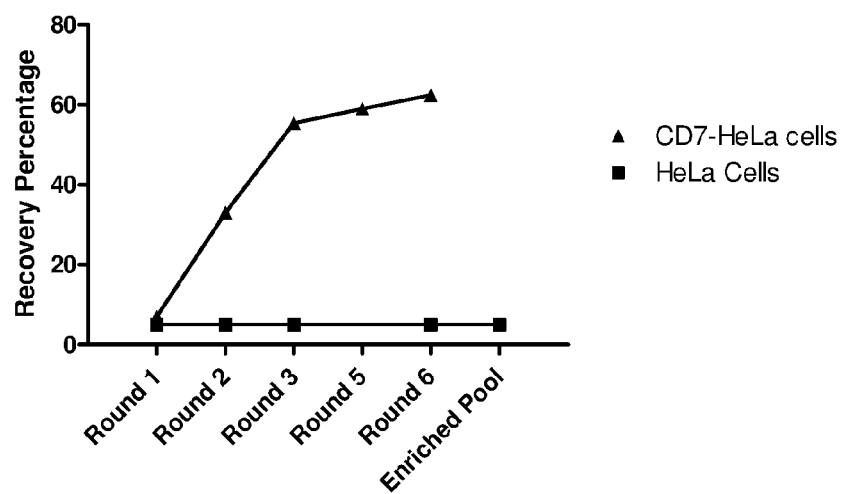
FIG. 3: Recovery from internalising (in vivo) whole cell SELEX. CD7 specific internalising aptamers were selected after five rounds of positive selection in CD7-HeLa cells and one round of negative selection in un-transfected HeLa cells. Each round of recovery was repeated in un-transfected HeLa cells to confirm the enrichment of CD7 specific aptamers. The recovery from un-transfected HeLa cells remained constant while that in CD7-HeLa cells showed enrichment at each round.
Figure 4:
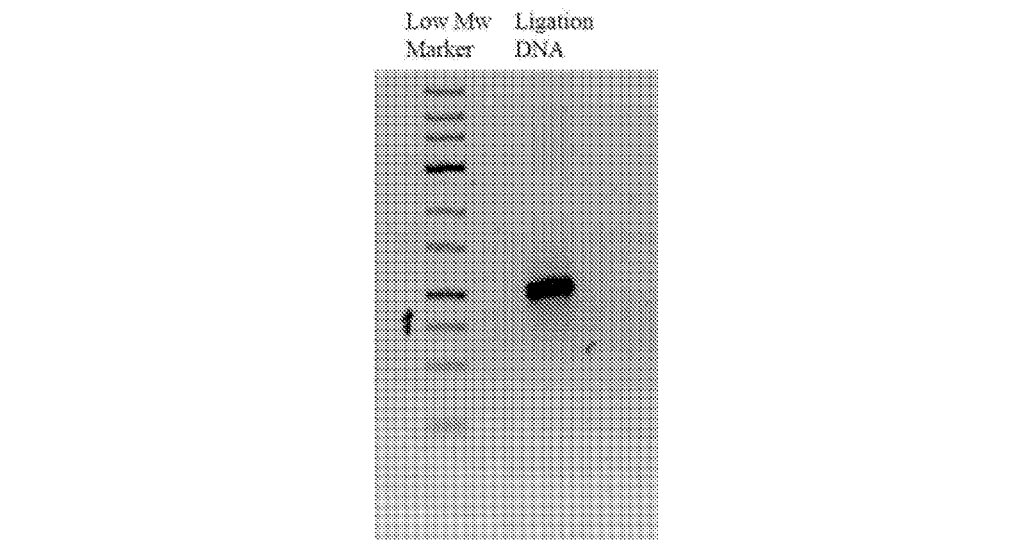
FIG. 4: PCR amplification of the enriched pool of CD7 specific aptamers after the last round of selection. The enriched pool of CD7 specific aptamers was amplified by a low magnesium concentration PCR. The PCR resulted in a single band at the correct size according to the molecular weight marker. Once confirmed as the correct size and quality, the DNA was ligated into a pGEM-T Easy® vector.

Three rounds of positive selection in CD7-HeLa cells were followed by a round of negative selection against un-transfected HeLa cells. The negative selection was followed by an additional two rounds of positive selection in CD7-HeLa cells. Each round of selection in CD7-HeLa cells was repeated in un-transfected HeLa cells and the recovery from each cell type compared (FIG. 3). The recovery from un-transfected HeLa cells remained constant while that in CD7-HeLa cells showed enrichment at each round indicating specificity for the expressed CD7 receptor. After six rounds of selection, the enriched pool of aptamers was amplified by PCR (FIG. 4) and ligated into a pGEM-T Easy® vector (Promega, WI, USA) for cloning into chemically competent One Shot TOP10 E. coli (Novagen, Merck, Darmstadt, Germany).

Figure 5:
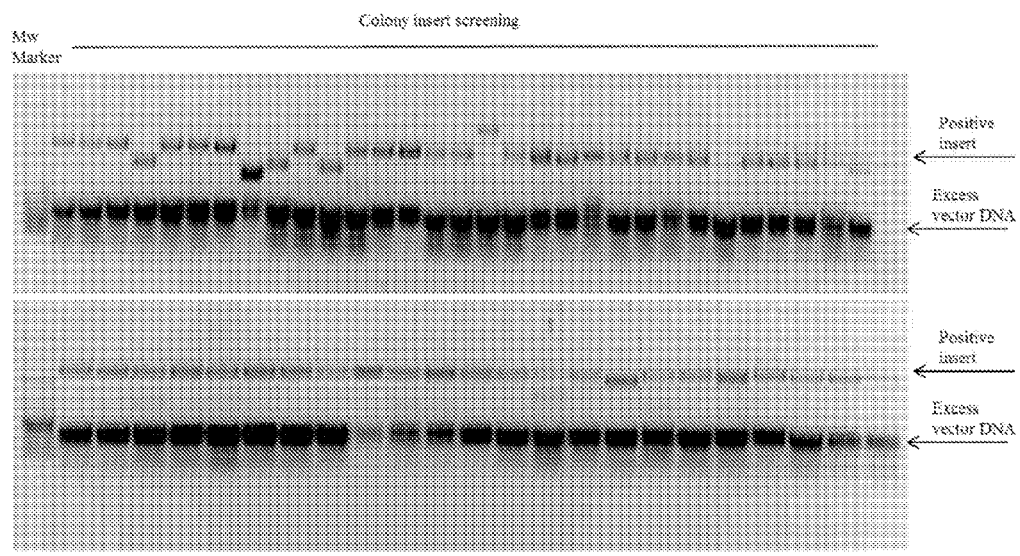
FIG. 5: Vector insert screening using M13 primers. Ninety six colonies were amplified using M13 specific primers to determine the insert positive clones. The positive insert was confirmed by a band at the indicated arrow. The excess vector DNA can be seen as a band below the band of interest and indicates an overloading of template into the PCR.

Ninety six colonies were picked and analysed for positive inserts. To detect positive inserts, each clone was amplified by PCR using M13 specific primers to amplify the vector (FIG. 5). Fifty-nine clones were positive for an insert and were sent for sequencing at Inqaba Biotech (South Africa).

Anti-CD7 Aptamer Clone Sequencing and Analysis

Figure 6:
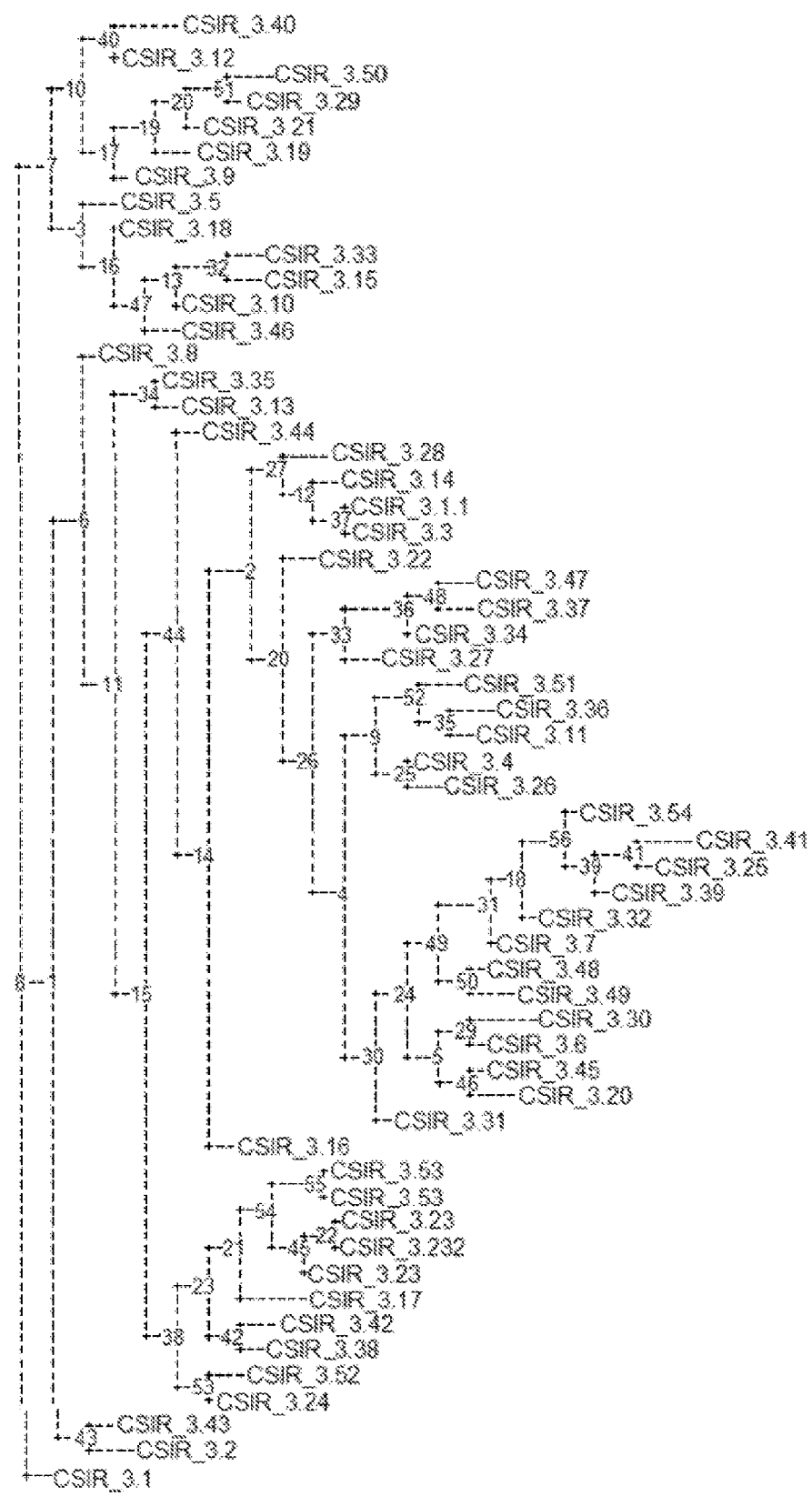
FIG. 6: Maximum likelihood phylogenetic tree of aptamer sequences. Aptamer sequences from the whole cell SELEX were aligned and plotted on a neighbour joining tree to identify similarity in the sequences. Aptamer sequences were very distinct with only three aptamers (CSIR 3.3, CSIR 3.23 and CSIR 3.53) pooled more than once.

Fifty-nine aptamer clones were sequenced (Table 2-1) and their sequences analysed for conserved motifs and sequence similarity using CLUSTAL W multiple alignment application in BioEdit V7.1.3.0 software (Hall, 1999). Aptamers were assigned names based on the order of their sequencing and so do not reflect their attributes. Of the 59 aptamer clones, three were pooled more than once, aptamers CSIR 3.3, CSIR 3.23 and CSIR 3.53. The remaining aptamer sequences were highly divergent. A maximum likelihood phylogenetic tree of the aptamer clones was generated and indicates the great diversity of the clones (FIG. 6).

TABLE 1

CD7 specific internalising aptamer clone sequences

| Aptamer Name | Aptamer Sequences | SEQ ID NO |
|---|---|---|
| CSIR 3.1 | GGGAGACAAGAAUAAGCAUGAAACCCCAACUCUGGC GCACAUUUCCCGCCACCACCGUAGAAUACUUCGAC AGGAGGCUCACAACAGGC | 58 |
| CSIR 3.2 | GGGAGACAAGAAUAAGCAUGCCCUUCCCUAGAACGC AGGCAGCAGUUACUCGGAGAACCCUACCCUUCGACA GGAGGCUCACAACAG | 59 |
| CSIR 3.3 | GGGAGACAAGAAUAAGCAUGGGACCCCAACUAGCGU GUCAUUGUUCGAAUCGACUGAGAUUUCGGGUUCGAC AGGAGGCUCACAACAGGC | 60 |
| CSIR 3.4 | GGGAGACAAGAAUAAGCAUGAGACUGAUCCAAAUAC GACACAAAUACCCGGCACUAGACGUUCGACAGGAGG CUCACAACAGGC | 61 |
| CSIR 3.5 | GGGAGACAAGAAUAAGCAUGAGCAUCAAUCUAGACU AGACUCAGAUUACCAGCGAACUAGUGUAUCUUCGAC AGGAGGCUCACAACAGGC | 62 |
| CSIR 3.6 | GGGAGACAAGAAUAAGCAUGUAAUUCCAGCAUAAAA AAGAUAGGUACUAUUAAUACACGACCAGAAUUCGAC AGGAGGCUCACAACAGGC | 63 |

TABLE 1-continued

CD7 specific internalising aptamer clone sequences

| Aptamer Name | Aptamer Sequences | SEQ ID NO |
|---|---|---|
| CSIR 3.7 | GGGAGACAAGAAUAAGCAUGAUCUACGCGACCACAA AAUUAUCCGCGAUUUGAAUAUUCGACAGGAGGCUCA CAACAGGC | 64 |
| CSIR 3.8 | GGGAGACAAGAAUAAGCAUGCCCCUUGCGGUUCCCA CAUUAUCUCUCUGCUAUCCCGAUGGCCCGAUUCGAC AGGAGGCUCACAACAGGC | 65 |
| CSIR 3.9 | GGGAGACAAGAAUAAGCAUGAGACAUUCUCUCCGCC CUCAACUCCGCCCGCUCCAUCCAGUUCCCUGUCGAC AGGAGGCUCACAACAGGC | 66 |
| CSIR 3.10 | GGGAGACAAGAAUAAGCAUGGCCGAUCCAUCCUCCC CACGACCAUCAUGAAUCCCAACAGGAACUUCGACAG GAGGCUCACAACAGGC | 67 |
| CSIR 3.11 | GGGAGACAAGAAUAAGCAUGGGAUAGUUCUGCGUAG CUUAAGAGAUGUUAAAUCACACCCACGCCAUUCGAC AGGAGGCUCACAACAGGC | 68 |
| CSIR 3.12 | GGGAGACAAGAAUAAGCAUGGCUAUCAUACCCGAGA CCGCUAUCCCCACCUUAAUGUUCCUUCGACAGGAG GCUCACAACAGGC | 69 |
| CSIR 3.13 | GGGAGACAAGAAUAAGCAUGAGACCGUACACCUCGC UCGCCAUCCGACUUUGAAUAAGCAUAGACCUUCGAC AGGAGGCUCACAACAGGC | 70 |
| CSIR 3.14 | GGGAGACAAGAAUAAGCAUGAGCGCCAAUAUGACCG CGACAUCGUUUGAAUAGUUCCUGGGGAUCUUUCGAC AGGAGGCUCACAACAGG | 71 |
| CSIR 3.15 | GGGAGACAAGAAUAAGCAUGCCGGAUAAGGUCGUCC GUAGUACCGGUUAACGUACCAGCCUUACUCUUCGAC AGGAGGCUCACAACAGGC | 72 |
| CSIR 3.16 | GGGAGACAAGAAUAAGCAUGAUCUAAAGACAGAUUU AAUACUACCCGUCGUAUCCAACUCGGAACGGUCGAC AGGAGGCUCACAACAGGC | 73 |
| CSIR 3.17 | GGGAGACAAGAAUAAGCAUGUACGUAGACAAGAGAU UUCCAGACCCUGUUACUAAUACAUUUCCCGUUCGAC AGGAGGCUCACAACAGGC | 74 |
| CSIR 3.18 | GGGAGACAAGAAUAAGCAUG<u>CCUACAUUC</u>GACAGGA GGCUCACAACAGGC | 75 (21) |
| CSIR 3.19 | GGGAGACAAGAAUAAGCAUGCUCUGACAAUCCUGCA ACAAUUACAUUCAUUAACGGGCUAAUUCAUAUCGAC AGGAGGCUCACAACAGGC | 76 |
| CSIR 3.20 | GGGAGACAAGAAUAAGCAUGAUAUGUAGUAACCCA AUGAUAAAUAACUAAGACCGCAAGUCAGUUCGACAG GAGGCUCACAACAGGC | 77 |
| CSIR 3.21 | GGGAGACAAGAAUAAGCAUGCCACUCCCACACUUCC UUAAUCCGCGCUAACACACCAUAUGUACUUCGACAG GAGGCUCACAACAGGC | 78 |
| CSIR 3.22 | GGGAGACAAGAAUAAGCAUGCGUUAGCAGAUACAUC GAGAUUGCAAAGUCCAAUACAGUUAAUAAGUUCGAC AGGAGGCUCACAACAGGC | 79 |
| CSIR 3.23 | GGGAGACAAGAAUAAGCAUGGAGUGCGUCGCCACUA CUCCUCUCAUUACCUCUUGCAUUUCACUAUUCGACA GGAGGCUCACAACAGGC | 80 |
| CSIR 3.24 | GGGAGACAAGAAUAAGCAUGCCCCACCCCACUAUUA GCCGAACCCGAACCCCAUCUUACCCGGACCCGACAG GAGGCUCACAACAGGC | 81 |
| CSIR 3.25 | GGGAGACAAGAAUAAGCAUGUUCUCUGCGGUCUAGG UCACGAUAUACCCGUUACAUAUCAUUCCUGUUCGAC AGGAGGCUCACAACAGGC | 82 |
| CSIR 3.26 | GGGAGACAAGAAUAAGCAUGUACAAAUCCGCAUAUA CACCCAACCACACCCAAUCCUCUCAGUCCAUUCGAC AGGAGGCUCACAACAGGC | 83 |
| CSIR 3.27 | GGGAGACAAGAAUAAGCAUGCCCUAGCAACAUUCUA UGCGCAAACCAUAGUUAUGACUAUUGACUCUUCGAC AGGAGGCUCACAACAGGC | 84 |
| CSIR 3.28 | GGGAGACAAGAAUAAGCAUGCACACCGGCUGAGUAU CUGCCUGUGUAAUCGAAACAACUGCGACAUUCGACA GGAGGCUCACAACAGGC | 85 |
| CSIR 3.29 | GGGAGACAAGAAUAAGCAUGCCGCACCCGUACCUCC UUCCUCUCAGGUAUUCACUCACAUCAUUUCGACAGG AGGCUCACAACAGG | 86 |
| CSIR 3.30 | GGGAGACAAGAAUAAGCAUGCACGGAUGACAGCAGA AUAACUCCUACAGUCCAUAUAUAAACGAUUUUCGAC AGGAGGCUCACAACAGGC | 87 |
| CSIR 3.31 | GGGAGACAAGAAUAAGCAUGCAAUUUAUCGAGACCC AGAUAACCGAUUUAUACGCAGACGAUAAGUUUCGAC AGGAGGCUCACAACAGGC | 88 |
| CSIR 3.32 | GGGAGACAAGAAUAAGCAUGAGCCCCACAUCCUACG CCACUCACCCACGCAUCCCGAUUGAUCAAAUUCGAC AGGAGGCUCACAACAGGC | 89 |
| CSIR 3.33 | GGGAGACAAGAAUAAGCAUGGGGAUAGCCGCACUUC UCACAGGAGUCGAGUCUUUUGAUCGGUCUCUUCGAC AGGAGGCUCACAACAGGC | 90 |
| CSIR 3.34 | GGGAGACAAGAAUAAGCAUGCGUGCGCCUAUGAUGA GUCUGGUUCACAUAAUUUGCGUUAGUUAGUUUCGAC AGGAGGCUCACAACAGGC | 91 |
| CSIR 3.35 | GGGAGACAAGAAUAAGCAUG<u>GAUCUUUC</u>GACAGGAG GCUCACAACAGGC | 92 (38) |
| CSIR 3.36 | GGGAGACAAGAAUAAGCAUGGGCAGCGAUAGACUGU UAACUACAGACGGGAGUCCGCGUUUCGACAGGAGGC UCACAACAGGC | 93 |
| CSIR 3.37 | GGGAGACAAGAAUAAGCAUGAGAGAUUUUGGGAAGG CUCAGGACUGCCUACUAACCCGAUAAGAAUUCGACA GGAGGCUCACAACAGGC | 94 |
| CSIR 3.38 | GGGAGACAAGAAUAAGCAUGCAUCCCCAGGCUCUUC CAUCAAGCAAUUAAUACAAUCACAACCCCUUCGAC AGGAGGCUCACAACAGGC | 95 |
| CSIR 3.39 | GGGAGACAAGAAUAAGCAUGUUAGCUCCGUCAGGUA UCCACAGAUCAUUGUUCAAUACAUUCGACAGGAGGC UCACAACAGGC | 96 |
| CSIR 3.40 | GGGAGACAAGAAUAAGCAUGCCAUGAUAUACCGAUA UUAACUUCGCGUUGCACAAGAAUACACUGUUCGAC AGGAGGCUCACAACAGGC | 97 |
| CSIR 3.41 | GGGAGACAAGAAUAAGCAUGCGAAAUCUAUGCCCAC GGUUGCAUCACCCGUUCUGAUCAUAUACUUAAAGUU AGGAGGCUCACAACAGGC | 98 |
| CSIR 3.42 | GGGAGACAAGAAUAAGCAUGCGUCCCACACCCUCCG AUUCCGACCAGGACUGGAUACUUACACUUUUUCGAC AGGAGGCUCACAACAGGC | 99 |
| CSIR 3.43 | GGGAGACAAGAAUAAGCAUGCCCCUUCGCCCAAAA CAUAUCGCUUCGACCUUCCACACCCUAUCAUUCGAC AGGAGGCUCACAACAGGC | 100 |

TABLE 1-continued

CD7 specific internalising aptamer clone sequences

| Aptamer Name | Aptamer Sequences | SEQ ID NO |
|---|---|---|
| CSIR 3.44 | GGGAGACAAGAAUAAGCAUGUUCCUGGAGACGCCUA UAGUACCUUGCCCCGUAGUAUCUGAUCAAUUCGACA GGAGGCUCACAACAGGC | 101 |
| CSIR 3.45 | GGGAGACAAGAAUAAGCAUGUUACCUACAAAAAAGA AAAAGAAUUAAACGGAUUAAGAAGGGGAAAAAGUAG UUCGACAGGAGGCUCACAACAGGC | 102 |
| CSIR 3.46 | GGGAGACAAGAAUAAGCAUGAUUGAGCCCUCCGCCC AAACUCACUCUCAACAAACCGCUGGAACGCUUCGAC AGGAGGCUCACAACAGGC | 103 |
| CSIR 3.47 | GGGAGACAAGAAUAAGCAUGACCGUGCUCUGUGACA GGACUUUACUUAGGGAUAAGGGUUGAAACUUCGACA GGAGGCUCACAACAGGC | 104 |
| CSIR 3.48 | GGGAGACAAGAAUAAGCAUGCUGGCAAUAAACGGCU AUAAGUAAAGUUCGACAGGAGGCUCACAACAGGC | 105 |
| CSIR 3.49 | GGGAGACAAGAAUAAGCAUGCAAAAUAUACAAAUAA CAGACAGAAUACUUUGCAUCAAUAGUUGGAUUCGAC AGGAGGCUCACAACAGGC | 106 |
| CSIR 3.50 | GGGAGACAAGAAUAAGCAUGCGCGCAUAAACCUAAC GCGCUUUUCUCUAGGUUGAUUAAACUGGGUUCGACA GGAGGCUCACAACAGGC | 107 |
| CSIR 3.51 | GGGAGACAAGAAUAAGCAUGAGCAGAUGUUGUGAUU AGUUGAACAAGGUCCCCAAACAUUGGAGGAUUCGAC AGGAGGCUCACAACAGGC | 108 |
| CSIR 3.52 | GGGAGACAAGAAUAAGCAUGCCUCAUUAACCCCGCU GUGCCCUGCAUCACUUCUCAUAGUCCGACACUCGAC AGGAGGCUCACAACAGGC | 109 |
| CSIR 3.53 | GGGAGACAAGAAUAAGCAUGCAGGUCCCACCGCCCC GCUCCCUUAUCAGCUUGGAAUACGUUUUCAUUCGAC AGGAGGCUCACAACAGGC | 110 |
| CSIR 3.54 | GGGAGACAAGAAUAAGCAUGUCAUCUCACCGCCAUA AUCCUCAACAUUCUCCCCACCCGAUUCCCGUUCGAC AGGAGGCUCACAACAGGC | 111 |

Minimal conservation was identified in this selection by the sequencing of a subset of the enriched pool. Greater conservation may have been identified from sequencing of the whole enriched pool rather than the selected clones, as described by Thiel, W. H. (2012) where Illumina next generation sequencing of each round of selection allowed for the selection to be tracked according to sequence diversity. It was seen that after the first three rounds of selection the sequence diversity was greatly reduced while the enrichment increased. This effect plateaued from the fifth round of selection. Future internalising aptamer selections using this method should be considered as it may present a more accurate measure of aptamer enrichment than the increase in percentage recovery at each round. It will also allow for the stopping point of selection to be more accurately identified. As such, the conservation within the enriched pool may be an under representation of the actual sequence similarity. As three sequences were identified as pooled more than once (aptamers CSIR 3.3, CSIR 3.23 and CSIR 3.53), these aptamers were used for initial binding and internalisation screening using CD7-HeLa cells and un-transfected HeLa cells.

Production and Preparation of Anti-CD7 Aptamers

Figure 7:
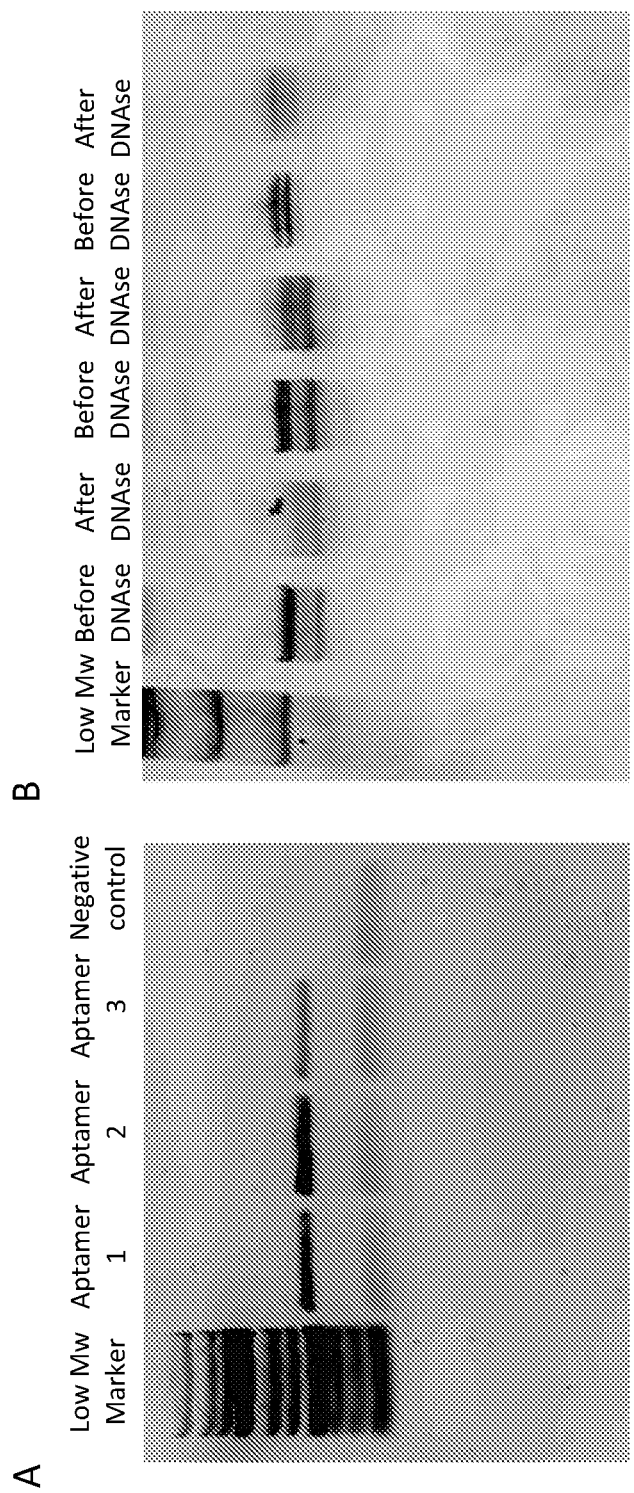
FIG. 7: Production of CD7 aptamers by PCR and in vitro transcription. A. Aptamers are amplified by PCR before transcribing to their active RNA. Aptamers (90 bp in size) can be seen aligned with the molecular marker at 100 nucleotides. B. Aptamers amplified by PCR are transcribed to their active RNA. Fractions before DNAse (BD) and After DNAse (AD) are separated on an 8M denaturing polyacrylamide gel. Multiple bands in the BD indicate DNA and RNA molecules

Aptamers used in all experiments were produced by PCR and in vitro transcription. PCR was used to amplify the aptamer DNA before transcribing the aptamer to RNA for use. Aptamer DNA and RNA were separated by gel electrophoresis to determine the quality and ensure the fragment generated is of the correct length (FIG. 7).

Figure 8:
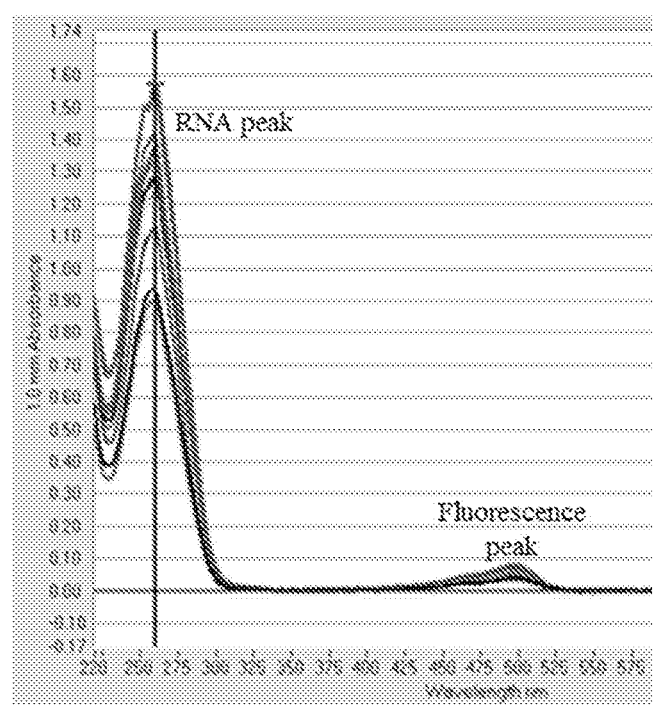
FIG. 8: Spectrophotometer quantification of labelled aptamer RNA. Quantification of RNA labelled with a fluorophore using spectrophotometry. The spectrum of the RNA and the label is shown labelled and the quantification of the labelled RNA is calculated.

Aptamer RNA was fluorescently labelled using a labelling kit for tracking of internalisation and binding by flow cytometry and confocal microscopy. The labelled RNA was quantified using a nanodrop spectrophotometer. The reading provides a spectrum of the RNA as well as the fluorescent label (FIG. 8) and the concentration of the labelled RNA is given. The average labelling efficiency was seen to be 80% for all aptamer clones. The labelled concentration was used for the calculations for all aptamer incubations for flow cytometry and microscopy experiments.

Anti-CD7 Aptamer Binding and Internalisation Specificity

Sequence analysis of the enriched aptamer pool revealed three aptamers pooled more than once, namely: CSIR 3.3, CSIR 3.53 and CSIR 3.23. These aptamers were selected for an initial pilot screening of aptamer specificity to CD7-HeLa cells using flow cytometry and confocal microscopy after which the remaining enriched pool was screened for binding. The flow cytometry assay tested binding specificity by incubating the cells with the aptamers at 4° C. to prevent membrane trafficking and thus prevent internalisation of the aptamer. This method is commonly used when characterising receptor mediated internalisation as it allows for surface binding to the receptor (Man, 2000). Warming of the cells after binding allows for internalisation via the receptor (Neves, 2012; Nguyen, 2011), this method was used for the confocal microscopy imaging of aptamer internalisation. Aptamer specificity was also assessed by blocking the CD7-HeLa cells with an anti-CD7 monoclonal antibody before aptamer incubation.

Figure 9:
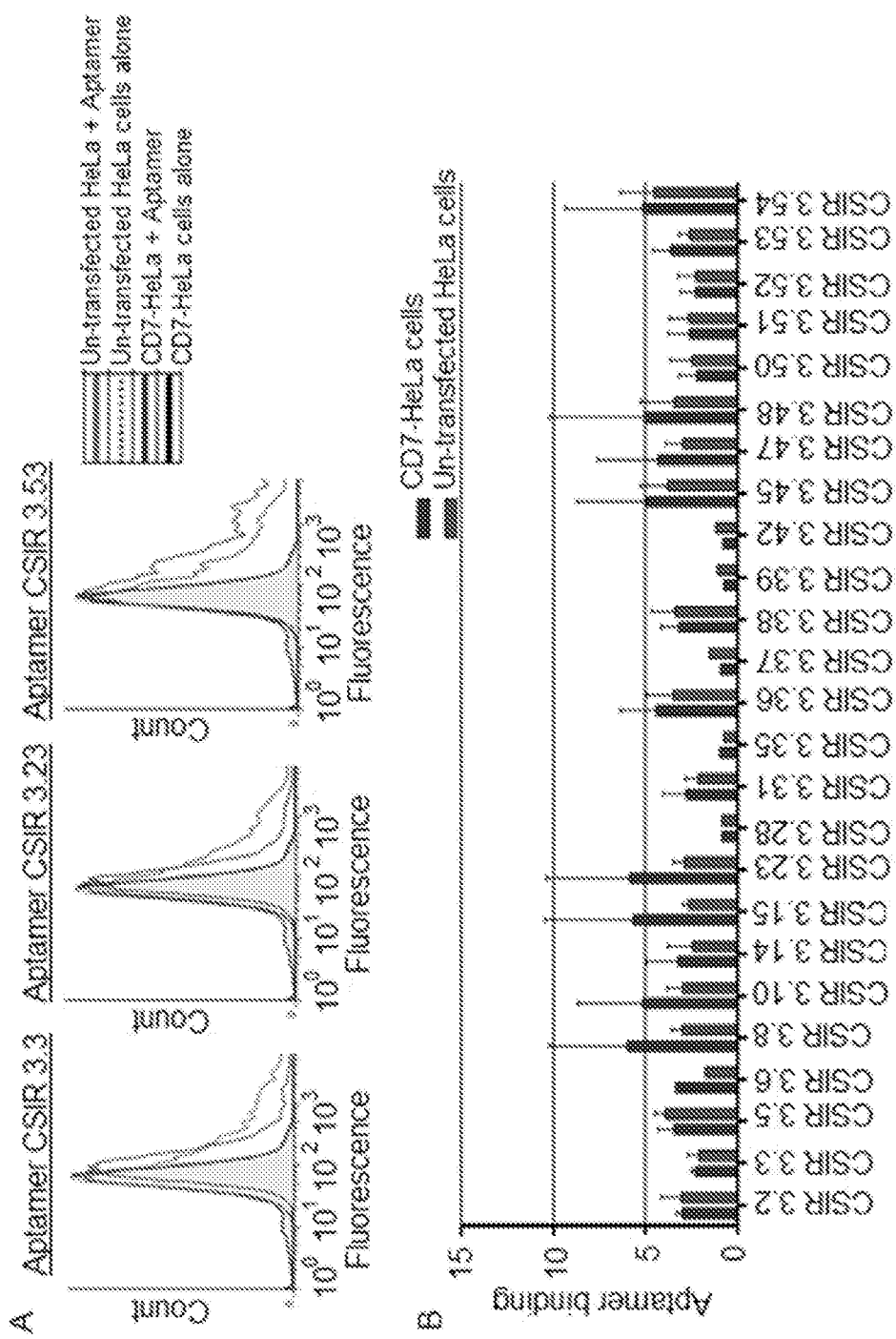
FIG. 9: Aptamer specificity to CD7-HeLa cells over HeLa cells by flow cytometry. A Aptamer CSIR 3.3, CSIR 3.23 and CSIR 3.53 binding to CD7-HeLa and un-transfected HeLa cells. Overlay histogram of aptamer binding different cell types. The cell alone controls are shaded in grey while aptamer binding CD7-HeLa cells and un-transfected HeLa cells are a red and green line respectively. B. Aptamer binding normalised to the cell alone control set to 1 (n=4).

Aptamer binding was seen in a shift in green fluorescence when the aptamer was bound when compared to the cells alone (FIG. 9 A). Aptamer binding was determined for the different cell by normalising the aptamer binding to the cell alone control set to 1. Fourteen aptamers were shown to bind more to CD7-HeLa cells than the HeLa cells (CSIR 3.54, CSIR 3.35, CSIR 3.31, CSIR 3.14, CSIR 3.36, CSIR 3.53, CSIR 3.45, CSIR 3.47, CSIR 3.6, CSIR 3.48, CSIR 3.10, CSIR 3.23, CSIR 3.8 and CSIR 3.15) (FIG. 9 B). The remaining aptamers bound more to HeLa cells than to CD7-HeLa cells (FIG. 9 B).

Figure 10:
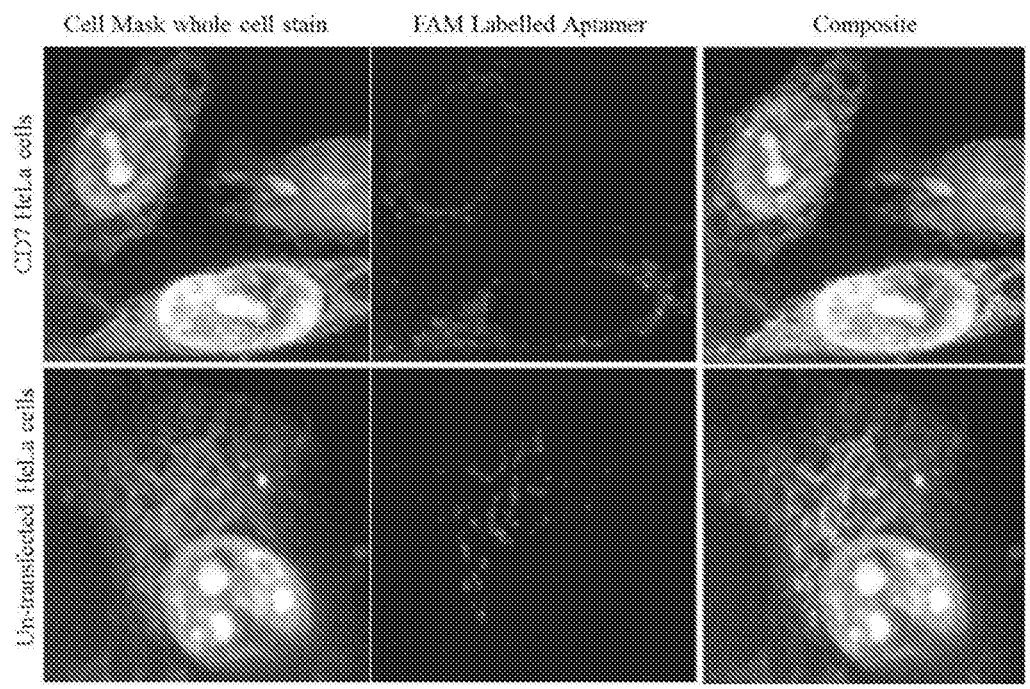
FIG. 10: Aptamer CSIR 3.23 binding specificity. CD7-HeLa and un-transfected HeLa cells were incubated with 20 nM FAM labelled aptamer CSIR 3.23. Cell Mask whole cell satin was used to visualise the cells and localise the aptamer staining. A composite of cell and aptamer stain was generated.
Figure 11:
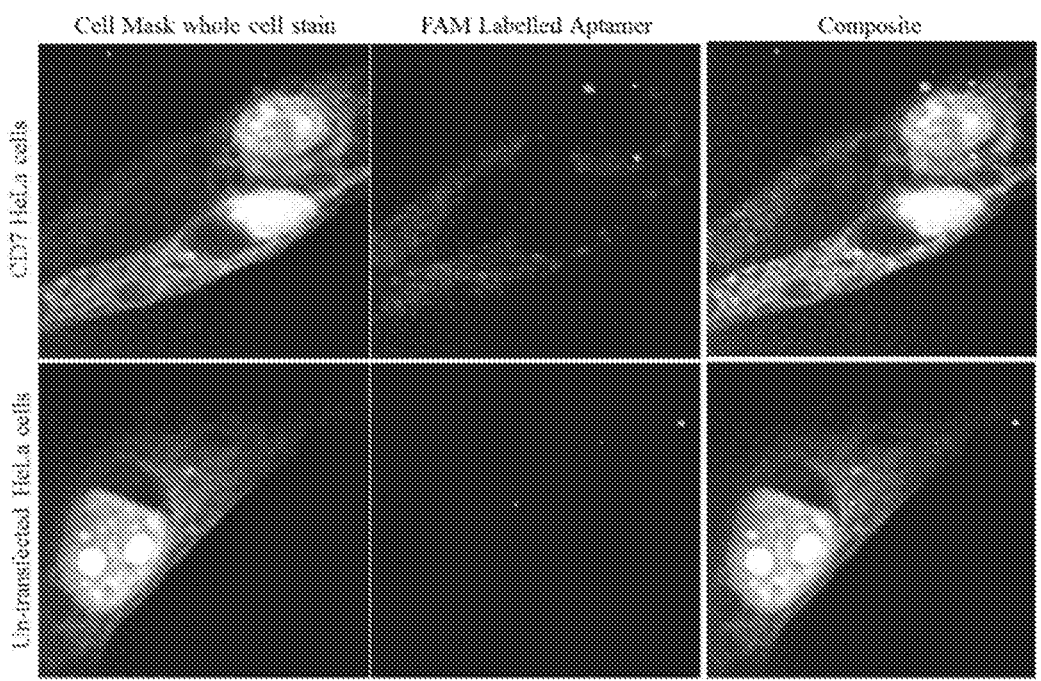
FIG. 11: Aptamer CSIR 3.3 binding specificity. CD7-HeLa and un-transfected HeLa cells were incubated with 20 nM FAM labelled aptamer CSIR 3.3. Cell Mask whole cell satin was used to visualise the cells and localise the aptamer staining. A composite of cell and aptamer stain was generated.
Figure 12:
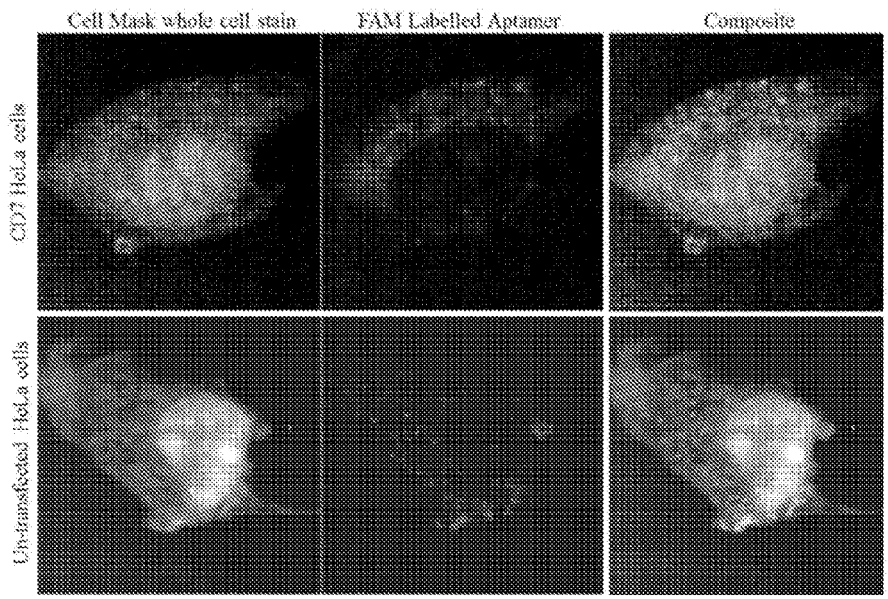
FIG. 12: Aptamer CSIR 3.53 binding specificity. CD7-HeLa and un-transfected HeLa cells were incubated with 20 nM FAM labelled aptamer CSIR 3.53. Cell Mask whole cell satin was used to visualise the cells and localise the aptamer staining. A composite of cell and aptamer stain was generated.

For the confocal microscopy analysis, aptamer CSIR 3.23 showed internalisation specificity for CD7-HeLa cells (FIG. 10) while CSIR 3.3 and CSIR 3.53 did not (FIGS. 11 and 12). Although temperature reduction is a common method for analysing receptor mediated internalisation, there is evidence to suggest that temperature alone can cause fluctuations in aptamer binding affinity (Zhai, 2001). It was shown that for both RNA and DNA aptamers, binding affinity of the aptamer increased with increased temperature. This change was attributed to conformational changes of the aptamer. This same phenomenon may have played a role here in the apparent differences in aptamer CSIR 3.53 specificity at different temperatures.

Figure 13:
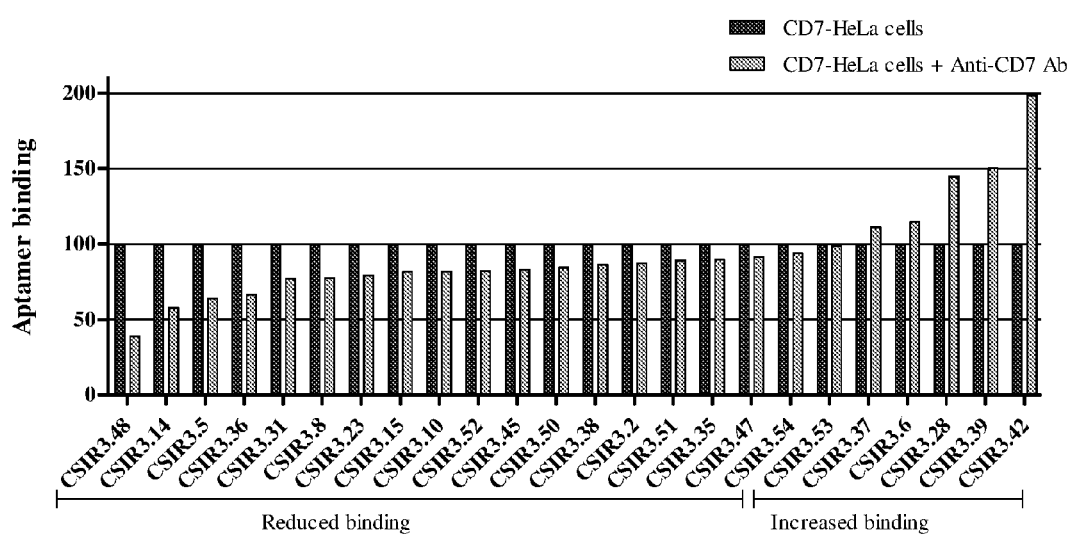
FIG. 13: CD7 aptamer binding comparison in the presence and absence of the anti-CD7 monoclonal antibody competition.

From the antibody blocking analysis, each aptamer binding in the presence of the anti-CD7 antibody was normalised to its CD7-HeLa binding assay set to 100%. Five aptamers (CSIR 3.42, CSIR 3.39, CSIR 3.28, CSIR 3.6, and CSIR 3.37) showed increased binding in the presence of the antibody, one was unchanged (CSIR 3.53) and the remaining aptamers had reduced binding (FIG. 13). All the aptamers found to bind to the CD7-HeLa cells more than the un-transfected HeLa cells had reduced binding in the presence of the antibody except for CSIR 3.53. The reduction in binding may be due to direct competition of the aptamer and antibody for a binding epitope or could be due to conformational changes in the receptor due to antibody binding occluding the aptamer binding epitope. The aptamer that remained unchanged may bind to a different epitope on the protein than the antibody and would be assumed to be unaffected by possible conformational changes due to antibody binding. Those aptamers with increased binding after the anti-CD7 monoclonal antibody may bind to an epitope that is better exposed when the antibody is present.

Aptamer binding to surface expressed CD7 was assessed by flow cytometry. Each aptamer binding in the presence of the anti-CD7 antibody was normalised to its CD7-HeLa binding assay set to 100%. Some aptamer binding was increased while other aptamers showed reduced binding after antibody blocking (n=4). Eight aptamers were selected for further characterisation in Jurkat cells. These included four aptamers blocked by the anti-CD7 monoclonal antibody (an anti-CD7 monoclonal antibody) and considered as specific binders as well as four with increased binding in the presence of the anti-CD7 monoclonal antibody (CSIR 3.42, CSIR 3.28, CSIR 3.37 and CSIR 3.39).

Figure 14:
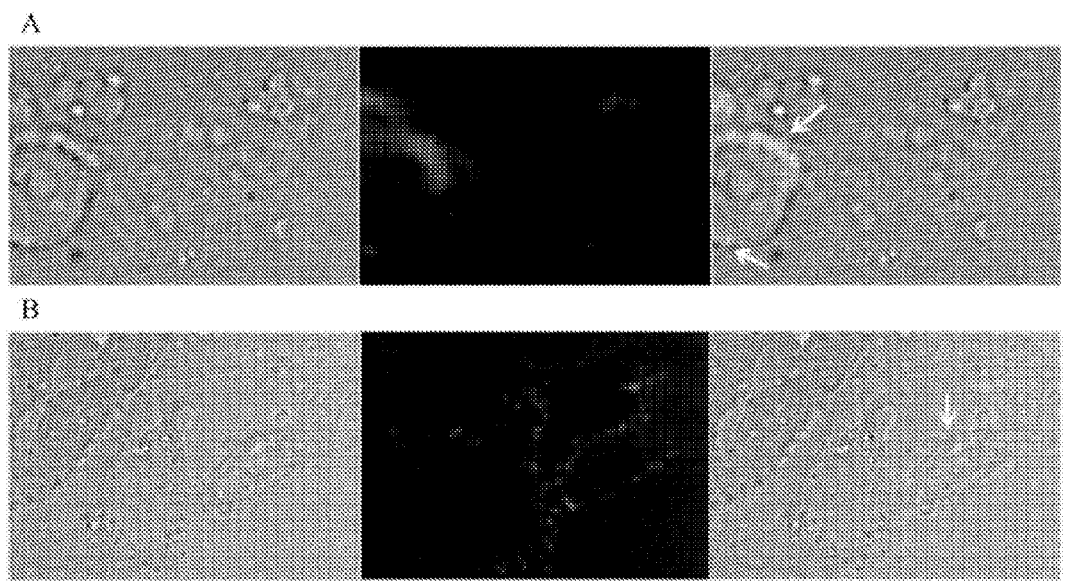
FIG. 14: Microscopy analysis of aptamer CSIR 3.42 binding to CD7 receptor on CD7-HeLa cells. The first panel is a bright field image, the second is the aptamer stain (assigned a pseudo colour, red) and the last panel is the composite of the first two images. A. CD7-HeLa cells incubated with CSIR 3.42 at 4° C. Aptamer staining can be seen localised to the cell periphery (white arrows). B. CD7-HeLa cells were blocked with an anti-CD7 antibody prior to incubation with CSIR 3.42 at 4° C. Aptamer can be seen localised to the periphery of the cells (white arrows).
Figure 15:
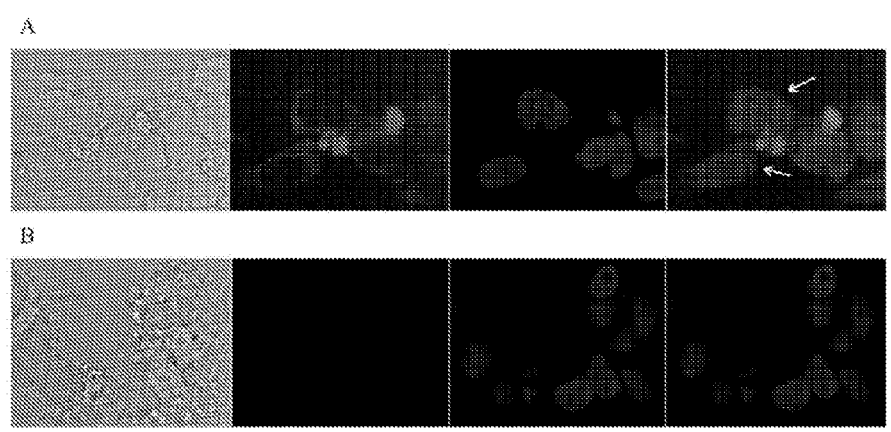
FIG. 15: Microscopy analysis aptamer CSIR 3.42 receptor mediated internalisation into CD7-HeLa cells. Aptamers bound to surface expressed CD7 receptor warmed to 37° C. The first panel is a bright field image, the second is the aptamer stain (assigned a pseudo colour, red); the third panel is the nuclear stain (assigned a pseudo colour, blue) and the last panel is the composite of the aptamer stain and the nuclear stain images. A. CD7-HeLa cells were incubated with CSIR 3.42 for 20 minutes at 4° C., washed and warmed to 37° C. with serum free media. Aptamer staining can be seen localised to the cell interior, surrounding the nucleus (white arrows). B. CD7-HeLa cells were blocked with an anti-CD7 antibody prior to incubation with CSIR 3.42 for 20 minutes at 4° C., washed and warmed to 37° C. with serum free media. No aptamer stain is evident.

Confocal Microscopy Analysis of Anti-CD7 Aptamer Internalisation After Pre-blocking of the CD7 Receptor Aptamer CSIR 3.42 showed the lowest binding to untransfected HeLa cells and the greatest increase in binding in the presence of the anti-CD7 monoclonal antibody. As such, aptamer CSIR 3.42 was assessed to determine if an increase in aptamer internalisation as well as binding is seen in the presence of the antibody. The aptamer CSIR 3.42 was bound to the CD7 receptor at 4° C. to prevent non-specific endocytosis and to ensure that the aptamer bound the receptor. Aptamer binding was competed with an anti-CD7 antibody to have visual confirmation of the flow cytometry analysis. Aptamer CSIR 3.42 bound to CD7-HeLa cells with more intensity in the presence of the anti-CD7 antibody (FIG. 14). This confirmed the aptamer binding in the presence of the anti-CD7 antibody as seen in the flow cytometry analysis. Stained cells were warmed to 37° C. with serum free media and incubated at room temperature for one hour. By warming up the cells, membrane turn over and endocytosis was able to occur. As the cells were washed prior to replacing with media, any weakly bound aptamer or unbound aptamer in solution was removed. This allows for the tracking of only receptor bound aptamer internalisation. Aptamer CSIR 3.42 internalised into the CD7-HeLa cells only when not blocked by the anti-CD7 antibody (FIG. 15). This indicates that although more aptamer binds in the presence of the anti-CD7 antibody is only a weak association and does not improve aptamer internalisation.

Figure 16:
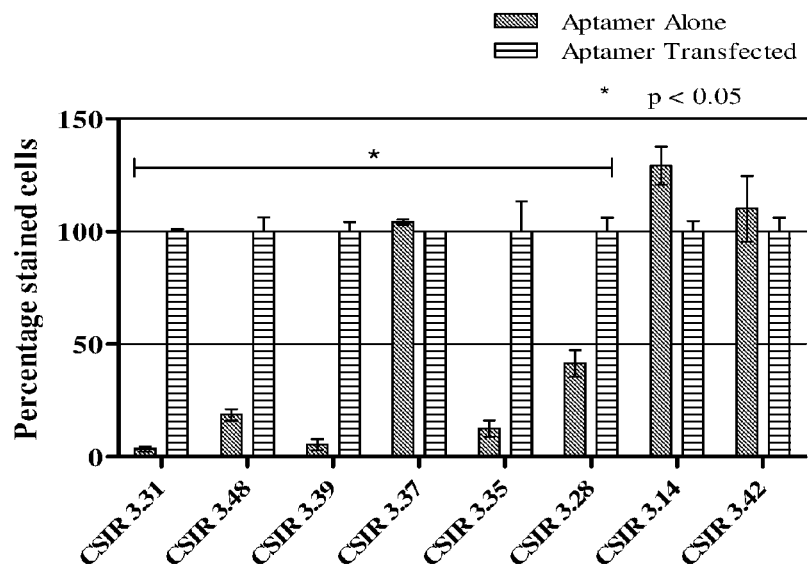
FIG. 16: Aptamer association to endogenously expressed CD7 receptor on Jurkat cells. Association of each aptamer alone was normalised to its respective transfection control (set to 100%). A students t test was used to determine significance (n =2) between the aptamer alone and its transfection control. All aptamers except CSIR 3.14 and CSIR 3.42 were significantly different to their transfection control.

Anti-CD7 Aptamer Internalisation Through Endogenously Expressed Surface CD7 Receptor on Jurkat Cells Eight aptamers (CSIR 3.14, CSIR 3.28, CSIR 3.31, CSIR 3.35, CSIR 3.37, CSIR 3.39, CSIR 3.42 and CSIR 3.48) brought forward from binding studies using the CD7-HeLa recombinant cell line were assessed for internalisation into Jurkat cells endogenously expressing CD7 on the surface by flow cytometry. Aptamers were labelled with cyanine 3 (Cy3) using a Silencer® siRNA Labelling Kit (Ambion, NY, USA) and incubated with Jurkat cells in full media overnight. As the aptamers were incubated with the cells overnight, it was presumed that the aptamers would internalise into the cells rather than only bind to the surface. After the incubation, cells were washed three times before analysis. As such, any weakly surface associated aptamer would have been removed before analysis. However, flow cytometry does not differentiate between surface associated and internalised signal and so this assay was used to determine association of the aptamer to Jurkat cells. Further characterisation of internalisation after association studies would be required to confirm internalisation of the aptamer. As a positive control for internalisation, aptamers were transfected into cells using a lipofectamine based transfection reagent specific for RNA transfection (RNAiMax reagent (Invitrogen, CA, USA). The percentage stained cells was determined by gating cells positive for Cy3 fluorescence when compared to the cells alone control. The maximum transfection efficiency as a percentage of cells stained was around 60% for all aptamers transfected. Each aptamer alone association was normalised to its transfection control set to 100%. A student's t test was conducted to determine a significant difference between the transfection control and the aptamer alone (n=2). CSIR 3.42 and CSIR 3.14 were the only aptamers not significantly different to their transfection control (FIG. 16). Aptamers CSIR 3.14, CSIR 3.42 and CSIR 3.37 had a higher aptamer association than their respective transfection controls and were selected for further characterisation.

Anti-CD7 Aptamer Kinetic Characterisation

Three aptamers (CSIR 3.14, CSIR 3.37 and CSIR 3.42) higher aptamer association than their respective transfection controls and were selected for further characterisation of the association rates and kinetics. The binding characterisation was done with the aptamer concentration kept constant and incubated time altered A non-linear regression line was fit to the data and the association rate and kinetic parameters determined using the equation below:

$$Y = Y\mathrm{max} \times (1 - e^{-kob \cdot X})$$

kob=observed rate constant (min$^{-1}$)
Ymax =maximum Y value (specific binding)
X=time (min)

Non-binding aptamer CSIR 3.31 was included as a negative control to illustrate that aptamers do not non-specifically internalise after a 24 hour incubation period. Aptamer CSIR 3.31 binding did not increase significantly at the maximum incubation period with an increase form 1.97% after six hours to 7.6% after 24 hours; since no association was detected the data could not be plotted. Specific association of aptamers CSIR 3.14, CSIR 3.37 and CSIR 3.42 was calculated as a function of the non-binding aptamer CSIR 3.31 at the same incubation time using the following calculation:

$$\frac{\text{Aptamer percentage shift}}{CSIR\ 3.31\ \text{percentage shift}} \times 100$$

Figure 17:
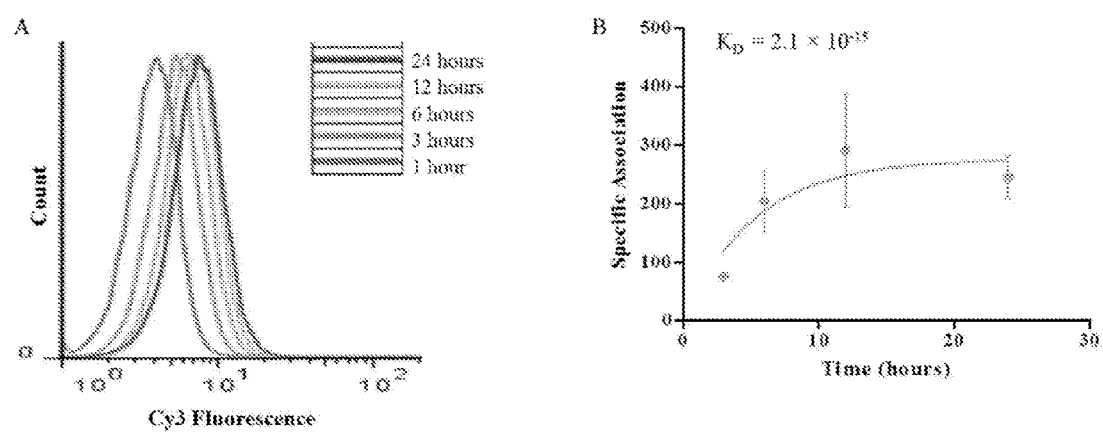
FIG. 17: Time course association of aptamer CSIR 3.14. Aptamer CSIR 3.14 was incubated at a 400 nM final concentration with Jurkat cells for variable times (1 hour, 3 hours, 6 hours, 12 hours and 24 hours). A: Overlay histogram of aptamer binding after different incubation times. Aptamer binding increased with increased incubation times. B: Non-linear regression fit of aptamer binding over time $$\left(\text{Specific Association} = \frac{\text{Aptamer percentage shift}}{CSIR\ 3.31\ \text{percentage shift}} \times 100\right).$$

The percentage shift for all aptamers was determined by gating only the Cy3 stained cells as compared to the cell alone control. Specific association was plotted and a non-linear regression line fit to determine the kinetic parameters. Aptamer CSIR 3.14 showed an increase in Cy3 fluorescence with an increase in incubation time up to six hours (FIG. 17A). The combined analysis from two independent experiments attributed CSIR 3.14 with a dissociation constant of 2.1 fM. The specific association was seen to plateau at the last time points measured and the majority of internalisation occurred within the first two measured time points (FIG. 17B).

Figure 18:
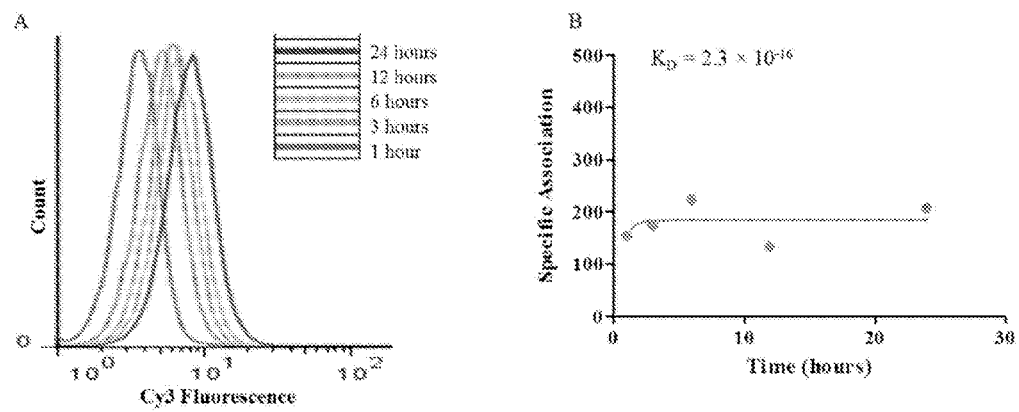
FIG. 18: Time course association of Warner CSIR 3.37. Aptamer CSIR 3.37 was incubated at a 400 nM final concentration with Jurkat cells for variable times (1 hour, 3 hours, 6 hours, 12 hours and 24 hours). A: Overlay histogram of aptamer binding after different incubation times. Aptamer binding increased with increased incubation times. B: Non-linear regression fit of aptamer binding over time $$\left(\text{Specific Association} = \frac{\text{Aptamer percentage shift}}{CSIR\ 3.31\ \text{percentage shift}} \times 100\right).$$

Aptamer CSIR 3.37 showed an increase in Cy3 fluorescence with an increase in incubation time (FIG. 18A). However, much like with CSIR 3.14, when plotted the specific association had plateaued for all later time points measured. Two independent experiments corresponded exactly with no deviation between points (FIG. 18B). The dissociation constant calculated for CSIR 3.37 was 0.23 fM and is evidence for the rapid internalisation of the aptamer before the one hour time point.

Figure 19:
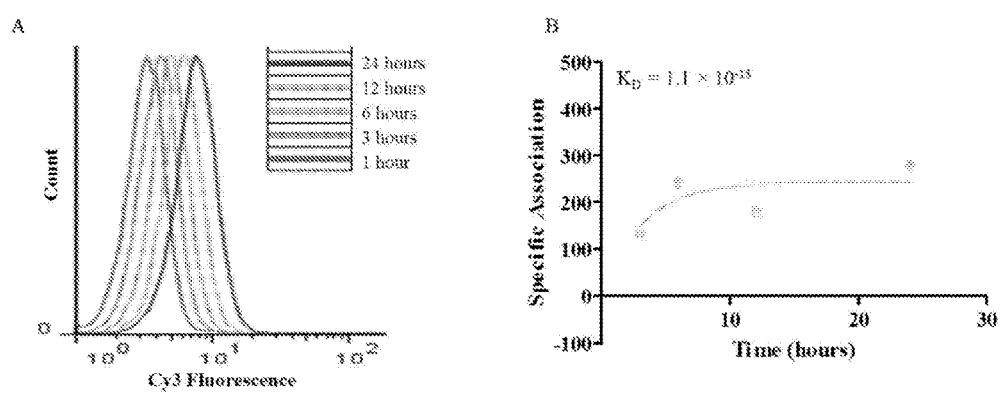
FIG. 19: Time course association of Warner CSIR 3.42. Aptamer CSIR 3.42 was incubated at a 400 nM final concentration with Jurkat cells for variable times (1 hour, 3 hours, 6 hours, 12 hours and 24 hours). A: Overlay histogram of aptamer binding after different incubation times. Aptamer binding increased with increased incubation times. B: Non-linear regression fit of aptamer binding over time $$\left(\text{Specific Association} = \frac{\text{Aptamer percentage shift}}{CSIR\ 3.31\ \text{percentage shift}} \times 100\right).$$

Aptamer CSIR3.42 showed an increase in Cy3 fluorescence with an increase in incubation time (FIG. 19A). When plotted it was evident that, like the previous aptamers, the plateau of aptamer association was reached early on in the incubation times (FIG. 19B). The aptamer dissociation constant was calculated from the non-linear regression fit as 1.1 fM. The maximum association was reached by six hours incubation and was in line with CSIR 3.14 with a similar dissociation constant.

Limit of Detection for Aptamer Association with Jurkat Cells

The kinetic calculations illustrated that aptamer association and thus uptake is rapid and all aptamers tested had dissociation constants in the femtomolar range. However, it was unclear if the rapid plateau was due to the aptamer concentration or the CD7 expression being rate limiting. As such, Jurkat cells were incubated with different concentrations of aptamer CSIR 3.14 and CSIR 3.37 for 12 hours. An increase in binding with increased concentration would indicate that the aptamer concentration was rate limiting while a plateau of binding over 400 nM would indicate saturation of the aptamer binding sites on the cellular CD7 receptors. Lower concentrations were included to determine the limit of detection to compensate for receptor saturation.

Aptamer association was determined as a shift in Cy3 fluorescence when compared to cells alone control. The specific association of aptamer CSIR 3.14, CSIR 3.37 and CSIR 3.42 was calculated as a function of the non-binding aptamer CSIR 3.31 at 12 hours using the following calculation:

$$\frac{\text{Aptamer percentage shift}}{CSIR\ 3.31\ \text{percentage shift}} \times 100$$

Figure 20:
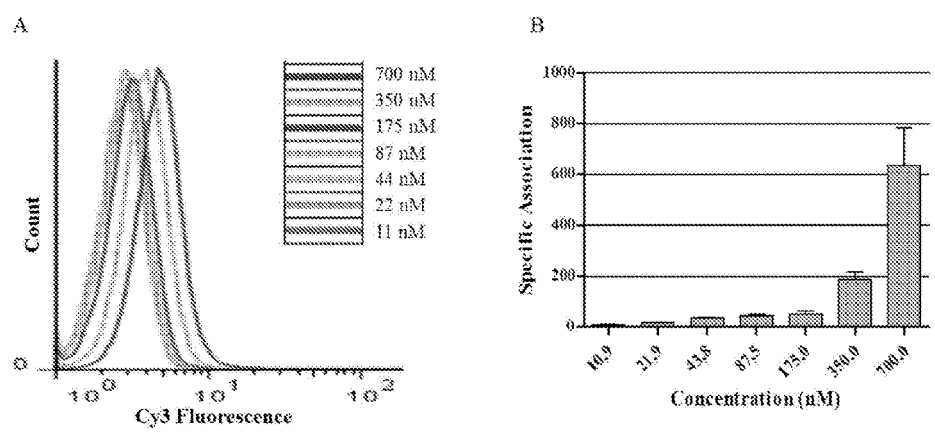
FIG. 20: Binding kinetic analysis of aptamer CSIR 3.14. Aptamer CSIR 3.14 was incubated with Jurkat cells for 12 hours at variable concentrations (11 nM, 22 nM, 44 nM, 87 nM, 175 nM, 350 nM and 700 nM). A. Overlay histogram of aptamer binding at different concentrations. B. Specific association of aptamer to Jurkat cells at different concentrations $$\left(\text{Specific Association} = \frac{\text{Aptamer percentage shift}}{CSIR\ 3.31\ \text{percentage shift}} \times 100\right).$$
Figure 21:
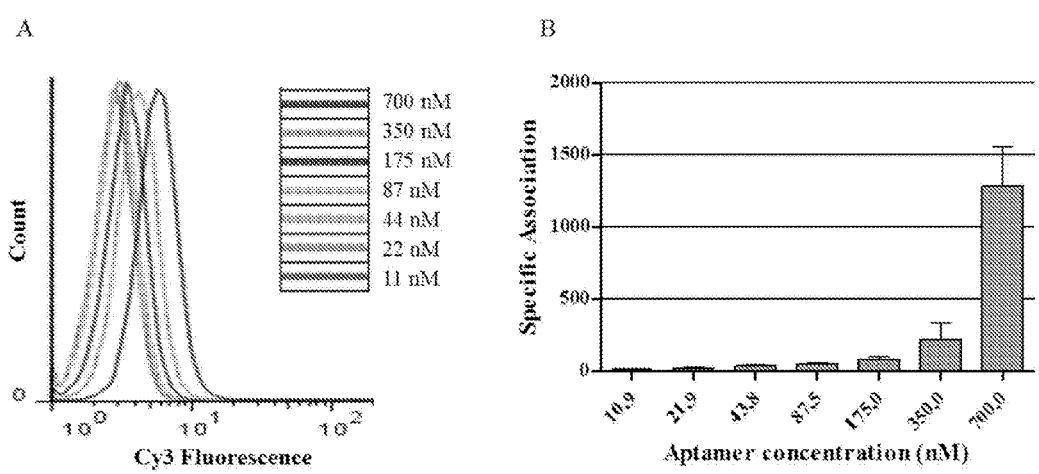
FIG. 21: Binding kinetic analysis of aptamer CSIR 3.37. Aptamer CSIR 3.37 was incubated with Jurkat cells for 12 hours at variable concentrations (11 nM, 22 nM, 44 nM, 87 nM, 175 nM, 350 nM and 700 nM). A. Overlay histogram of aptamer binding at different concentrations. B. Specific association of aptamer to Jurkat cells at different concentrations $$\left(\text{Specific Association} = \frac{\text{Aptamer percentage shift}}{CSIR\ 3.31\ \text{percentage shift}} \times 100\right).$$

Aptamer CSIR 3.14 and aptamer CSIR 3.37 had no detectable binding shift at concentrations under 350 nM (FIG. 20A and FIG. 21A). This was evident when the specific association was calculated as all concentrations below 350 nM had a similar result. Binding increased by 200% with an increase from 350 nM to 700 nM for both aptamers indicating that the aptamer concentration at 400 nM did not saturate all binding sites (FIG. 20B and FIG. 21B).

Aptamer CSIR 3.14 was selected for further characterisation as the kinetics data showed the best fit. Characterisation of aptamer binding by concentration revealed that the plateau reached with the kinetics analysis was due to aptamer depletion and not saturation of the binding sites.

Aptamer CSIR 3.14 Binding Site Mutation Characterisation

Figure 22:
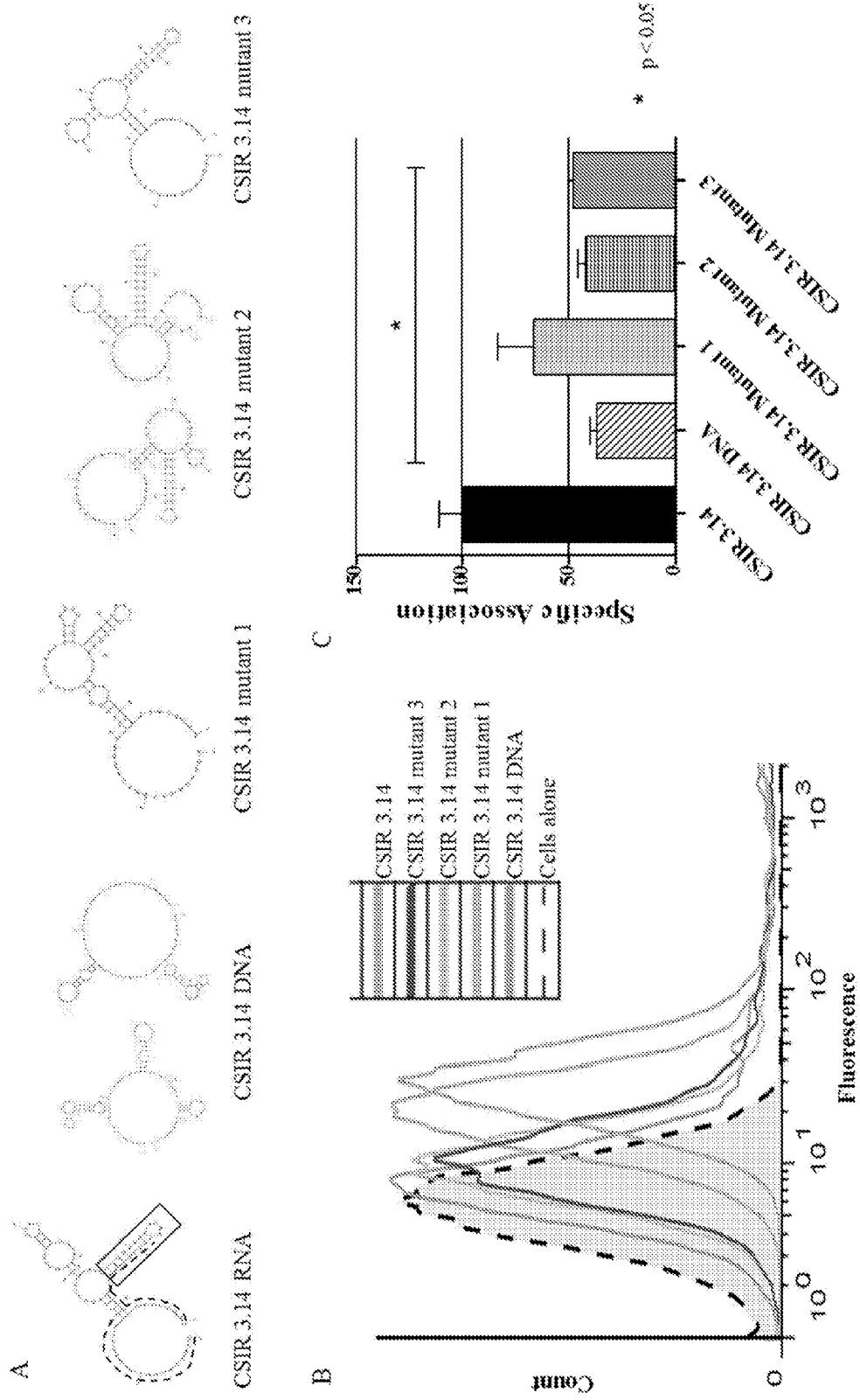
FIG. 22: Association of aptamer CSIR 3.14 full length, mutants and CSIR 3.14 DNA to Jurkat cells. Aptamer CSIR 3.14 RNA, mutants and DNA were incubated with Jurkat cells at a final concentration of 400 nM overnight. A. Computational prediction of aptamer secondary structure, proposed binding region of CSIR 3.14 RNA is indicated by a solid box. B. Overlay histogram of aptamer binding at different concentrations (Cell alone control shaded in grey). C. Specific association of aptamer isoforms to Jurkat cells $$\left(\text{Specific Association} = \frac{\text{Aptamer percentage shift}}{CSIR\ 3.14\ \text{percentage shift}} \times 100\right).$$

Aptamer CSIR 3.14 was mutated to remove ten nucleotide sections of the proposed binding region based on MFold predicted structure analysis. The mutated sequences were analysed by flow cytometry for association to Jurkat cells to determine if the aptamer was still able to bind. In addition, the DNA of aptamer CSIR 3.14 was analysed for binding. Previous studies have reported the use of the DNA form of an RNA aptamer for successful targeted delivery of siRNA (Zhu, 2012 #569). DNA aptamers are intrinsically easier to truncate, as they are not restricted by the 3 regions T7 polymerase promoter. A DNA aptamer can be chemically synthesised at the desired length and tested for activity while the chemical synthesis of RNA is prohibitively expensive. Aptamer secondary structure was predicted for the mutants and the CSIR 3.14 DNA to confirm that the deletion removed the proposed binding structure. All predicted structures did not contain the proposed binding region of CSIR 3.14 (FIG. 22A).

Aptamer association was determined by gating a shift in fluorescence when compared to the cell alone control. Aptamer CSIR 3.14 DNA and mutations were normalised to the full length CSIR 3.14 RNA (set to 100%). A minimal shift in fluorescence was seen for CSIR 3.14 DNA, CSIR 3.14 mutant 2 and CSIR 3.14 mutant 3 while a greater shift was seen for CSIR 3.14 mutant 1 and CSIR 3.14 full length RNA (FIG. 22B). A student's t test was used to determine the significance of the association differences (n =5) and found all mutants and CSIR 3.14 DNA bound significantly less than the full length CSIR 3.14 aptamer ($p<0.05$) (FIG. 22C). Combined these data illustrate the importance of structural conservation in aptamer functioning. This is a characteristic common to aptamers and has been exploited for the generation of aptamers with unique characteristics. An example of this is an aptamer that forms two structures that work synergistically to inhibit their target (Huang, 2009 #561). The DNA isoform of aptamer CSIR 3.14 was not able to bind significantly and so could not be used for truncation optimisation.

Anti-CD7 Aptamer CSIR 3.14 Internalisation Localisation by Confocal Microscopy

Figure 23:
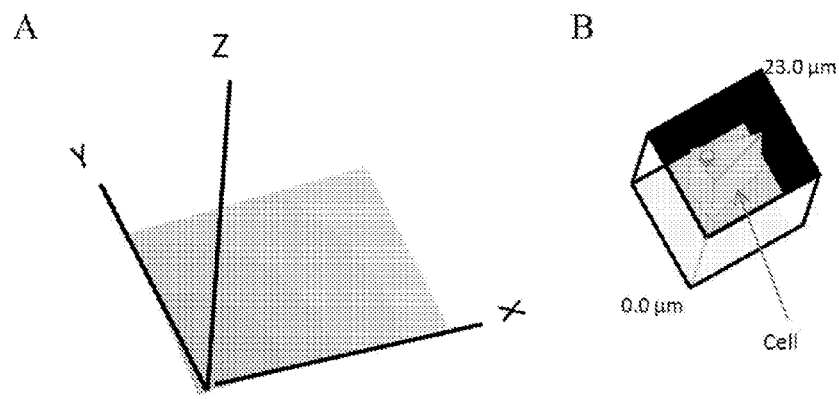
FIG. 23: Z slice through image section by confocal microscopy. A: A diagrammatic representation of the X, Y and Z planes of view. B: A diagrammatic representation of the visible plane dissected every 1 µm to generate a Z stack.

All data up to now have characterised the aptamer interaction with whole cells using flow cytometry. This method, although sensitive, does not differentiate between fluorescence at the cells surface and fluorescence from within the cells. For the cellular localisation of aptamer staining, confocal microscopy was used. Aptamer CSIR 3.14 internalisation was localised by taking images through the cell at 1 μm intervals along the Z axis (FIG. 23A). These images were compiled to generate a Z stack, a compilation of images that dissects the cells visually from below the cell surface, through the cytoplasm to above the top of the cell surface (FIG. 23B).

Figure 24:
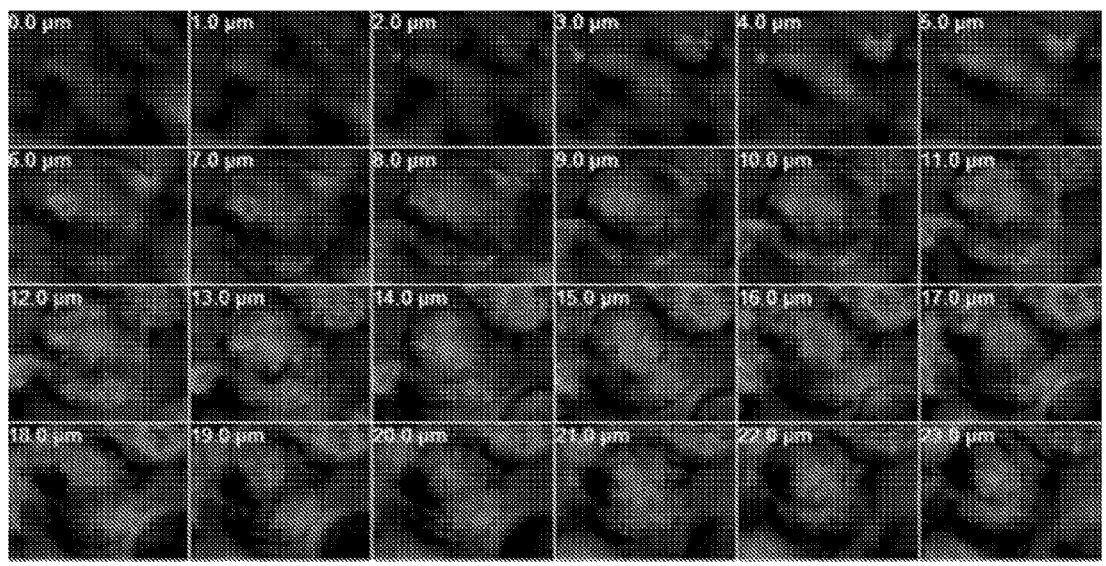
FIG. 24: Image slices through an individual cell along the Z axis for localisation of aptamer CSIR 3.14 Image slices at 1 µm intervals along the Z axis from below the cell to above the cell. The first image at 0.0 µm is below the cell and the final image at 23.0 µm is above the cell. Images between 9.0 µm and 15.0 µm are from within the cell.

At 0.0 μm, below the cell, no fluorescence can be seen (FIG. 24). As the images travel upward through the cell surface (2 μm to 8 μm) some fluorescence becomes evident. Once inside the cell (9 μm to 15 μm) the fluorescence is very bright. The fluorescence dims again as the images are moving through the top of the cell to above the cell (16 μm to 23 μm) (FIG. 24). From this is it clear that the fluorescence associated with the cells is coming from within the cells and thus the aptamer has internalised and is not attached at the cell surface.

Aptamer CSIR 3.14 Kinetics of Internalisation

Figure 25:
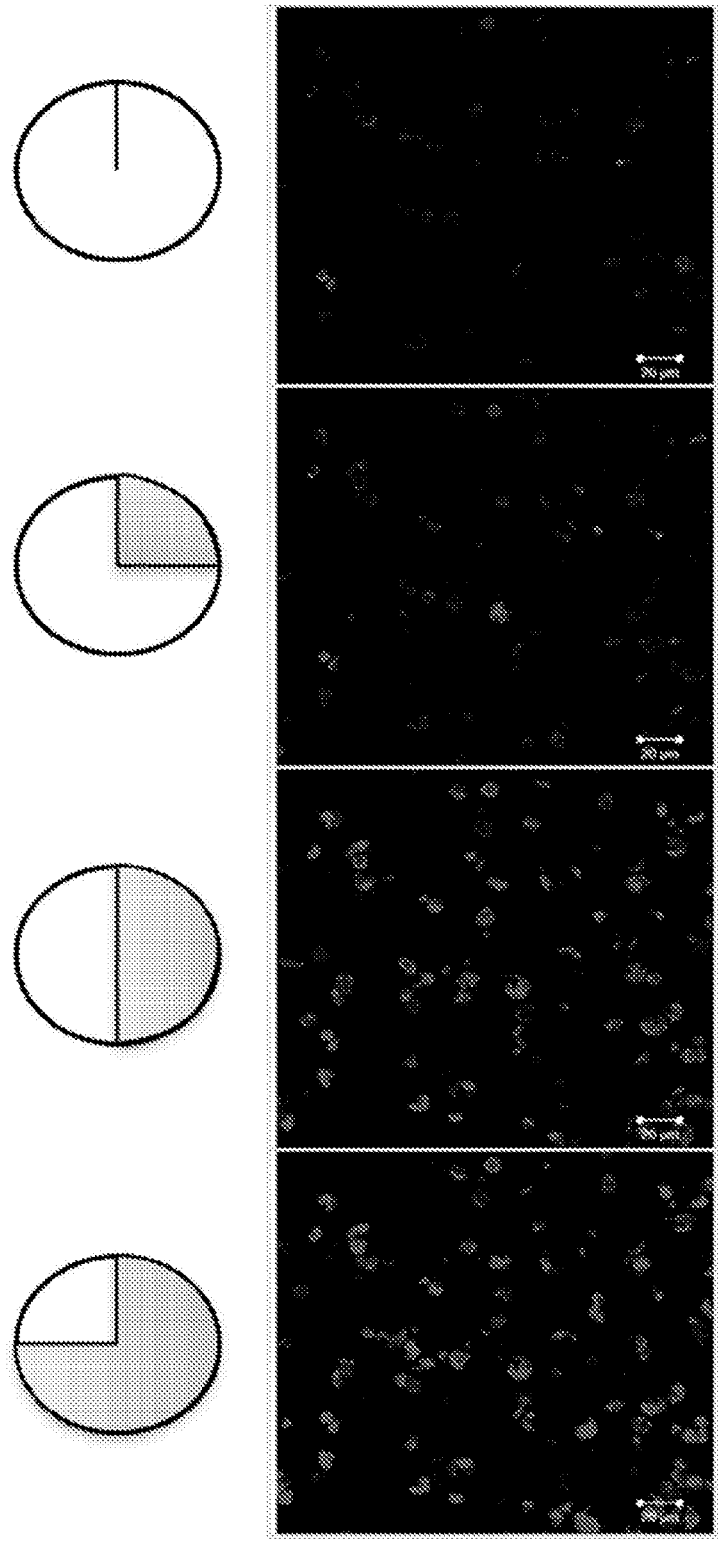
FIG. 25: Time course of aptamer CSIR 3.14 internalisation. Images of aptamer CSIR 3.14 internalisation up to 45 minutes post addition of aptamer. Images were taken at 15 minute intervals for six hours.

Kinetics of aptamer CSIR 3.14 internalisation was determined by confocal microscopy. Images were taken every 15 minutes for six hours and the fluorescence intensity of all cells measured. Aptamer CSIR 3.14 was added to the live cells and the first image recorded shortly after. At the first time point some cells were starting to take up the aptamer (FIG. 25). Cells already saturated at this point may be dead cells that took up the stain due to porous membranes rather than active uptake through the CD7 receptor. An increased number of cells have taken up the stain by the second time point (15 minutes) and at 30 minutes the maximum fluorescence appears to have been reached (FIG. 25). A quantitative analysis of the fluorescence over time was carried out by with the selection of two regions of interest chosen to study. The first region of interest (ROI 1) included the whole visible plane while region of interest two (ROI 2) included only a single cell. The single cell selected was not one that showed fluorescence at time zero but rather one that lit up later. A non-linear regression line was fit to the data and the association rate constant and the dissociation constant was calculated. Both regions showed a plateau of fluorescence intensity within one hour of incubation. This substantiated what was noted visually.

Figure 26:
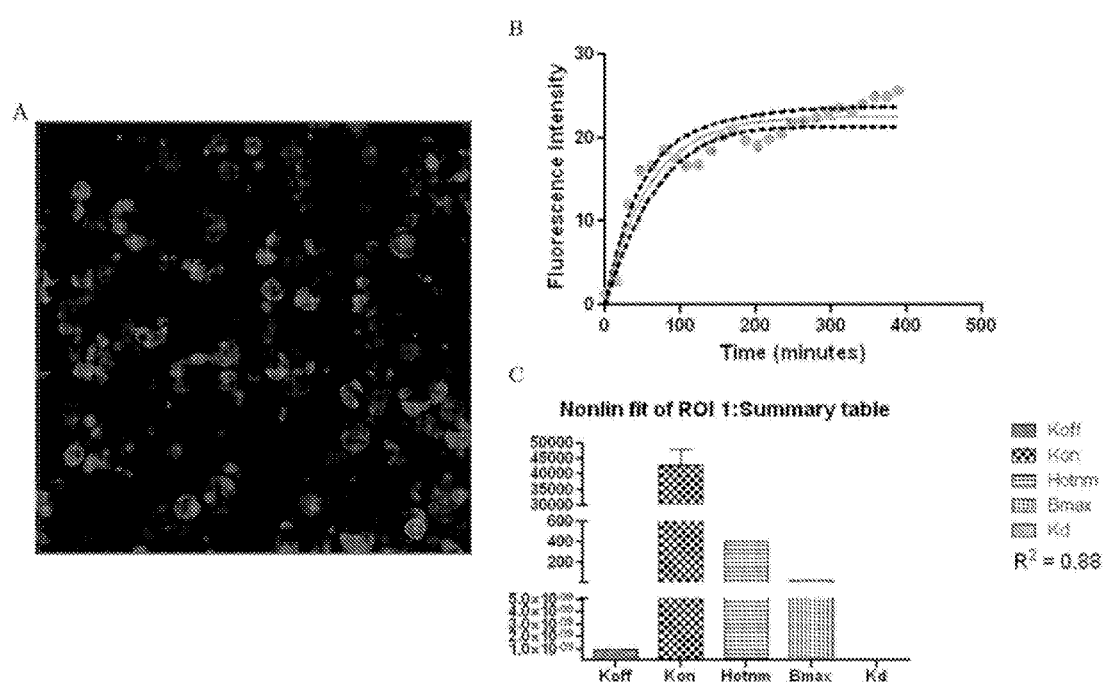
FIG. 26: Kinetics of internalisation within region of interest one (whole visible field). Region of interest one was selected including the whole visible plane for the calculation of internalisation kinetics. A. The area making up ROI 1 B. Fluorescence intensity over time fitted with a non-linear regression line. The 95% confidence interval for the line is indicated by a dashed line. C. The calculation parameters for the non-linear regression line.

The fluorescence intensity per region of interest was plotted and a non-linear regression line fit from which the association rate constant and the dissociation constant was calculated. Even though the cells were attached to the slide surface by Poly-L-Lysine, some cell movement was still recorded. As such, in making use of the whole visible plane for the calculation of the internalisation kinetics, two basic assumptions were made, namely:

1. Cells contributing to the mean fluorescence are those attached to the slide surface
2. Cells drifting in and out of the frame are at a constant and equal rate and have no significant influence on signal accumulation over time The association rate constant for ROI 1 was calculated at $4.2 \times 10^4$ Molar$^{-1}$ Minute$^{-1}$ with a dissociation constant of 23 fM and an $R^2$ of 0.88 (FIG. 26).

Figure 27:
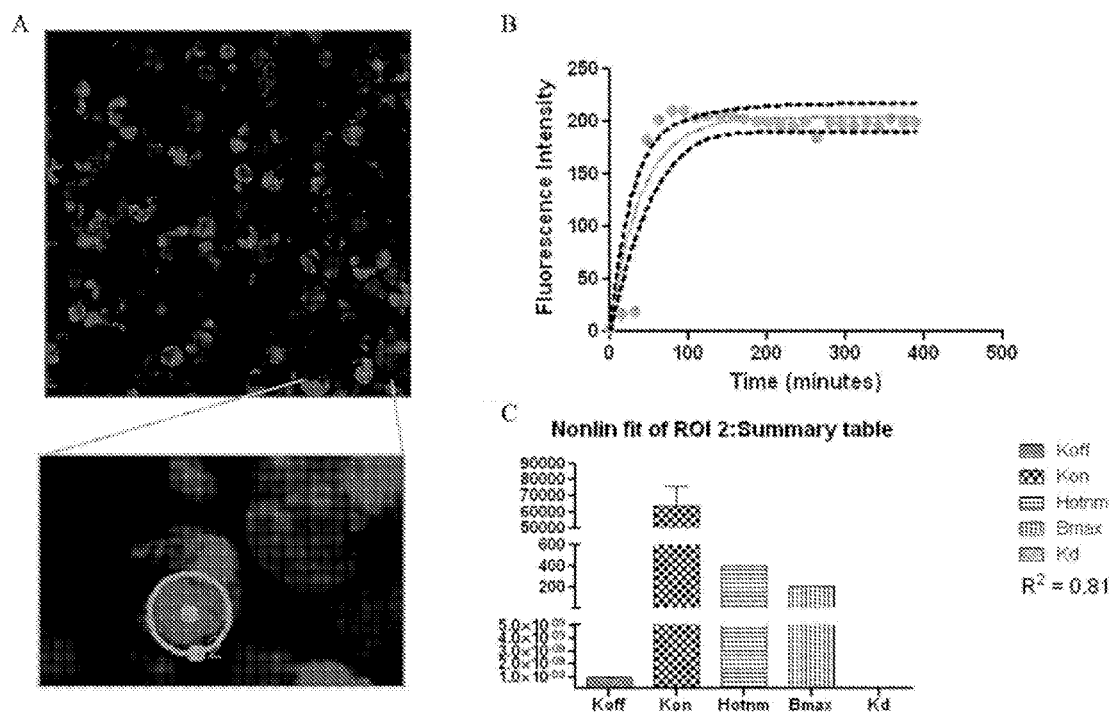
FIG. 27: Kinetics of internalisation within region of interest two (single cell). Region of interest two was selected containing a single cell for the calculation of internalisation kinetics. A. The region making up ROI 2 indicating the single cell in the context of the whole visible plane B. Fluorescence intensity over time fitted with a non-linear regression line. The 95% confidence interval for the line is indicated by a dashed line. C. The calculation parameters for the non-linear regression line.

For the second region of interest (ROI 2), a single cell was selected that did not move over the time period. As with the whole visible plane, the fluorescence within the single cell plateaued within one hour. The association rate constant for ROI 2 was calculated at $6.3 \times 10^4$ Molar$^{-1}$ Minute$^{-1}$ with a dissociation constant of 15 fM (FIG. 27).

Conjugate Formation

Figure 29:
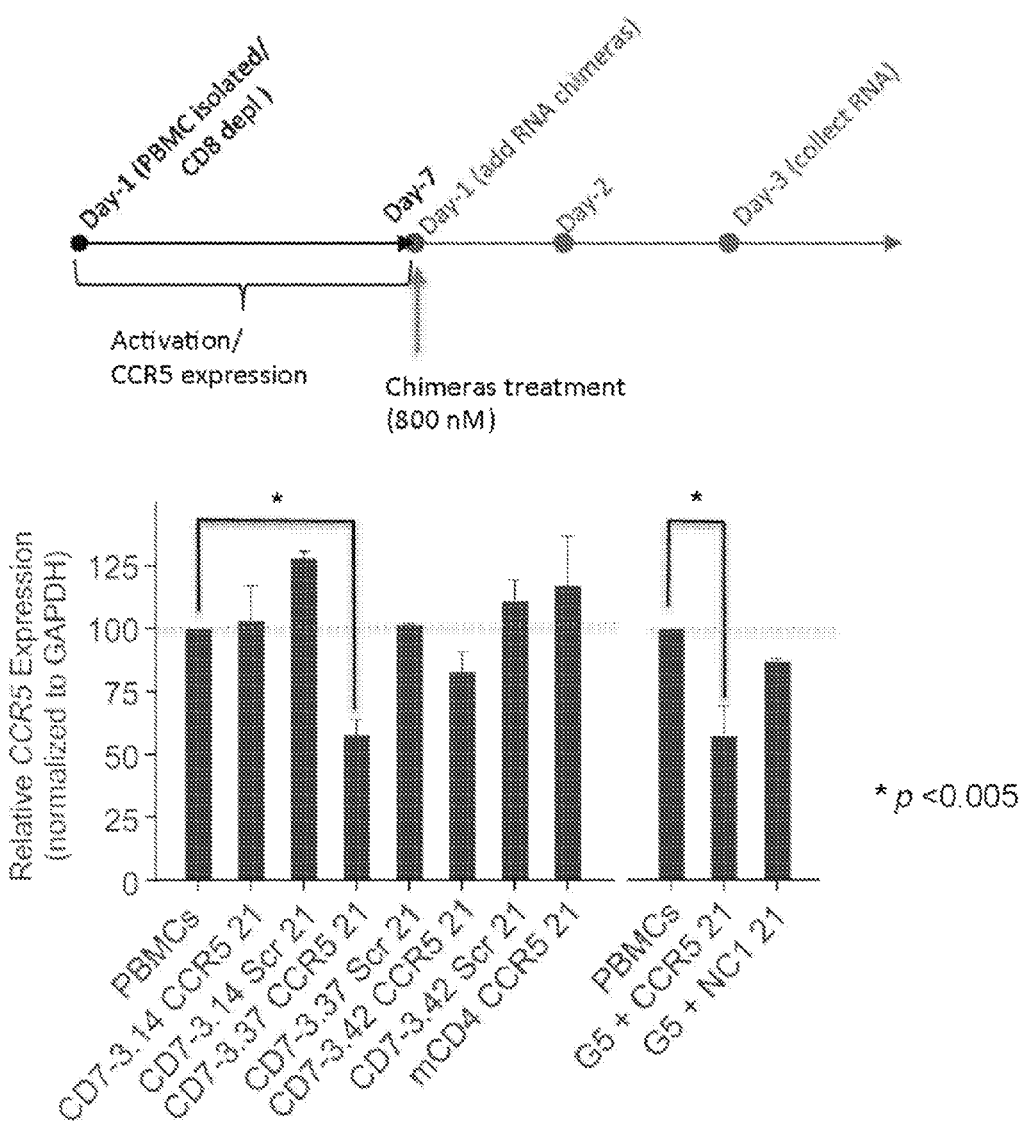
FIG. 29: CEM cells were transfected with aptamer-siRNA chimeras and controls and tested for CCR5 inhibition by qRT-PCR.
Figure 30:
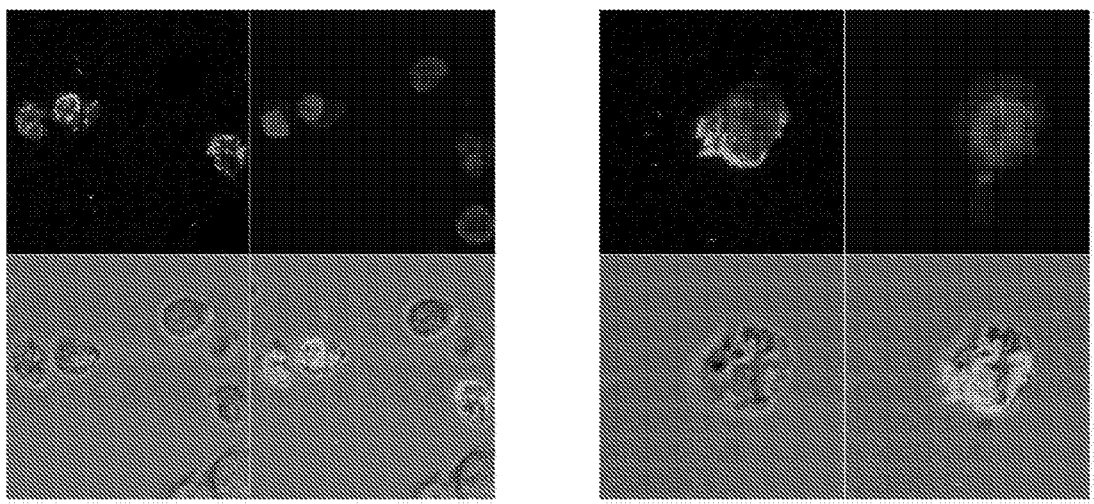
FIG. 30: The cell internalization of CD7 3.37 R5-siRNA in CEM cells. The siRNA was 3'-end labelled with Cy3 fluorophore. 800 nM of aptamer-chimera was administered to CEM cells and visualised by fluorescent microscopy. The nucleus was counterstained with DAPI. The data indicates specific localization of the aptamer-chimera to CEM cells.

The aptamer-siRNA chimera formed from aptamer 3.37 was able to enter T-cells via the CD7 receipt and introduce a gene inhibitor against CCR5 (CD7 3.37 R5-siRNA showed sustained inhibition equivalent to G5-R5-siRNA control (n=3; SEM) (FIG. 29)). The aptamer-siRNA chimera was also able to internalise into CEM cells (FIG. 30).

SUMMARY

A number of aptamers have been identified in clinical development for targeted delivery of various effector molecules. Specifically addressed here are aptamers for targeting T lymphocytes. To the best of the applicant's knowledge, this is the first description of aptamers that specifically target the T lymphocyte receptor CD7. A candidate aptamer has been characterised and found to internalise cells with an average internalisation rate constant of 13±10 fM, six logs smaller than the average nano molar scale rate constants calculated for aptamers.

REFERENCES

Bremmer, E., B. Cate, et al. (2006). "CD7-Restricted Activation of Fas-Mediated Apoptosis: A Novel Therapeutic Approach for Acute T Cell Leukemia." *Blood* 107: 2863-2870.

Cadwell, R. C. and G. F. Joyce (1994). "Mutagenic PCR." *PCR Methods Appl* 3(6): S136-140.

Cotta, A. C., M. L. Cintra, et al. (2006). "Diagnosis of Mycosis Fungoides: A Comparitive Immunohistochemical Study of T Cell Markers Using a Novel Anti-CD7 Antibody." *Applied Immunohistochemistry and Molecular Morphology* 14(3): 291-295.

Dhar, S., Gu, F. X., Langer, R., Farokhzad, O. C., and Lippard, S. J. (2008). "Targeted Delivery of Cisplatin to Prostate Cancer Cells by Aptamer Functionalized Pt(IV) Prodrug-PLGA-PEG Nanoparticles." *Proceedings of the National Academy of Sciences* 105(45): 17356-17361.

Ellington, A. D., and Szostak, J. W. (1990). "In vitro selection of RNA molecules that bind specific ligands." *Nature* 346: 818-822.

Frankel, A. E., J. H. Laver, et al. (1997). "Therapy of Patients with T Cell Lymphomas and Leukemas Using an Anti-CD7 Monoclonal Antibody-Rich Chain Immunotoxin." *Leukemia and Lymphoma* 26(3): 287-298.

Hall, T. A. (1999). "BioEdit: a user-friendly biological sequence alignment editor and analysis program for Windows 95/98/NT. " *Nucl. Acids. Symp. Ser.* 41 95-98.

Hao, Q., J. Zhu, et al. (2001). "Identification of a Novel, Human Multilymphoid Projenitor in Cord Blood." *Blood* 97: 3683-3690.

Huang, Z., W. Pei, et al. (2009). "One RNA aptamer sequence, two structures: a collaborating pair that inhibits AMPA receptors." *Nucleic Acids Res* 37(12): 4022-4032.

Khati, M. (2010). "The future of aptamers in medicine." *Clinical Pathology* 63(6): 480-487.

Khati, M., Schuman, M., Ibrahim, J., Sattentau, Q., Gordon, S., and James, W. (2003). "Neutralisation of Infectivity of Diverse R5 Clinical Isolates of Human Immunodeficiency Virus Type 1 by gp120-Binding 2'F-RNA Aptamers." *Journal of Virology* 77(23): 12692-12698.

Kumar, P., Ban, H., Kim, S., Wu, H., Pearson, T., Greiner, D. L., Laour, A., Yao, J., Haridas, V., Habiro, K., Yang, Y., Jeong, J., Lee, K., Kim, Y., Kim, S. W., Peipp, M., Fey, G. H., Manjunath, N., Shultz, L. D., Lee, S., and Shankar, P. (2008). "T Cell-Specific siRNA Delivery Suppressed HIV-1 Infection in Humanised Mice." *Cell* 134: 577-586.

Lazarovits, A. I., N. Osman, et al. (1994). "CD7 is Associated with CD3 and CD45 on Human T Cells." *Journal of Immunology* 153(9): 3956-3966.

Lobac, D. F., L. L. Hensley, et al. (1985). "Human T Cell Antigen Expression During Early Stages of Fetal Thymic Maturation." *Journal of Immunology* 135(3): 1752-1759.

Man, H.-Y., J. W. Lin, et al. (2000). "Regulation of AMPA Receptor-Mediated Synaptic Transmission by Clathrin-Dependent Receptor Internalization." *Neuron* 25(3): 649-662.

McNamara, J. O., Andrechek, E. R., Wang, Y., Viles, K. D., Rempel, R. E., Gilba, E., Sullenger, B. A., and Giangrande, R. H. (2006). "Cell type-specific delivery of siRNAs with siRNA chimeras." *Nature Biotechnolgy* 24(8): 1005-1015.

Murphy, R. L., and Smith, W. J. (2002). "Switch studies: a review." *Reviews in Antiretroviral Therapy* 3: 146-155.

Neff, C. P., J. Zhou, et al. (2011). "An Aptamer-siRNA Chimera Suppresses HIV-1 Viral Loads and Protects from Helper CD4+ T Cell Decline in Humanized Mice." *Science Translational Medicine* 3(66): 66ra66.

Neves, M. A. D., O. Reinstein, et al. (2010). "Defining a Stem Length-Dependent Binding Mechanism for the Cocaine-Binding Aptamer. A Combined NMR and calorimetry Study." *Biochemistry* 49(39): 8478-8487.

Nguyen, T., R. Pei, et al. (2011). "Label-free microfluidic characterization of temperature-dependent biomolecular interactions." *Biomicrofluidics* 5(3): 34118-341187.

Peipp, M., H. Kupers, et al. (2002). "A Recombinant CD7-Specific Single-Chain Immunotoxin is a Potent Inducer of Apoptosis in Acute Leukemic Cells." *Cancer Research* 62: 2848-2855.

Sempowski, G. D., D. M. Lee, et al. (1999). "Structure and Function of the CD7 Molecule." *Critical Reviews in Immunology* 19(4): 331-348.

Stillwell, R. and B. E. Bierer (2001). "T Cell Signal Transduction and the Role of CD7 in Costimulation." *Immunologic Research* 24(1): 31-52.

Teurk, C. and L. Gold (1990). "Systematic Evolution of Ligands by Exponential Enrichment: RNA Ligands to Bacteriophage T4 DNA Polymerase." *Science* 249: 505-510.

Thiel, K. W., L. I. Hernandez, et al. (2012). "Delivery of chemo-sensitizing siRNAs to HER2+-breast cancer cells using RNA aptamers." *Nucleic Acids Research* 40(13): 6319-6337.

UNAIDS (2009). "AIDS Epidemic Update."

Vallera, D. A., L. J. Burns, et al. (1996). "Laboratory Preparation of a Declosylated Ricin Toxin A Chain Containing Immunotoxin Directed Against a CD7 T Lineage Differentiation Antigen for Phase I Human Clinical Studies Involving T Cell Malignancies." *Journal of Immunological Methods* 197: 69-83.

Waurzyniak, B., E. A. Schneider, et al. (1997). "In vivo Toxicity, Pharmacokinetics and Antileukemic Activity of TXU (Anti-CD7)-Pokeweed Antiviral Protein Immunotoxin." *Clinical Cancer Research* 3: 881-890.

Zhai, G., M. Iskandar, et al. (2001). "Characterization of RNA Aptamer Binding by the Wilms' Tumor Suppressor Protein WT1†." *Biochemistry* 40(7): 2032-2040.

Zhou, J., P. Swiderski, et al. (2009). "Selection, characterisation and application of new RNA HIV gp120 aptamers for facile delivery of Dicer substrate siRNAs into HIV infected cells." *Nucleic Acid research* 37(9): 3094-3109.

Zhu, Q., T. Shibata, et al. (2012). "Inhibition of HIV-1 protease expression in T cells owing to DNA aptamer-mediated specific delivery of siRNA." *Eur J Med Chem.*

The invention claimed is:

1. An aptamer molecule not more than 100 nucleotides in length comprising a nucleotide sequence which is at least 80% identical to the sequence 5' GGGAGA-CAAGAAUAAGCAUG-$R_1$-UUCGACAGGAGGCUCA-CAACAGGC3' (SEQ ID NO: 3),
   wherein $R_1$ is $n_x$ where each n represents any nucleotide and x is an integer from 20 to 55, and
   wherein the aptamer molecule is capable of selectively binding to a cell expressing a CD7 receptor.

2. The aptamer molecule of claim 1, which has a nucleotide sequence which is at least 80% identical to the sequence 5' GGGAGACAAGAAUAAGCAUG-$R_1$-UUCGACAG-GAGGCUCACAACAGG 3' (SEQ ID NO: 123) or 5' GGGAGACAAGAAUAAGCAUG-$R_1$-UUCGACAG-GAGGCUCACAACAG 3' (SEQ ID NO: 124).

3. The aptamer molecule of claim 1, wherein x is from 29 to 55.

4. The aptamer molecule of claim 1, wherein x is from 39 to 55.

5. The aptamer molecule of claim 1, wherein x is from 39 to 49.

6. The aptamer molecule of claim 1, which comprises at least 68 nucleotides.

7. The aptamer molecule of claim 1, which comprises at least 80 nucleotides.

8. The aptamer molecule of claim 1, which consists of from 84 to 90 nucleotides.

9. The aptamer molecule of claim 1, which is at least 90% identical to SEQ ID NO: 3.

10. The aptamer molecule of claim 1, which is at least 95% identical to SEQ ID NO: 3.

11. The aptamer molecule of claim 1, comprising the nucleic acid sequence of SEQ ID NO: 3.

12. The aptamer molecule of claim 1, wherein $R_1$ is:

(SEQ ID NO: 40)
5'-AGAGAUUUGGGAAGGCUCAGGACUGCCUACUAACCCGAUAAGAA-3';

(SEQ ID NO: 6)
5'-GGACCCCAACUAGCGUGUCAUUGUUCGAAUCGACUGAGAUUUCGG G;

(SEQ ID NO: 26)
5'-GAGUGCGUCGCCACUACUCCUCUCAUUACCUCUUGCAUUUCACUA-3';

(SEQ ID NO: 56)
5'-CAGGUCCCACCGCCCCGCUCCCUUAUCAGCUUGGAAUACGUUUUC A-3';

(SEQ ID NO: 4)
5'-AAACCCCAACUCUGGCGCACAUUUCCCCGCCACCACCGUAGAAUA C-3';

(SEQ ID NO: 5)
5'-CCCUUCCCUAGAACGCAGGCAGCAGUUACUCGGAGAACCCUACCC;

(SEQ ID NO: 7)
5'-AGACUGAUCCAAAUACGACACAAAUACCCGGCACUAGACG-3';

(SEQ ID NO: 8)
5'-AGCAUCAAUCUAGACUAGACUCAGAUUACCAGCGAACUAGUGUAU C-3';

(SEQ ID NO: 9)
5'-UAAUUCCAGCAUAAAAAAGAUAGGUACUAUUAAUACACGACCAGA A-3';

(SEQ ID NO: 10)
5'-AUCUACGCGACCACAAAAUUAUCCGCGAUUUGAAUA-3';

(SEQ ID NO: 11)
5'-CCCCUUGCGGUUCCCACAUUAUCUCUCUGCUAUCCCGAUGGCCCG A-3';

(SEQ ID NO: 12)
5'-AGACAUUCUCUCCGCCCUCAACUCCGCCCGCUCCAUCCAGUUCCC U-3';

(SEQ ID NO: 13)
5'-GCCGAUCCAUCCUCCCCACGACCAUCAUGAAUCCCAACAGGAAC-3';

(SEQ ID NO: 14)
5'-GGAUAGUUCUGCGUAGCUUAAGAGAUGUUAAAUCACACCCACGCC A-3';

-continued (SEQ ID NO: 15)
5'-GCUAUCAUACCCGAGACCGCUAUCCCCCACCUUAAUGUUCC-3';

(SEQ ID NO: 16)
5'-AGACCGUACACCUCGCUCGCCAUCCGACUUUGAAUAAGCAUAGACC-3';

(SEQ ID NO: 17)
5'-AGCGCCAAUAUGACCGCGACAUCGUUUGAAUAGUUCCUGGGGAUCU-3';

(SEQ ID NO: 18)
5'-CCGGAUAAGGUCGUCCGUAGUACCGGUUAACGUACCAGCCUUACUC-3';

(SEQ ID NO: 19)
5'-AUCUAAAGACAGAUUUAAUACUACCCGUCGUAUCCAACUCGGAACG-3';

(SEQ ID NO: 20)
5'-UACGUAGACAAGAGAUUUCCAGACCCUGUUACUAAUACAUUUCCCG-3';

(SEQ ID NO: 22)
5'-CUCUGACAAUCCUGCAACAAUUACAUUCAUUAACGGGCUAAUUCAU-3';

(SEQ ID NO: 23)
5'-AUAUGUAGUAACCCCAAUGAUAAAUAACUAAGACCGCAAGUCAGU-3';

(SEQ ID NO: 24)
5'-CCACUCCCACACUUCCUUAAUCCGCGCUAACACACCAUAUGUAC-3';

(SEQ ID NO: 25)
5'-CGUUAGCAGAUACAUCGAGAUUGCAAAGUCCAAUACAGUUAAUAAG-3';

(SEQ ID NO: 27)
5'-CCCCACCCCACUAUUAGCCGAACCCGAACCCCAUCUUACCCGGA-3';

(SEQ ID NO: 28)
5'-UUCUCUGCGGUCUAGGUCACGAUAUACCCGUUACAUAUCAUUCCUG-3';

(SEQ ID NO: 29)
5'-UACAAAUCCGCAUAUACACCCAACCACACCCAAUCCUCUCAGUCCA-3';

(SEQ ID NO: 30)
5'-CCCUAGCAACAUUCUAUGCGCAAACCAUAGUUAUGACUAUUGACUC-3';

(SEQ ID NO: 31)
5'-CACACCGGCUGAGUAUCUGCCUGUGUAAUCGAAACAACUGCGACA-3';

(SEQ ID NO: 32)
5'-CCGCACCCGUACCUCCUUCCUCUCAGGUAUUCACUCACAUCAU-3';

(SEQ ID NO: 33)
5'-CACGGAUGACAGCAGAAUAACUCCUACAGUCCAUAUAUAAACGAUU-3';

(SEQ ID NO: 34)
5'-CAAUUUAUCGAGACCCAGAUAACCGAUUUAUACGCAGACGAUAAGU-3';

(SEQ ID NO: 35)
5'-AGCCCCACAUCCUACGCCACUCACCCACGCAUCCCGAUUGAUCAAA-3';

(SEQ ID NO: 36)
5'-GGGAUAGCCGCACUUCUCACAGGAGUCGAGUCUUUUGAUCGGUCUC-3';

(SEQ ID NO: 37)
5'-CGUGCGCCUAUGAUGAGUCUGGUUCACAUAAUUUGCGUUAGUUAGU-3';

(SEQ ID NO: 39)
5'-GGCAGCGAUAGACUGUUAACUACAGACGGGAGUCCGCGU-3';

(SEQ ID NO: 41)
5'-CAUCCCCAGGCUCUUCCAUCAAGCAAUUAAUACAAUCACAACCCCC-3';

(SEQ ID NO: 42)
5'-UUAGCUCCGUCAGGUAUCCACAGAUCAUUGUUCAAUACA-3';

(SEQ ID NO: 43)
5'-CCAUGAUAUACCGAUAUUAACUUCCGCGUUGCACAAGAAUACACUG-3';

(SEQ ID NO: 44)
5'-CGAAAUCAUAGCCCACGGUUGCAUCACCCGUUCUGAUCAUAUACUUAAA-3';

(SEQ ID NO: 45)
5'-CGUCCCACACCCUCCGAUUCCGACCAGGACUGGAUACUUACACUUU-3';

(SEQ ID NO: 46)
5'-CCCCCUUCGCCCAAAACAUAUCGCUUCGACCUUCCACACCCUAUCA-3';

(SEQ ID NO: 47)
5'-UUCCUGGAGACGCCUAUAGUACCUUGCCCCGUAGUAUCUGAUCAA-3';

(SEQ ID NO: 48)
5'-UUACCUACAAAAAAGAAAAAGAAUUAAACGGAUUAAGAAGGGGAAGUAGUUC-3';

(SEQ ID NO: 49)
5'-AUUGAGCCCUCCGCCCAAACUCACUCUCAACAAACCGCUGGAACGC-3';

(SEQ ID NO: 50)
5'-ACCGUGCUCUGUGACAGGACUUUACUUAGGGAUAAGGGUUGAAAC-3';

(SEQ ID NO: 51)
5'-CUGGCAAUAAACGGCUAUAAGUAAAG-3';

(SEQ ID NO: 52)
5'-CAAAAUAUACAAAUAACAGACAGAAUACUUUGCAUCAAUAGUUGGA-3';

(SEQ ID NO: 53)
5'-CGCGCAUAAACCUAACGCGCUUUUCUCUAGGUUGAUUAAACUGGG-3';

(SEQ ID NO: 54)
5'-AGCAGAUGUUGUGAUUAGUUGAACAAGGUCCCCAAACAUUGGAGGA-3';

(SEQ ID NO: 55)
5'-CCUCAUUAACCCCGCUGUGCCCUGCAUCACUUCUCUAUAGUCCGACA-3';
or (SEQ ID NO: 57)
5'-UCAUCUCACCGCCAUAAUCCUCAACAUUCUCCCCACCCGAUUCCCG-3'.

13. The aptamer molecule of claim 1, which has the nucleic acid sequence:

(SEQ ID NO: 94)
5'-GGGAGACAAGAAUAAGCAUGAGAGAUUUUGGGAAGGCUCAGGACUGCCUACUAACCCGAUAAGAAUUCGACAGGAGGCUCACAACAGGG-3';

(SEQ ID NO: 60)
5'-GGGAGACAAGAAUAAGCAUGGGACCCCAACUAGCGUGUCAUUGUUCGAAUCGACUGAGAUUUCGGGUUCGACAGGAGGCUCACAACAGGC;

-continued (SEQ ID NO: 80)
5'-GGGAGACAAGAAUAAGCAUGGAGUGCGUCGCCACUACUCCUCUCA
UUACCUCUUGCAUUUCACUAUUCGACAGGAGGCUCACAACAGGC-3';

(SEQ ID NO: 110)
5'-GGGAGACAAGAAUAAGCAUGCAGGUCCCACCGCCCCGCUCCCUUA
UCAGCUUGGAAUACGUUUUCAUUCGACAGGAGGCUCACAACAGGC-3';

(SEQ ID NO: 58)
5'-GGGAGACAAGAAUAAGCAUGAAACCCCAACUCUGGCGCACAUUUCC
CCGCCACCACCGUAGAAUACUUCGACAGGAGGCUCACAACAGGC-3';

(SEQ ID NO: 59)
5'-GGGAGACAAGAAUAAGCAUGCCCUUCCCUAGAACGCAGGCAGCAGU
UACUCGGAGAACCCUACCCUUCGACAGGAGGCUCACAACAG;

(SEQ ID NO: 61)
5'-GGGAGACAAGAAUAAGCAUGAGACUGAUCCAAAUACGACACAAAUA
CCCGGCACUAGACGUUCGACAGGAGGCUCACAACAGGC-3';

(SEQ ID NO: 62)
5'-GGGAGACAAGAAUAAGCAUGAGCAUCAAUCUAGACUCAGAU
UACCAGCGAACUAGUGUAUCUUCGACAGGAGGCUCACAACAGGC-3';

(SEQ ID NO: 63)
5'-GGGAGACAAGAAUAAGCAUGUAAUUCCAGCAUAAAAAAGAUAGGUA
CUAUUAAUACACGACCAGAAUUCGACAGGAGGCUCACAACAGGC-3';

(SEQ ID NO: 64)
5'-GGGAGACAAGAAUAAGCAUGAUCUACGCGACCACAAAAUUAUCCGC
GAUUUGAAUAUUCGACAGGAGGCUCACAACAGGC-3';

(SEQ ID NO: 65)
5'-GGAGACAAGAAUAAGCAUGCCCCUUGCGGUUCCCACAUUAUCUCUC
UGCUAUCCCGAUGGCCCGAUUCGACAGGAGGCUCACAACAGGC-3';

(SEQ ID NO: 66)
5'-GGGAGACAAGAAUAAGCAUGAGACAUUCUCUCCGCCCUCAACUCCGC
CCGCUCCAUCCAGUUCCUGUCGACAGGAGGCUCACAACAGGC-3';

(SEQ ID NO: 67)
5'-GGGAGACAAGAAUAAGCAUGGCCGAUCCAUCCUCCCCACGACCAUC
AUGAAUCCCAACAGGAACUUCGACAGGAGGCUCACAACAGGC-3';

(SEQ ID NO: 68)
5'-GGGAGACAAGAAUAAGCAUGGGAUAGUUCUGCGUAGCUUAAGAGAUG
UUUAAAUCACACCCACGCCAUUCGACAGGAGGCUCACAACAGGC-3';

(SEQ ID NO: 69)
5'-GGGAGACAAGAAUAAGCAUGGCUAUCAUACCCGAGACCGCUAUCCCC
CACCUUAAUGUUCCUUCGACAGGAGGCUCACAACAGGC-3';

(SEQ ID NO: 70)
5'-GGGAGACAAGAAUAAGCAUGAGACCGUACACCUCGCUCGCCAUCCG
ACUUUGAAUAAGCAUAGACCUUCGACAGGAGGCUCACAACAGGC-3';

(SEQ ID NO: 71)
5'-GGGAGACAAGAAUAAGCAUGAGCGCCAAUAUGACCGCGACAUCGUUU
GAAUAGUUCCUGGGGAUCUUUCGACAGGAGGCUCACAACAGG-3';

(SEQ ID NO: 72)
5'-GGGAGACAAGAAUAAGCAUGCCGGAUAAGGUCGUCCGUAGUACCGGU
UAACGUACCAGCCUUACUCUUCGACAGGAGGCUCACAACAGGC-3';

(SEQ ID NO: 73)
5'-GGGAGACAAGAAUAAGCAUGAUCUAAAGACAGAUUUAAUACUACCCG
UCGUAUCCAACUCGGAACGGUCGACAGGAGGCUCACAACAGGC-3';

(SEQ ID NO: 74)
5'-GGGAGACAAGAAUAAGCAUGUACGUAGACAAGAGAUUUCCAGACCCU
GUUACUAAUACAUUUCCCGUUCGACAGGAGGCUCACAACAGGC-3';

(SEQ ID NO: 76)
5'-GGGAGACAAGAAUAAGCAUGCUCUGACAAUCCUGCAACAAUUACAU
UCAUUAACGGGCUAAUUCAUAUCGACAGGAGGCUCACAACAGGC-3';

(SEQ ID NO: 77)
5'-GGGAGACAAGAAUAAGCAUGAUAUGUAGUAACCCCAAUGAUAAAUAA
CUAAGACCGCAAGUCAGUUCGACAGGAGGCUCACAACAGGC-3';

(SEQ ID NO: 78)
5'-GGGAGACAAGAAUAAGCAUGCCACUCCCACACUUCCUUAAUCCGCG
CUAACACACCAUAUGUACUUCGACAGGAGGCUCACAACAGGC-3';

(SEQ ID NO: 79)
5'-GGGAGACAAGAAUAAGCAUGCGUUAGCAGAUACAUCGAGAUUGCAA
AGUCCAAUACAGUUAAUAAGUUCGACAGGAGGCUCACAACAGGC-3';

(SEQ ID NO: 81)
5'-GGGAGACAAGAAUAAGCAUGCCCCACCCCACUAUUAGCCGAACCC
GAACCCCAUCUUACCCGGACCCGACAGGAGGCUCACAACAGGC-3';

(SEQ ID NO: 82)
5'-GGGAGACAAGAAUAAGCAUGUUCUCUGCGGUCUAGGUCACGAUAU
ACCCGUUACAUAUCAUUCCUGUUCGACAGGAGGCUCACAACAGGC-3';

(SEQ ID NO: 83)
5'-GGGAGACAAGAAUAAGCAUGUACAAAUCCGCAUAUACACCCAACCA
CACCCAAUCCUCUCAGUCCAUUCGACAGGAGGCUCACAACAGGC-3';

(SEQ ID NO: 84)
5'-GGGAGACAAGAAUAAGCAUGCCCUAGCAACAUUCUAUGCGCAAACC
AUAGUUAUGACUAUUGACUCUUCGACAGGAGGCUCACAACAGGC-3';

(SEQ ID NO: 85)
5'-GGGAGACAAGAAUAAGCAUGCACACCGGCUGAGUAUCUGCCUGUGU
AAUCGAAACAACUGCGACAUUCGACAGGAGGCUCACAACAGGC-3';

(SEQ ID NO: 86)
5'-GGGAGACAAGAAUAAGCAUGCCGCACCCGUACCUCCUUCCUCUCAG
GUAUUCACUCACAUCAUUUCGACAGGAGGCUCACAACAGG-3';

(SEQ ID NO: 87)
5'-GGGAGACAAGAAUAAGCAUGCACGGAUGACAGCAGAAUAACUCCUA
CAGUCCAUAUAUAAACGAUUUUCGACAGGAGGCUCACAACAGGC-3';

(SEQ ID NO: 88)
5'-GGGAGACAAGAAUAAGCAUGCAAUUUAUCGAGACCCAGAUAACCGAU
UUAUACGCAGACGAUAAGUUUCGACAGGAGGCUCACAACAGGC-3';

(SEQ ID NO: 89)
5'-GGGAGACAAGAAUAAGCAUGAGCCCCACAUCCUACGCCACUCACCC
ACGCAUCCCGAUUGAUCAAAUUCGACAGGAGGCUCACAACAGGC-3'

(SEQ ID NO: 90)
5'-GGGAGACAAGAAUAAGCAUGGGGAUAGCCGCACUUCUCACAGGAGU
CGAGUCUUUUGAUCGGUCUCUUCGACAGGAGGCUCACAACAGGC-3';

(SEQ ID NO: 91)
5'-GGGAGACAAGAAUAAGCAUGCGUGCGCCUAUGAUGAGUCUGGUUCA
CAUAAUUUGCGUUAGUUAGUUUCGACAGGAGGCUCACAACAGGC-3';

(SEQ ID NO: 93)
5'-GGGAGACAAGAAUAAGCAUGGGCAGCGAUAGACUGUUAACUACAGA
CGGGAGUCCGCGUUUCGACAGGAGGCUCACAACAGGC-3';

(SEQ ID NO: 95)
5'-GGGAGACAAGAAUAAGCAUGCAUCCCCAGGCUCUUCCAUCAAGCAA
UUAAUACAAUCACAACCCCUUCGACAGGAGGCUCACAACAGGC-3';

(SEQ ID NO: 96)
5'-GGGAGACAAGAAUAAGCAUGUUAGCUCCGUCAGGUAUCCACAGAUC
AUUGUUCAAUACAUUCGACAGGAGGCUCACAACAGGC-3';

(SEQ ID NO: 97)
5'-GGGAGACAAGAAUAAGCAUGCCAUGAUAUACCGAUAUUAACUUCCGC
GUUGCACAAGAAUACACUGUUCGACAGGAGGCUCACAACAGGC-3';

(SEQ ID NO: 98)
5'-GGGAGACAAGAAUAAGCAUGCGAAAUCAUAGCCCACGGUUGCAUCAC
CCGUUCUGAUCAUAUACUUAAAGUUAGGAGGCUCACAACAGGC-3';

(SEQ ID NO: 99)
5'-GGGAGACAAGAAUAAGCAUGCGUCCCACACCCUCCGAUUCCGACCA
GGACUGGAUACUUACACUUUUUCGACAGGAGGCUCACAACAGGC-3';

(SEQ ID NO: 100)
5'-GGGAGACAAGAAUAAGCAUGCCCCUUCGCCCAAAACAUAUCGCUU
CGACCUUCCACACCCUAUCAUUCGACAGGAGGCUCACAACAGGC-3';

(SEQ ID NO: 101)
5'-GGGAGACAAGAAUAAGCAUGUUCCUGGAGACGCCUAUAGUACCUUG
CCCCGUAGUAUCUGAUCAAUUCGACAGGAGGCUCACAACAGGC-3';

(SEQ ID NO: 102)
5'-GGGAGACAAGAAUAAGCAUGUUACCUACAAAAAAGAAAAAGAAUUA
AACGGAUUAAGAAGGGGAAAAAGUAGUUCGACAGGAGGCUCACAACAG
GC-3';

(SEQ ID NO: 103)
5'-GGGAGACAAGAAUAAGCAUGAUUGAGCCCUCCGCCCAAACUCACUC
UCAACAAACCGCUGGAACGCUUCGACAGGAGGCUCACAACAGGC-3';

(SEQ ID NO: 104)
5'-GGGAGACAAGAAUAAGCAUGACCGUGCUCUGUGACAGGACUUUACU
UAGGGAUAAGGGUUGAAACUUCGACAGGAGGCUCACAACAGGC-3';

(SEQ ID NO: 105)
5'-GGGAGACAAGAAUAAGCAUGCUGGCAAUAAACGGCUAUAAGUAAA
GUUCGACAGGAGGCUCACAACAGGC-3';

(SEQ ID NO: 106)
5'-GGGAGACAAGAAUAAGCAUGCAAAAUAUACAAAUAACAGACAGA
AUACUUUGCAUCAAUAGUUGGAUUCGACAGGAGGCUCACAACAGG
C-3';

(SEQ ID NO: 107)
5'-GGGAGACAAGAAUAAGCAUGCGCGCAUAAACCUAACGCGCUUUUCU
CUAGGUUGAUUAAACUGGGUUCGACAGGAGGCUCACAACAGGC-3';

(SEQ ID NO: 108)
5'-GGGAGACAAGAAUAAGCAUGAGCAGAUGUUGUGAUUAGUUGAACA
AGGUCCCCAAACAUUGGAGGAUUCGACAGGAGGCUCACAACAGGC-3';

(SEQ ID NO: 109)
5'-GGGAGACAAGAAUAAGCAUGCCUCAUUAACCCCGCUGUGCCCUGCA
UCACUUCUCAUAGUCCGACACUCGACAGGAGGCUCACAACAGGC-3';
or (SEQ ID NO: 111)
5'-GGGAGACAAGAAUAAGCAUGUCAUCUCACCGCCAUAAUCCUCAACAU
UCUCCCCACCCGAUUCCCGUUCGACAGGAGGCUCACAACAGGC-3'.

14. The aptamer molecule of claim 1, which is capable of being internalised into a CD7-expressing cell.

15. The aptamer molecule of claim 1, wherein some or all of the C and U nucleotide bases have been 2'-fluoro-modified.

16. The aptamer molecule of claim 1 linked to a therapeutic or diagnostic molecule.

17. A pharmaceutical composition comprising an aptamer of claim 1 and a pharmaceutically acceptable carrier.

18. A method for delivering a therapeutic or diagnostic molecule to a cell having a CD7 receptor or for detecting a CD7-expressing cell, comprising contacting the cell with an aptamer of claim 1.

19. The method of claim 18 for detecting a CD7-expressing cell, which further comprises the step of detecting when the aptamer binds to or is internalised by a cell.

* * * * *